United States Patent
Long et al.

(10) Patent No.: US 10,081,626 B2
(45) Date of Patent: *Sep. 25, 2018

(54) 8-AZABICYCLO[3.2.1]OCTANE COMPOUNDS AS MU OPIOID RECEPTOR ANTAGONISTS

(71) Applicant: THERAVANCE BIOPHARMA R&D IP, LLC, South San Francisco, CA (US)

(72) Inventors: Daniel D. Long, San Francisco, CA (US); John R. Jacobsen, San Mateo, CA (US); Lan Jiang, Foster City, CA (US)

(73) Assignee: THERAVANCE BIOPHARMA R&D IP, LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,269

(22) Filed: Apr. 25, 2017

(65) Prior Publication Data

US 2017/0349578 A1    Dec. 7, 2017

Related U.S. Application Data

(60) Continuation of application No. 14/926,225, filed on Oct. 29, 2015, now Pat. No. 9,663,509, which is a continuation of application No. 14/534,798, filed on Nov. 6, 2014, now Pat. No. 9,206,172, which is a continuation of application No. 14/156,014, filed on Jan. 15, 2014, now Pat. No. 8,927,573, which is a division of application No. 13/527,942, filed on Jun. 20, 2012, now Pat. No. 8,664,242, which is a continuation of application No. 12/578,715, filed on Oct. 14, 2009, now Pat. No. 8,263,618, which is a division of application No. 11/711,961, filed on Feb. 28, 2007, now Pat. No. 7,622,508.

(60) Provisional application No. 60/777,962, filed on Mar. 1, 2006, provisional application No. 60/841,028, filed on Aug. 30, 2006.

(51) Int. Cl.
    C07D 451/02    (2006.01)
    A61K 31/439    (2006.01)
    A61K 45/06     (2006.01)
    A61K 31/46     (2006.01)
    A61K 31/485    (2006.01)

(52) U.S. Cl.
    CPC ........ *C07D 451/02* (2013.01); *A61K 31/439* (2013.01); *A61K 31/46* (2013.01); *A61K 31/485* (2013.01); *A61K 45/06* (2013.01)

(58) Field of Classification Search
    CPC .................................................. C07D 451/02
    USPC ........................................ 546/124; 514/304
    See application file for complete search history.

(56) References Cited

U.S. PATENT DOCUMENTS

| | | |
|---|---|---|
| 5,159,081 A | 10/1992 | Cantrell et al. |
| 6,313,312 B1 | 11/2001 | Banks et al. |
| 6,469,030 B2 | 10/2002 | Farrar et al. |
| 6,479,516 B1 | 11/2002 | Gibson et al. |
| 6,552,036 B2 | 4/2003 | Boyd et al. |
| 6,593,348 B2 | 7/2003 | Carrol et al. |
| 6,610,711 B2 | 8/2003 | Armer et al. |
| 6,992,090 B2 | 1/2006 | Le Bourdonnec et al. |
| 7,049,335 B2 | 5/2006 | McHardy et al. |
| 7,056,930 B2 | 6/2006 | Coe et al. |
| 7,087,749 B2 | 8/2006 | Dolle et al. |
| 7,241,887 B2 | 7/2007 | Coe et al. |
| 7,435,822 B2 | 10/2008 | Carson et al. |
| 7,622,508 B2 * | 11/2009 | Long .................... C07D 451/02 514/741 |
| 7,691,878 B2 | 4/2010 | Long et al. |
| 7,902,220 B2 | 3/2011 | Saito et al. |

(Continued)

FOREIGN PATENT DOCUMENTS

| | | |
|---|---|---|
| WO | 2004/089908 A2 | 10/2004 |
| WO | 2004/089909 A1 | 10/2004 |
| WO | 2008/057579 A2 | 5/2008 |

OTHER PUBLICATIONS

McNicol et al., "Management of opioid side effects in cancer-related and chronic noncancer pain: A systematic review", The Journal of Pain, vol. 4, No. 5, pp. 231-256 (Jun. 2003).

Yuan et al., "Methylnaltrexone, a novel peripheral opioid receptor antagonist for the treatment of opioid side effects", Expert Opin. Investig. Drugs, 15(5):541-552 (2006).

Lu et al., "Substituted Bridged Phenyl Piperidines: Orally Active Growth Hormone Secretagogues", Bioorganic & Medicinal Chemistry Letters 13, pp. 1817-1820 (2003).

(Continued)

Primary Examiner — Niloofar Rahmani
(74) Attorney, Agent, or Firm — Jeffrey A. Hagenah; Florence Jovic

(57) ABSTRACT

The invention provides novel 8-azabicyclo[3.2.1]octane compounds of formula (I):

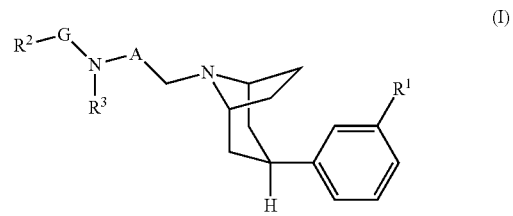

wherein $R^1$, $R^2$, $R^3$, A, and G are defined in the specification, or a pharmaceutically-acceptable salt or solvate thereof, that are antagonists at the mu opioid receptor. The invention also provides pharmaceutical compositions comprising such compounds, methods of using such compounds to treat conditions associated with mu opioid receptor activity, and processes and intermediates useful for preparing such compounds.

7 Claims, 2 Drawing Sheets

(56) References Cited

U.S. PATENT DOCUMENTS

| | | |
|---|---|---|
| 7,902,221 B2 | 3/2011 | Long et al. |
| 7,932,402 B2 | 4/2011 | Colson et al. |
| 7,943,772 B2 | 5/2011 | Dalziel et al. |
| 7,947,710 B2 | 5/2011 | Saito et al. |
| 8,247,555 B2 | 8/2012 | Dalziel et al. |
| 8,247,559 B2 | 8/2012 | Colson et al. |
| 8,263,618 B2 | 9/2012 | Long et al. |
| 8,268,863 B2 | 9/2012 | Saito et al. |
| 8,481,563 B2 | 7/2013 | Saito et al. |
| 8,518,966 B2 | 8/2013 | Long et al. |
| 8,536,335 B2 | 9/2013 | Dalziel et al. |
| 8,664,242 B2 | 3/2014 | Long et al. |
| 8,927,573 B2 | 1/2015 | Long et al. |
| 9,206,172 B2 | 12/2015 | Long et al. |
| 9,663,509 B2 | 5/2017 | Long et al. |
| 2002/0025948 A1 | 2/2002 | Banks et al. |
| 2003/0181447 A1 | 9/2003 | Boyd et al. |
| 2004/0186135 A1 | 9/2004 | Dolle et al. |
| 2004/0204453 A1 | 10/2004 | McHardy et al. |
| 2004/0254190 A1 | 12/2004 | Liras |
| 2005/0085508 A1 | 4/2005 | Fukutomi et al. |
| 2007/0105863 A1 | 5/2007 | Dolle et al. |
| 2008/0207676 A1 | 8/2008 | Dalziel et al. |

OTHER PUBLICATIONS

Le Bourdonnec et al., "trans-3,4-Dimethyl-4-(3-carboxamidophenyl)piperidines: A Novel Class of ☐-Selective Opioid Antagonists", Bioorganic & Medicinal Chemistry Letters, vol. 13 pp. 4459-4462 (2003).

Le Bourdonnec et al., "Elucidation of the Bioactive Conformation of the N-Substituted trans-3,4-Dimethyl-4-(3-hydroxyphenyl)piperidine Class of ☐-Opioid Receptor Antagonists", Journal of Medicinal Chemistry, vol. 49, pp. 7278-7289 (2006).

Le Bourdonnec et al., "Synthesis and Pharmacological Evaluation of Novel Octahydro-1H-pyrido[1,2-a]pyrazine as -Opioid Receptor Antagonists", Journal of Medicinal Chemistry, vol. 49, pp. 7290-7306 (2006).

Diaz et al., "SAR and Biological Evaluation of Novel trans-3,4-dimethyl-4-arylpiperidine Derivatives as Opioid Antagonists", Bioorganic & Medicinal Chemistry Letters, vol. 15 pp. 3844-3848 (2005).

Senagore et al., "Alvimopan accelerates gastrointestinal recovery after bowel resection regardless of age, gender, race, or concomitant medication use". Surgery, vol. 142, pp. 478-486 (2007).

Rothman et al., "Studies of the biogenic amine transporters. 10. Characterization of a novel cocaine binding site in brain membranes prepared from dopamine transporter knockout mice", Synapse, vol. 44, pp. 94-105 (2002).

\* cited by examiner

8-AZABICYCLO[3.2.1]OCTANE COMPOUNDS AS MU OPIOID RECEPTOR ANTAGONISTS

CROSS-REFERENCE TO RELATED APPLICATIONS

This application is a continuation application of U.S. Ser. No. 14/926,225 filed Oct. 29, 2015, now U.S. Pat. No. 9,663,509, which is a continuation of U.S. Ser. No. 14/534,798, filed Nov. 6, 2014, now U.S. Pat. No. 9,206,172, which is a continuation of U.S. Ser. No. 14/156,014, filed Jan. 15, 2014, now U.S. Pat. No. 8,927,573, which is a divisional application of U.S. Ser. No. 13/527,942, filed Jun. 20, 2012, now U.S. Pat. No. 8,664,242, which is a continuation application of U.S. Ser. No. 12/578,715, filed Oct. 14, 2009, now U.S. Pat. No. 8,263,618 B2 which is a divisional application of U.S. Ser. No. 11/711,961, filed Feb. 28, 2007, now U.S. Pat. No. 7,622,508 B2, which claims the benefit of U.S. Provisional Application No. 60/777,962, filed on Mar. 1, 2006, and 60/841,028, filed on Aug. 30, 2006, the disclosures of which are incorporated herein by reference in their entirety.

BACKGROUND OF THE INVENTION

Field of the Invention

The invention is directed to 8-azabicyclo[3.2.1]octane compounds which are useful as mu opioid receptor antagonists. The invention is also directed to pharmaceutical compositions comprising such compounds, methods of using such compounds for treating or ameliorating medical conditions mediated by mu opioid receptor activity, and processes and intermediates useful for preparing such compounds.

State of the Art

It is now generally understood that endogenous opioids play a complex role in gastrointestinal physiology. Opioid receptors are expressed throughout the body, both in the central nervous system and in peripheral regions including the gastrointestinal (GI) tract.

Compounds which function as agonists at opioid receptors, of which morphine is a prototypical example, are the mainstays of analgesic therapy for the treatment of moderate to severe pain. Unfortunately, use of opioid analgesics is often associated with adverse effects on the GI tract, collectively termed opioid-induced bowel dysfunction (OBD). OBD includes symptoms such as constipation, decreased gastric emptying, abdominal pain and discomfort, bloating, nausea, and gastroesophageal reflux. Both central and peripheral opioid receptors are likely involved in the slow-down of gastrointestinal transit after opioid use. However, evidence suggests that peripheral opioid receptors in the GI tract are primarily responsible for the adverse effects of opioids on GI function.

Since the side effects of opioids are predominantly mediated by peripheral receptors, whereas the analgesia is central in origin, a peripherally selective antagonist can potentially block undesirable GI-related side effects without interfering with the beneficial central effects of analgesia or precipitating central nervous system withdrawal symptoms.

Of the three major opioid receptor subtypes, denoted mu, delta, and kappa, most clinically-used opioid analgesics are thought to act via mu opioid receptor activation to exert analgesia and to alter GI motility. Accordingly, peripherally selective mu opioid antagonists are expected to be useful for treating opioid-induced bowel dysfunction. Preferred agents will demonstrate significant binding to mu opioid receptors in vitro and be active in vivo in GI animal models.

Postoperative ileus (POI) is a disorder of reduced motility of the GI tract that occurs after abdominal or other surgery. The symptoms of POI are similar to those of OBD. Furthermore, since surgical patients are often treated during and after surgery with opioid analgesics, the duration of POI may be compounded by the reduced GI motility associated with opioid use. Mu opioid antagonists useful for treating OBD are therefore also expected to be beneficial in the treatment of POI.

SUMMARY OF THE INVENTION

The invention provides novel compounds that possess mu opioid receptor antagonist activity.

Accordingly, the invention provides a compound of formula (I):

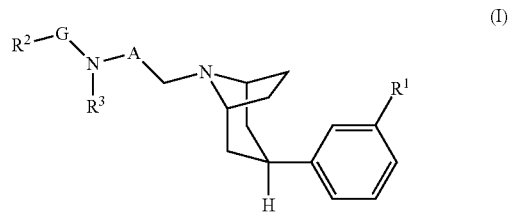

wherein:

$R^1$ is selected from —$OR^a$, —$C(O)NR^aR^b$; —$NHS(O)_2R^c$, —$NR^aR^b$, —$C(O)OR^a$, and —$CH_2OH$;

A is $C_{1-4}$alkylenyl;

$R^2$ is $C_{3-12}$cycloalkyl or $C_{6-10}$aryl, wherein $C_{3-12}$cycloalkyl and $C_{6-10}$aryl are each optionally substituted with one —$OR^a$, with one or two halo, with one or two $C_{1-3}$alkyl substituted with two or three halo; or with one, two, three or four $C_{1-3}$alkyl;

G is $C_{1-4}$alkylenyl;

$R^3$ is selected from hydrogen, —$C(O)R^4$, —$C(O)NHR^5$, —$S(O)_2R^c$, and —$S(O)_2NR^aR^b$;

$R^4$ is $C_{3-6}$cycloalkyl or $C_{1-6}$alkyl, wherein $C_{3-6}$cycloalkyl is optionally substituted with one —$OR^a$, and $C_{1-6}$alkyl is optionally substituted with one or two substituents selected from —$OR^a$, —$C(O)OR^a$, —$S(O)_2R^6$, —$C(O)NR^aR^b$, —$NR^aR^b$, —$NHC(O)NR^aR^b$, —CN, $C_{3-6}$cycloalkyl, and phenyl; or with one -D-$(CH_2)_j$—$R^7$, wherein D is

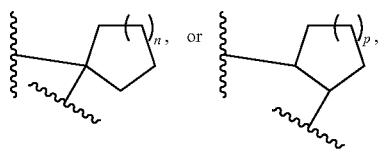

j is 1, 2, or 3, n is 1 or 2, and p is 1 or 2,
$R^6$ is $C_{1-3}$alkyl optionally substituted with $R^7$
$R^7$ is —C(O)OR$^a$, —C(O)NR$^a$R$^b$, —NR$^a$R$^b$, or —NHC(O)NR$^a$R$^b$
$R^5$ is $C_{1-6}$alkyl, benzo[1.3]dioxol, or —(CH$_2$)$_q$-phenyl, wherein phenyl is optionally substituted with one or two substituents selected from halo, —OR$^a$, $C_{1-3}$alkyl, and $C_{1-3}$alkoxy, wherein $C_{1-3}$alkyl, and $C_{1-3}$alkoxy are optionally substituted with 2 or 3 halo, and
q is 0, 1, or 2;
$R^a$ and $R^b$ are each independently hydrogen or $C_{1-4}$alkyl, and;
$R^c$ is $C_{1-3}$alkyl;
provided that when $R^2$ is phenyl substituted at the 4 position, $R^3$ is not —C(O)R$^4$ wherein $R^4$ is $C_{1-4}$alkyl substituted with —C(O)OR$^a$;
or a pharmaceutically-acceptable salt or solvate thereof.

The invention also provides a pharmaceutical composition comprising a compound of the invention and a pharmaceutically-acceptable carrier.

The invention also provides a method of treating a disease or condition associated with mu opioid receptor activity, e.g. a disorder of reduced motility of the gastrointestinal tract such as opioid-induced bowel dysfunction and post-operative ileus, the method comprising administering to the mammal, a therapeutically effective amount of a compound or of a pharmaceutical composition of the invention.

The compounds of the invention can also be used as research tools, i.e. to study biological systems or samples, or for studying the activity of other chemical compounds. Accordingly, in another of its method aspects, the invention provides a method of using a compound of formula (I), or a pharmaceutically acceptable salt or solvate thereof, as a research tool for studying a biological system or sample or for discovering new compounds having mu opioid receptor activity, the method comprising contacting a biological system or sample with a compound of the invention and determining the effects caused by the compound on the biological system or sample.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a disease or condition associated with mu opioid receptor activity, e.g. a disorder of reduced motility of the gastrointestinal tract, in a mammal.

DETAILED DESCRIPTION OF THE INVENTION

Figure 1:
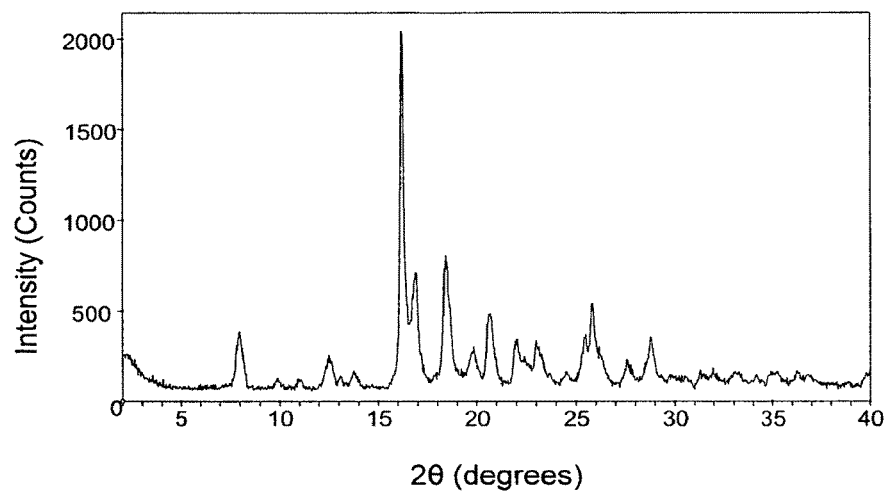
FIG. 1 shows an x-ray powder diffraction pattern of crystalline 3-endo-(8-{2-[cyclohexylmethyl-((S)-2,3-dihydroxy-propionyl)amino]ethyl}-8-azabicyclo[3.2.1]oct-3-yl)benzamide glycolate of the invention.

The invention provides 8-azabicyclo[3.2.1]octane mu opioid receptor antagonists of formula (I), or pharmaceutically-acceptable salts or solvates thereof. The following substituents and values are intended to provide representative examples of various aspects of this invention. These representative values are intended to further define such aspects and are not intended to exclude other values or limit the scope of the invention.

In a specific aspect of the invention, $R^1$ is selected from —OR$^a$, —C(O)NR$^a$R$^b$; —NHS(O)$_2$R$^c$, —NR$^a$R$^b$, —C(O)OR$^a$, and —CH$_2$OH.

In other specific aspects, $R^1$ is selected from —OR$^a$, —C(O)NR$^a$R$^b$; and —NHS(O)$_2$R$^c$, or $R^1$ is —OR$^a$ or —C(O)NR$^a$R$^b$, or $R^1$ is —OH or —C(O)NR$^a$R$^b$.

In yet another specific aspect, $R^1$ is —OH or —C(O)NH$_2$.
In a further specific aspect, $R^1$ is —C(O)NH$_2$.
In a specific aspect, A is $C_{1-4}$alkylenyl.
In other specific aspects, A is —(CH$_2$)$_2$—, —CH(CH$_3$)—, or —CH$_2$—; or A is —(CH$_2$)$_2$— or —CH$_2$—; or A is —CH$_2$—.
In a specific aspect, G is $C_{1-4}$alkylenyl.
In other specific aspects, G is —(CH$_2$)$_3$—, —(CH$_2$)$_2$—, or —CH$_2$—; or G is —(CH$_2$)$_2$— or —CH$_2$—; or G is —CH$_2$—.

In a specific aspect, $R^2$ is $C_{3-12}$cycloalkyl or $C_{6-10}$aryl, wherein $C_{3-12}$cycloalkyl and $C_{6-10}$aryl are each optionally substituted with one —OR$^a$, with one or two halo, with one or two $C_{1-3}$alkyl substituted with two or three halo; or with one, two, three or four $C_{1-3}$alkyl.

In another specific aspect, $R^2$ is $C_{3-12}$cycloalkyl or $C_{6-10}$aryl, wherein $C_{3-12}$cycloalkyl and $C_{6-10}$aryl are each optionally substituted with one —OR$^a$, with one or two halo, or with one or two $C_{1-3}$alkyl optionally substituted with two or three halo.

In another specific aspect, $R^2$ is $C_{3-12}$cycloalkyl or $C_{6-10}$aryl, wherein $C_{3-12}$cycloalkyl and $C_{6-10}$aryl are each optionally substituted with one or two halo, or with one or two $C_{1-3}$alkyl optionally substituted with 2 or 3 halo. Representative $R^2$ groups within this aspect include, but are not limited to, cyclopentyl, cyclohexyl, cycloheptyl, adamantyl, phenyl, and naphthyl, wherein cyclohexyl, phenyl, and naphthyl are each optionally substituted with one or two halo or with $C_{1-3}$alkyl substituted with two or three halo.

In another specific aspect, $R^2$ is cyclobutyl, cyclopentyl, cyclohexyl, adamantyl, or phenyl, wherein cyclohexyl and phenyl are each optionally substituted with one or two halo or with $C_{1-3}$alkyl substituted with two or three halo.

In another specific aspect, $R^2$ is cyclohexyl or phenyl, wherein cyclohexyl and phenyl are each optionally substituted with one or two halo or with $C_{1-3}$alkyl substituted with two or three halo; or $R^2$ is cyclohexyl or phenyl, wherein cyclohexyl and phenyl are each optionally substituted with one or two halo.

In another specific aspect, $R^2$ is cyclohexyl optionally substituted with one or two halo.

In still another specific aspect, $R^2$ is cyclohexyl.

In yet another specific aspect, $R^2$ is phenyl optionally substituted with one or two halo.

In yet another specific aspect, $R^2$ is phenyl.

In a specific aspect, $R^3$ is selected from hydrogen, —C(O)$R^4$, —C(O)NH$R^5$, —S(O)$_2R^c$, and —S(O)$_2NR^aR^b$.

In another specific aspect, $R^3$ is selected from hydrogen, —C(O)$R^4$, —S(O)$_2R^c$, and —S(O)$_2NR^aR^b$ In a specific aspect, $R^3$ is selected from hydrogen, —C(O)$R^4$, and —C(O)NH$R^5$.

In other specific aspects, $R^3$ is —C(O)$R^4$ or —C(O)NH$R^5$, or $R^3$ is —C(O)$R^4$.

In another specific aspect, $R^3$ is —C(O)$R^4$ wherein $R^4$ is $C_{3-6}$cycloalkyl or $C_{1-6}$alkyl, and wherein $C_{1-6}$alkyl is optionally substituted with one or two —O$R^a$, or with one substituent selected from —C(O)O$R^a$, —S(O)$_2R^6$, —C(O)NR$^aR^b$, —NR$^aR^b$, and $C_{3-6}$cycloalkyl, and $R^6$ is $C_{1-3}$alkyl optionally substituted with $R^7$, wherein $R^7$ is —C(O)O$R^a$.

In another specific aspect, $R^3$ is —C(O)$R^4$ wherein $R^4$ is $C_{3-6}$cycloalkyl or $C_{1-6}$alkyl, wherein $C_{3-6}$cycloalkyl is optionally substituted with one —O$R^a$, and $C_{1-6}$alkyl is optionally substituted with one or two substituents selected from —O$R^a$, —C(O)O$R^a$, —S(O)$_2R^6$, —C(O)NR$^aR^b$, —NR$^aR^b$, —CN, $C_{3-6}$cycloalkyl, and phenyl, wherein $R^6$ is $C_{1-3}$alkyl optionally substituted with $R^7$, wherein $R^7$ is —C(O)O$R^a$.

In another specific aspect, $R^3$ is —C(O)$R^4$ wherein $R^4$ is $C_{5-6}$ cycloalkyl optionally substituted with one —OH.

In other specific aspects $R^3$ is —C(O)$R^4$, wherein $R^4$ is $C_{1-4}$alkyl wherein $C_{1-4}$alkyl is optionally substituted with one or two substituents selected from —O$R^a$, —S(O)$_2R^6$, —NR$^aR^b$, —CN, $C_{3-6}$cycloalkyl, and phenyl, wherein $R^6$ is $C_{1-3}$alkyl; or $R^4$ is $C_{1-4}$alkyl wherein $C_{1-4}$alkyl is optionally substituted with one or two substituents selected from —OH, —OCH$_3$, —S(O)$_2$CH$_3$, —NH$_2$, —NHCH$_3$, —NH(CH$_3$)$_2$, and phenyl. Representative values of $R^4$ within this aspect include but are not limited to —CH$_2$OH, —CH(OH)CH$_2$OH, —CH$_2$SO$_2$CH$_3$, —CH$_2$SO$_2$CH$_2$C(O)OH, —CH$_2$CN, —CH$_2$OCH$_3$, —C(CH$_3$)$_2$OH, —CH(CH$_3$)OH, —CH(OH)CH(CH$_3$) OH, —CH(OH)CH$_3$, —(CH$_2$)N(CH$_3$)$_2$, and CH(NHCH$_3$)CH$_2$OH.

In still another specific aspect, $R^3$ is —C(O)$R^4$ wherein $R^4$ is selected from —CH$_2$OH, —CH(OH)CH$_2$OH, —CH(OH)CH$_3$, and —CH$_2$SO$_2$CH$_3$.

In another specific aspect, $R^3$ is —C(O)NH$R^5$.

In another specific aspect $R^3$ is —C(O)NH$R^5$, wherein $R^5$ is $C_{1-6}$alkyl, benzo[1.3]dioxol, or —(CH$_2$)$_q$-phenyl, wherein q is 0 or 1 and phenyl is optionally substituted with one or two substituents selected from chloro, fluoro, —OH, and —OCF$_2$.

In other specific aspects, $R^3$ is —C(O)NH$R^5$, wherein $R^5$ is $C_{1-6}$alkyl or benzo[1.3]dioxol; or $R^5$ is —CH(CH$_3$)$_2$ or benzo[1.3]dioxol; or $R^5$ is —CH(CH$_3$)$_2$.

The invention further provides a compound of formula (I) wherein:

$R^1$ is —O$R^a$ or —C(O)NR$^aR^b$;
A is —(CH$_2$)$_2$—, or —CH$_2$—;
G is —(CH$_2$)$_2$— or —CH$_2$—;
$R^2$ is selected from cyclobutyl, cyclopentyl, cyclohexyl, adamantyl, and phenyl, wherein cyclohexyl and phenyl are each optionally substituted with 1 or 2 halo or with $C_{1-3}$alkyl substituted with 2 or 3 halo;
$R^3$ is selected from —C(O)$R^4$, —S(O)$_2R^c$, —S(O)$_2$NR$^aR^b$, and —C(O)NH$R^5$;

$R^4$ is $C_{3-6}$cycloalkyl or $C_{1-6}$alkyl, wherein $C_{3-6}$cycloalkyl is optionally substituted with one —O$R^a$, and $C_{1-6}$alkyl is optionally substituted with one or two substituents selected from —O$R^a$, —C(O)O$R^a$, —S(O)$_2R^6$, —C(O)NR$^aR^b$, —NR$^aR^b$, —CN, $C_{3-6}$cycloalkyl, and phenyl, wherein $R^6$ is $C_{1-3}$alkyl optionally substituted with $R^7$, wherein $R^7$ is —C(O)O$R^a$;

$R^5$ is $C_{1-4}$alkyl, benzo[1.3]dioxol, or —(CH$_2$)$_q$-phenyl, wherein q is 0 or 1 and phenyl is optionally substituted with one or two substituents selected from chloro, fluoro, —OH, and —OCF$_2$;

$R^a$ and $R^b$ are each independently hydrogen or $C_{1-3}$alkyl; and $R^c$ is $C_{1-3}$alkyl;

provided that when $R^2$ is phenyl substituted at the 4 position, $R^3$ is not —C(O)$R^4$ wherein $R^4$ is $C_{1-4}$alkyl substituted with —C(O)OH;

or a pharmaceutically-acceptable salt or solvate thereof.

In yet another aspect, the invention provides a compound of formula (I) wherein:

$R^1$ is —OH or —C(O)NH$_2$;
A is —(CH$_2$)$_2$— or —CH$_2$—;
G is —(CH$_2$)$_2$— or —CH$_2$—;
$R^2$ is cyclohexyl or phenyl, wherein cyclohexyl is optionally substituted with 1 or 2 halo;
$R^3$ is —C(O)$R^4$ or —C(O)NH$R^5$;
$R^4$ is selected from —CH$_2$OH, —CH(OH)CH$_2$OH, —CH(OH)CH$_3$, and —CH$_2$SO$_2$CH$_3$; and
$R^5$ is —CH(CH$_3$)$_2$ or benzo[1.3]dioxol;
or a pharmaceutically-acceptable salt or solvate thereof.

The invention further provides a compound of formula (I'):

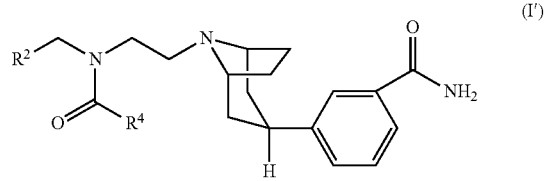

wherein:

$R^2$ is cyclohexyl or phenyl, wherein cyclohexyl and phenyl are each optionally substituted with one or two halo; and $R^4$ is $C_{3-6}$cycloalkyl or $C_{1-4}$alkyl,
wherein
$C_{3-6}$cycloalkyl is optionally substituted with one —O$R^a$, and
$C_{1-4}$alkyl is optionally substituted with one or two substituents selected from —O$R^a$, —S(O)$_2R^6$, —NR$^aR^b$, —CN, and $C_{3-6}$cycloalkyl,
$R^a$ and $R^b$ are each independently hydrogen or $C_{1-3}$alkyl; and
$R^6$ is $C_{1-3}$alkyl;
or a pharmaceutically-acceptable salt or solvate thereof.

Within this aspect, the invention provides a compound of formula (I') wherein $R^4$ is $C_{1-4}$alkyl optionally substituted with one or two substituents selected from —OH, —OCH$_3$, —S(O)$_2$CH$_3$, —NH$_2$, —NHCH$_3$, and —NH(CH$_3$)$_2$.

Further within this aspect, the invention provides a compound of formula (I') wherein $R^2$ is cyclohexyl or 4,4-difluorocyclohexyl, and $R^4$ is $C_{1-4}$alkyl substituted with one or two —OH.

The invention further provides the compounds of Examples 1-204 herein.

The chemical naming convention used herein is illustrated for the compound of Example 1:

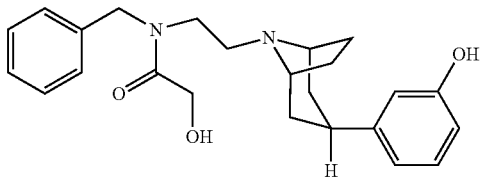 [SMILES: O=C(CO)N(CCN1C2CCC1CC(c1cccc(O)c1)C2)Cc1ccccc1]

which is N-benzyl-2-hydroxy-N-{2-[3-endo-(3-hydroxyphenyl)-8-azabicyclo[3.2.1]oct-8-yl]ethyl}acetamide. Alternatively, using the IUPAC conventions as implemented in AutoNom software, (MDL Information Systems, GmbH, Frankfurt, Germany), the compound is denoted N-Benzyl-2-hydroxy-N-{2-[(1R,3R,5S)-3-(3-hydroxyphenyl)-8-azabicyclo[3.2.1]oct-8-yl]ethyl}acetamide. The names used herein therefore correspond to the IUPAC notation with the endo orientation of the substituted phenyl group with respect to the 8-azabicyclo[3.2.1]octane group indicated explicitly. All of the compounds of the invention are in the endo orientation. For convenience, as used herein, the term "8-azabicyclooctane" means 8-azabicyclo[3.2.1]octane.

In addition to the endo stereochemistry with respect to the bicyclo group, the compounds of the invention may contain a chiral center in the substituents $R^4$, $R^5$, or A. Accordingly, the invention includes racemic mixtures, pure stereoisomers, and stereoisomer-enriched mixtures of such isomers, unless otherwise indicated. When the stereochemistry of a compound is specified, including both the orientation with respect to the 8-azabicyclooctane group and the chirality in any substituents $R^4$, $R^5$, or A, it will be understood by those skilled in the art, that minor amounts of other stereoisomers may be present in the compositions of the invention unless otherwise indicated, provided that any utility of the composition as a whole is not eliminated by the presence of such other isomers.

Definitions

When describing the compounds, compositions and methods of the invention, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl, ethyl, n-propyl (n-Pr), isopropyl (i-Pr), n-butyl (n-Bu), sec-butyl, isobutyl, tert-butyl, n-pentyl, n-hexyl, n-heptyl, n-octyl, n-nonyl, n-decyl and the like.

The term "alkylenyl" means a divalent saturated hydrocarbon group which may be linear or branched or combinations thereof. Unless otherwise defined, such alkylenyl groups typically contain from 1 to 10 carbon atoms. Representative alkylenyl groups include, by way of example, methylene, ethylene, n-propylene, n-butylene, propane-1,2-diyl (1-methylethylene), 2-methylpropane-1,2-diyl (1,1-dimethylethylene) and the like.

The term "alkoxy" means a monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl, cyclobutyl, cyclopentyl, cyclohexyl, cycloheptyl, cyclooctyl, adamantyl, and the like.

The term "aryl" means a monovalent aromatic hydrocarbon having a single ring (i.e. phenyl) or fused rings (i.e. napthalene). Unless otherwise defined, such aryl groups typically contain from 6 to 10 carbon ring atoms. Representative aryl groups include, by way of example, phenyl, and napthalene-1-yl, napthalene-2-yl and the like.

The term "halo" means fluoro, chloro, bromo or iodo.

The term "compound" means a compound that was synthetically prepared or prepared in any other way, such as by metabolism.

The term "therapeutically effective amount" means an amount sufficient to effect treatment when administered to a patient in need of treatment.

The term "treatment" as used herein means the treatment of a disease, disorder, or medical condition in a patient, such as a mammal (particularly a human) which includes:

(a) preventing the disease, disorder, or medical condition from occurring, i.e., prophylactic treatment of a patient;
(b) ameliorating the disease, disorder, or medical condition, i.e., eliminating or causing regression of the disease, disorder, or medical condition in a patient, including counteracting the effects of other therapeutic agents;
(c) suppressing the disease, disorder, or medical condition, i.e., slowing or arresting the development of the disease, disorder, or medical condition in a patient; or
(d) alleviating the symptoms of the disease, disorder, or medical condition in a patient.

The term "pharmaceutically-acceptable salt" means a salt prepared from an acid or base which is acceptable for administration to a patient, such as a mammal. Such salts can be derived from pharmaceutically-acceptable inorganic or organic acids and from pharmaceutically-acceptable bases. Typically, pharmaceutically-acceptable salts of compounds of the present invention are prepared from acids.

Salts derived from pharmaceutically-acceptable acids include, but are not limited to, acetic, adipic, benzenesulfonic, benzoic, camphorsulfonic, citric, ethanesulfonic, fumaric, gluconic, glutamic, glycolic, hydrobromic, hydrochloric, lactic, maleic, malic, mandelic, methanesulfonic, mucic, nitric, oxalic, pantothenic, phosphoric, succinic, sulfuric, tartaric, p-toluenesulfonic, xinafoic (1-hydroxy-2-naphthoic acid), naphthalene-1,5-disulfonic acid and the like.

The term "solvate" means a complex or aggregate formed by one or more molecules of a solute, i.e. a compound of the invention or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

It will be appreciated that the term "or a pharmaceutically-acceptable salt or solvate thereof" is intended to include all permutations of salts and solvates, such as a solvate of a pharmaceutically-acceptable salt of a compound of formula (I).

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

General Synthetic Procedures

Compounds of the invention can be prepared from readily available starting materials using the following general methods and procedures. Although a particular aspect of the present invention is illustrated in the schemes below, those skilled in the art will recognize that all aspects of the present invention can be prepared using the methods described herein or by using other methods, reagents and starting materials known to those skilled in the art. It will also be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal, are described in T. W. Greene and G. M. Wuts, *Protecting Groups in Organic Synthesis*, Third Edition, Wiley, New York, 1999, and references cited therein.

In one method of synthesis, compounds of the invention are prepared as illustrated in Scheme A. (The substituents and variables shown in the following schemes have the definitions provided above unless otherwise indicated).

which $R^{4a}$ is —$CH_2OC(O)CH_3$ and L is chloro. When $R^{4a}$ is a protected form of $R^4$, reaction (i) also includes a deprotection step, which is not shown. To prepare a compound in which $R^1$ represents amino, preferably, a protected amino group is used for $R^1$ in intermediate (II) and the reaction sequence includes a final deprotection step.

Optimal reaction conditions for reaction (i) of Scheme A to prepare compounds of formula (Ia) may vary depending on the chemical properties of the reagent $R^{4a}C(O)$-L, as is well known to those skilled in the art. For example, when L is a halo leaving group, such as chloro, reaction (i) is typically conducted by contacting intermediate (II) with between about 1 and about 2 equivalents of a compound of formula $R^{4a}C(O)$-L in an inert diluent, such as dichloromethane, in the presence of an excess of base, for example between about 3 and about 6 equivalents of base, such as N,N-diisopropylethylamine or triethylamine. Suitable inert diluents also include 1,1,2,2-tetrachloroethane, tetrahydrofuran, dimethylacetamide, and the like. The reaction is typically conducted at a temperature in the range of about −50° C. to about 30° C. for about a quarter hour to about 16 hours, or until the reaction is substantially complete.

When the reagent $R^{4a}C(O)$-L is a carboxylic acid or a carboxylate salt, reaction (i) is typically conducted by contacting intermediate (II) with between about 1 and about 5 equivalents of the acid $R^{4a}C(O)OH$ or the carboxylate salt, for example, $R^{4a}C(O)OLi$, in an inert diluent, in the presence of an excess of base, both as described above, and in the presence of between about 1 and about 6 equivalents of an activating agent such as N,N-carbonyl diimidazole (CDI), N,N,N',N'-tetramethyl-O-(7-azabenzotriazol-1-yl)uronium hexafluorophosphate (HATU) or 1-(3-dimethylaminopropyl)-3-ethylcarbodiimide (EDC). The reaction is typically conducted at a temperature in the range of about 25° C. to about 100° C. for about 2 hours to about 16 hours, or until the reaction is substantially complete.

As described in the examples below, particular compounds of formula (Ia) may be prepared by coupling an

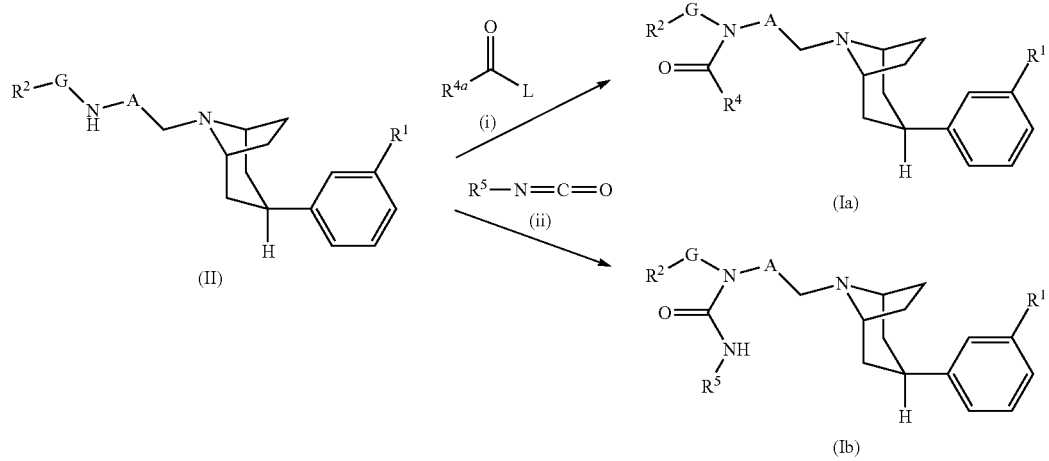

Scheme A

In Scheme A, $R^{4a}$ represents $R^4$ or a protected form of $R^4$, and L represents a leaving group, such as chloro or bromo, or $R^{4a}C(O)$-L represents a carboxylic acid or a carboxylate salt. For example, to prepare a compound in which $R^4$ is —$CH_2OH$, a useful reagent is acetoxy acetyl chloride, in intermediate of formula (II) with alternative reagents, such as cyclic anhydrides or a dioxolane carboxylic acid.

The preparation of urea compounds of formula (Ib) is illustrated in reaction (ii) of Scheme A. The reaction is typically conducted by contacting intermediate (II) with between about 1 and about 2 equivalents of an isocyanate compound $R^5$—N=C=O in the presence of between about 3 and about 6 equivalents of base, such as N,N-diisopropylethylamine. The reaction is typically conducted at ambient temperature for about an hour to about 16 hours, or until the reaction is substantially complete.

One general procedure for the preparation of an intermediate of formula (II) is illustrated in Scheme B1, where $P^1$ represents an amino-protecting group.

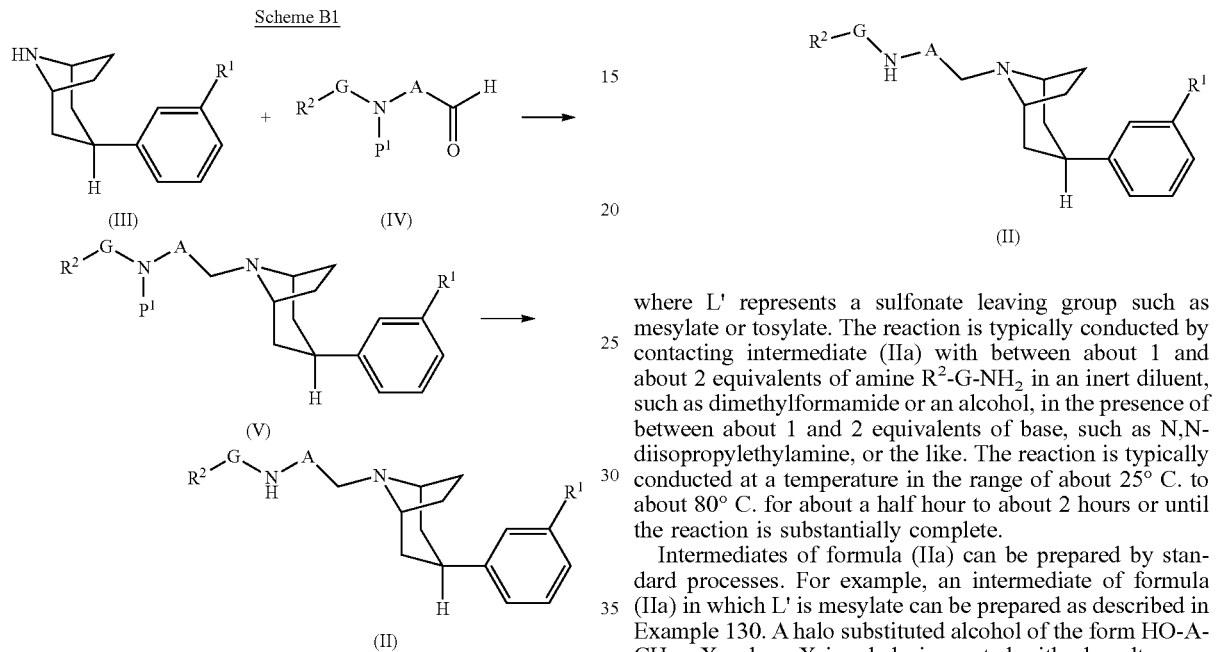

An intermediate of formula (III), referred to here as a "phenyltropane", is reductively N-alkylated by reaction with an aldehyde of formula (IV) to provide a protected intermediate (V) which is deprotected by conventional procedures to provide intermediate (II).

The initial reaction is typically conducted by contacting intermediate (III) with between about 1 and about 2 equivalents of an aldehyde of formula (IV) in a suitable diluent, typically an inert diluent, in the presence of between about 0.9 and about 2 equivalents of a reducing agent. The reaction is typically conducted at a temperature in the range of about 0° C. to ambient temperature for about a half hour to about 3 hours or until the reaction is substantially complete. Suitable inert diluents include dichloromethane and the like listed above. Additionally, alcohols, such as methanol or ethanol, may be used as the diluent. Typical reducing agents include sodium triacetoxyborohydride, sodium borohydride, and sodium cyanoborohydride. The product (V) is isolated by conventional means. The deprotection of (V) uses standard procedures. For example, when the protecting group $P^1$ is Boc, (V) is typically treated with an acid, such as trifluoroacetic acid to provide intermediate (II). In the reaction of Scheme B1, intermediate (III) may be provided in free base or in salt form. In the latter case, about 1 equivalent of base may optionally be used in the reaction.

Another general procedure for the preparation of an intermediate of formula (II) is illustrated in Scheme B2.

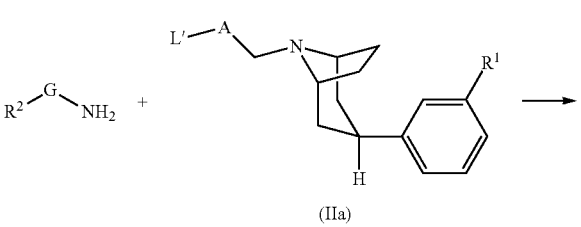

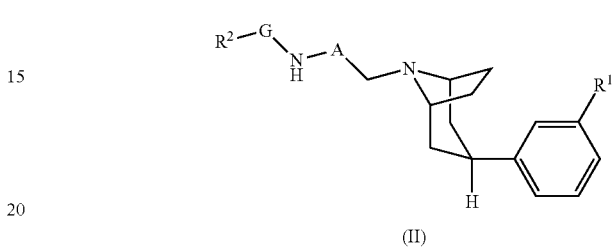

where L' represents a sulfonate leaving group such as mesylate or tosylate. The reaction is typically conducted by contacting intermediate (IIa) with between about 1 and about 2 equivalents of amine $R^2$-G-$NH_2$ in an inert diluent, such as dimethylformamide or an alcohol, in the presence of between about 1 and 2 equivalents of base, such as N,N-diisopropylethylamine, or the like. The reaction is typically conducted at a temperature in the range of about 25° C. to about 80° C. for about a half hour to about 2 hours or until the reaction is substantially complete.

Intermediates of formula (IIa) can be prepared by standard processes. For example, an intermediate of formula (IIa) in which L' is mesylate can be prepared as described in Example 130. A halo substituted alcohol of the form HO-A-$CH_2$—X, where X is a halo is reacted with phenyltropane (III) to provide an alcohol intermediate in which HO-A-$CH_2$— is coupled to the tropane nitrogen, which is then reacted with methane sulfonyl chloride to provide intermediate (IIa).

A third process for the preparation of intermediate (II) is illustrated in Scheme B3

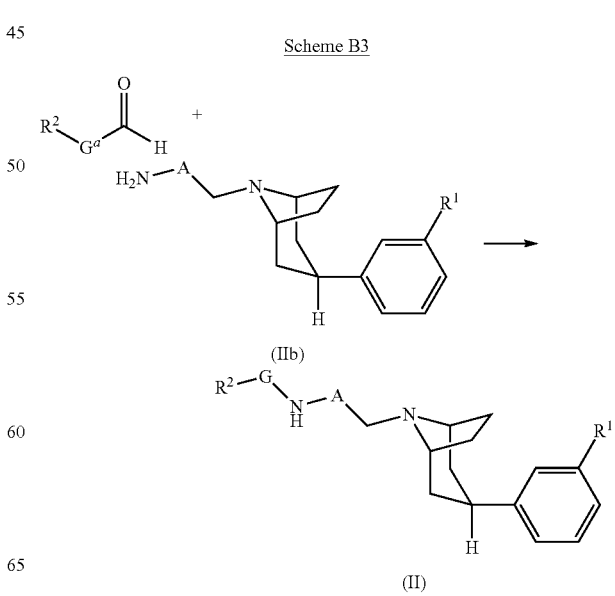

where $G^a$ is defined such that $G^a$-$CH_2$ is the variable G, i.e. $G^a$ is $C_{1-3}$alkylenyl or $G^a$ is a covalent bond. Intermediate (IIb) is reductively N-alkylated by reaction with the aldehyde $R^2$-$G^a$-C(O)H to provide intermediate (II). The reaction is typically conducted under the conditions described above for the N-alkylation reaction of (III) in Scheme B1. Intermediate (IIb) may be prepared by reductive N-alkylation of phenyltropane (III) by a protected amino aldehyde of the form N(HP$^1$)-A-C(O)H, followed by a deprotection step.

In another alternative process for the preparation of intermediate (II) a carboxylic acid reagent is coupled with the phenyltropane (III) in the presence of an amide coupling agent to form an amide intermediate which is then reduced to provide intermediate (II), as described, for example, in Preparation 22 below.

In yet another alternative process, an intermediate of formula (II) in which the variable A is methylene, is prepared by the process of Scheme C.

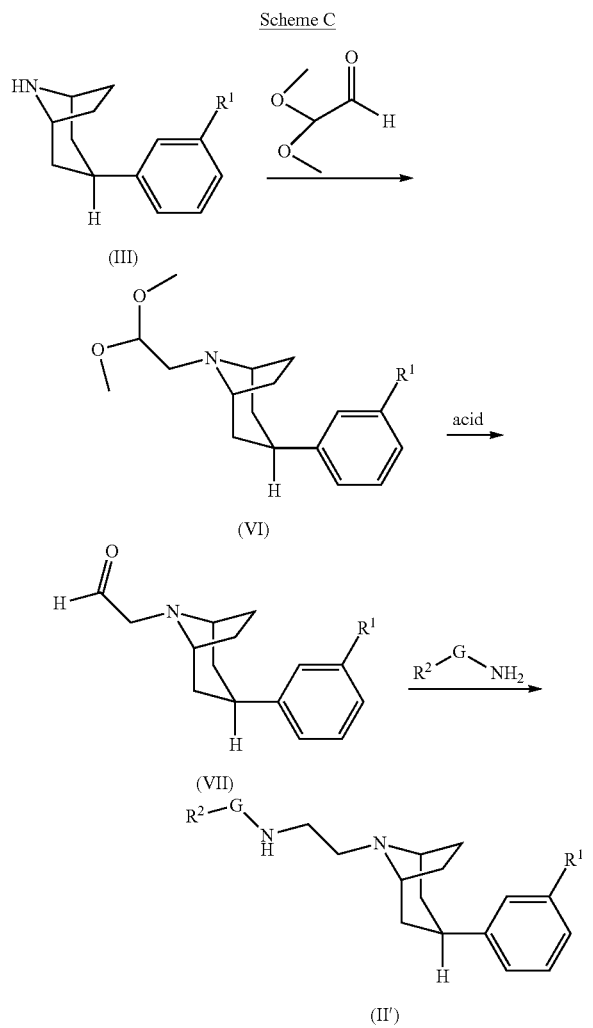

As shown in Scheme C, intermediate (III) is reductively N-alkylated by reaction with dimethoxyacetaldehyde to provide the acetal intermediate (VI) under N-alkylation conditions described previously. Next, the acetal intermediate (VI) is hydrolyzed in an aqueous solution of a strong acid, for example 3N or 6N HCl to provide the aldehyde intermediate (VII) as a hydrochloride salt. This reaction is typically conducted at a temperature of between about 20 and about 40° C. for about 3 to about 72 hours or until the reaction is substantially complete.

Finally, reductive amination of intermediate (VII) with an amine of the formula $R^2$-G-$NH_2$ provides the intermediate of formula (II'). Typically, aldehyde (VII) in an inert diluent is contacted with between about 1 and about 2 equivalents of the amine in the presence of between about 1 and about 2 equivalents of a reducing agent and about one equivalent of base. The reaction is typically conducted at ambient temperature for between about 15 minutes and 2 hours or until the reaction is substantially complete.

Intermediates (III) and (IV) can be prepared from readily available starting materials. For example, one process for the preparation of the phenyltropane (III') in which $R^1$ is hydroxy is illustrated in Scheme D.

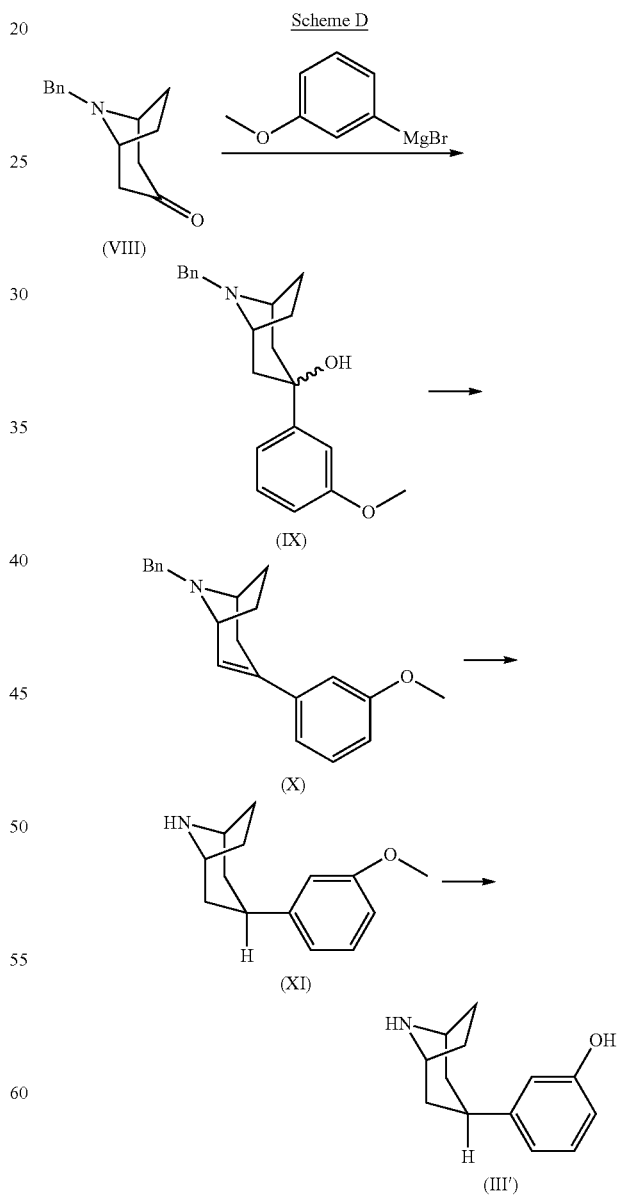

where Bn denotes the amino-protecting group benzyl. Protected tropanone (VIII) can be prepared by the reaction of 2,5-dimethoxy tetrahydrofuran with benzylamine and 1,3-acetonedicarboxylic acid in an acidic aqueous solution in the presence of a buffering agent as described in US 2005/0228014. (See also, U.S. Pat. No. 5,753,673).

First, tropanone (VIII) is added to a solution of between about 1 and about 2 equivalents of the Grignard reagent 3-methoxyphenyl magnesium bromide in an inert diluent. The reaction is typically conducted at a temperature of between about 0° C. and about 10° C. for between about 1 and about 3 hours or until the reaction is substantially complete. Transmetalation of the Grignard reagent from magnesium to cerium by reaction with an equivalent amount of cerous chloride prior to use is advantageous for obtaining a good yield of intermediate (IX). The hydroxy substituent is eliminated from intermediate (IX) by treatment with aqueous 6N HCl to provide the hydrochloride salt of intermediate (X). This reaction is typically conducted at a temperature of between about 50° C. and about 100° C. for between about 1 and about 3 hours or until the reaction is substantially complete.

Hydrogenation of intermediate (X) saturates the double bond of the alkene moiety and removes the benzyl protecting group to provide intermediate (XI). Typically, the reaction is conducted by exposing the HCl salt of (X) dissolved in ethanol to a hydrogen atmosphere in the presence of a transition metal catalyst. Finally, the methyl group is removed from intermediate (XI) by contacting a cooled solution of intermediate (XI) in an inert diluent with between about 1 and about 2 equivalents of boron tribromide, hydrogen bromide, or boron trichloride. The reaction is typically conducted at a temperature of between about −80° C. and about 0° C. for between about 12 and about 36 hours or until the reaction is substantially complete. Alternatively, intermediate (XI) can be isolated as a hydrochloride salt, which is treated with between about 1 and about 2 equivalents of aqueous hydrobromic acid to provide the phenyltropane intermediate (III').

Intermediate (III') can be isolated by conventional procedures as a free base or as a hydrobromide salt. Crystallization of the hydrobromide salt provides intermediate (III') with high stereospecificity in the endo configuration (endo to exo ratio of greater than 99.1:0.8).

As described in the examples below, certain variations of the above process can alternatively be used to prepare intermediate (III'). For example different reagents can be used to eliminate the hydroxy from (IX) to obtain intermediate (X), which may be isolated as a freebase instead of in salt form. In yet another alternative process sequence, treatment of intermediate (IX) with boron tribromide or HBr removes the methyl group as it eliminates the hydroxy substituent.

One process for preparing intermediate (III") in which the variable R¹ is —C(O)NH₂ uses (III') as a starting material as shown in Scheme E.

Scheme E

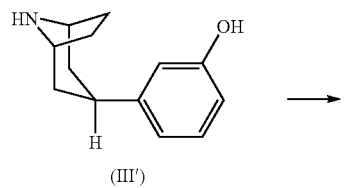
(III')

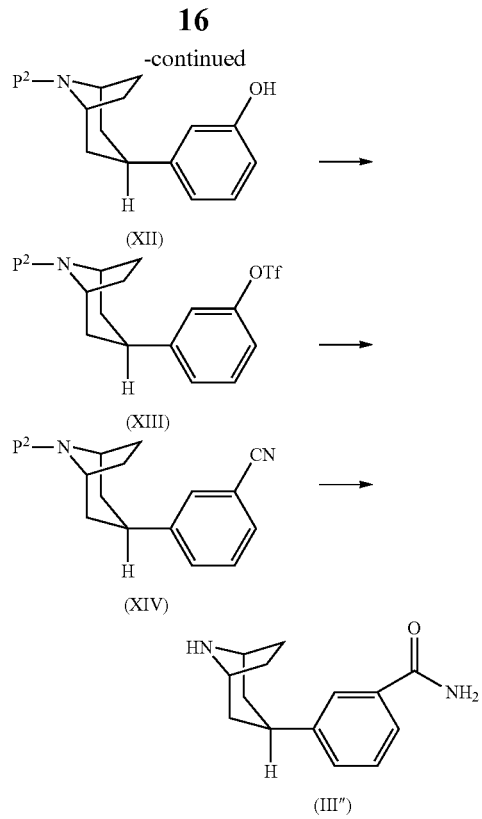

where —OTf represents trifluoromethane sulfonate (commonly triflate) and P² represents an amino-protecting group.

For example, when Boc is used as the protecting group, first, the phenyltropane (III') is typically reacted with about 1 equivalent of di-tert-butyl dicarbonate (commonly Boc₂O) to provide the Boc-protected intermediate (XII). The reactants are typically cooled to about 0° C. and then allowed to warm to ambient temperature over a period of between about 12 and about 24 hours. When tri-fluoroacetyl is used as the protecting group, typically (III') is reacted with about 2 equivalents of tri-fluoroacetyl anhydride to form the protected intermediate (XII). Next, intermediate (XII) in an inert diluent is contacted with a slight excess, for example about 1.1 equivalents of trifluoromethane sulfonyl chloride in the presence of between about 1 and about 2 equivalents of base to provide intermediate (XIII), which can be isolated by conventional procedures. Reaction of (XIII) with zinc cyanide in the presence of a transition metal catalyst, provides intermediate (XIV). This reaction is typically conducted at a temperature between about 60° C. and 120° C. under an inert atmosphere for about 2 to about 12 hours or until the reaction is substantially complete.

Finally, the nitrile intermediate (XIV) is hydrolyzed and deprotected to provide the carboxamide intermediate (III"). Typically, in this reaction, when P² is Boc, intermediate (XIV) in an acidic solvent, for example trifluoroacetic acid, is contacted with between about 4 and about 6 equivalents of concentrated sulfuric acid. Typically the reaction is conducted in the temperature range of between about 50° C. and about 80° C. for about 8 to about 24 hours or until the reaction is substantially complete. The product is typically isolated in freebase form. Alternatively, the transformation of (XIV) to (III") is performed in two steps in which, the nitrile substituent of intermediate (XIV) is first hydrolyzed to the carboxamide by reaction with potassium carbonate and hydrogen peroxide and then the Boc protecting group is removed by treatment with acid, e.g. trifluoroacetic acid.

When a tri-fluoroacetyl protecting group is used, the nitrile intermediate is first hydrolyzed to the carboxamide in concentrated sulfuric acid as described above. Quenching of the hydrolysis reaction by addition of base also removes the protecting group. The product is typically isolated as the hydrochloric acid salt. Yet another alternative reaction sequence which makes use of a protected cyanophenyltropane intermediate is described in the examples below.

An intermediate of formula (III) in which $R^1$ is —NHS$(O)_2R^c$ can be prepared from intermediate (XIII) of Scheme E. As described, for example, in Preparation 23 below, an intermediate of formula (III) in which $R^1$ represents —NHS$(O)_2CH_3$, can be prepared by reacting intermediate (XIII) with benzophenone imine in the presence of a palladium catalyst to provide a 3-aminophenyl substituted protected 8-azabicyclooctane intermediate, which, in turn, is reacted with methanesulfonylchloride to prepare a protected intermediate in which $R^1$ is —NHS$(O)_2CH_3$. The protecting group is then removed by conventional methods, to provide the intermediate of formula (III).

The triflate substituted intermediate (XIII) is also useful as a starting material for the preparation of other key intermediates to compounds of the inventions. An intermediate of formula (III) in which $R^1$ is the ester, —C(O)OR$^a$ wherein $R^a$ is $C_{1-3}$alkyl, can be prepared by the palladium catalyzed carbonylation of (XIII) in the presence of an alcoholic solvent $R^aOH$ followed by a deprotection step. The intermediate (III) in which $R^1$ is the acid, —C(O)OH, can be obtained by hydrolysis of the protected form of intermediate (III) in which $R^1$ is the ester, in the presence of an inorganic base and subsequent deprotection. Reduction of the protected acid intermediate, using, for example a reducing agent such as sodium borohydride, can provide the intermediate of formula (III) in which $R^1$ is —CH$_2$OH after deprotection.

Intermediates of formula (IV), used in Scheme B1, can be prepared from an alcohol of formula (XV) as illustrated in process Scheme F:

borane reduction process, to provide an alcohol intermediate of formula (XV). Next, addition of an amino-protecting group by conventional procedures forms intermediate (XVI) which is oxidized to provide an intermediate of formula (IV). Intermediate (IV) can be prepared and stored as a bisulfite adduct, from which the aldehyde is released prior to use.

In an alternate process for the preparation of compounds of the invention of formula (Ia), the phenyltropane intermediate (III) is reacted with an intermediate of formula (XVII)

Scheme G

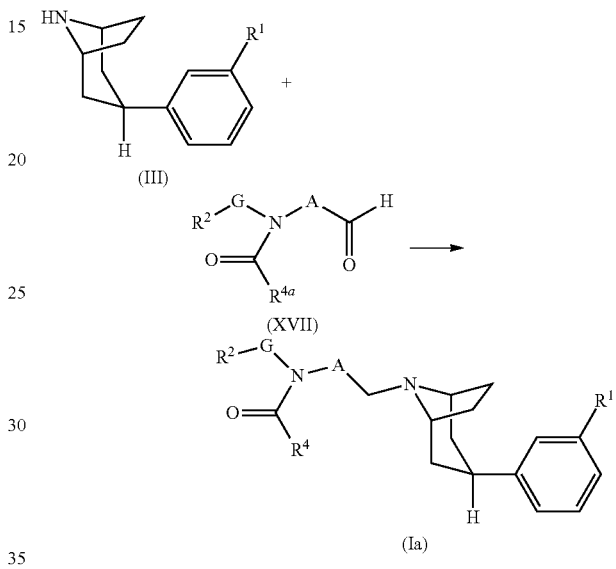

under conditions similar to those described for the initial reaction of Scheme B1. When $R^{4a}$ is a protected form of $R^4$, a final deprotection step is performed to provide compound (Ia). Intermediate (XVII) can be prepared by reaction of the Scheme F

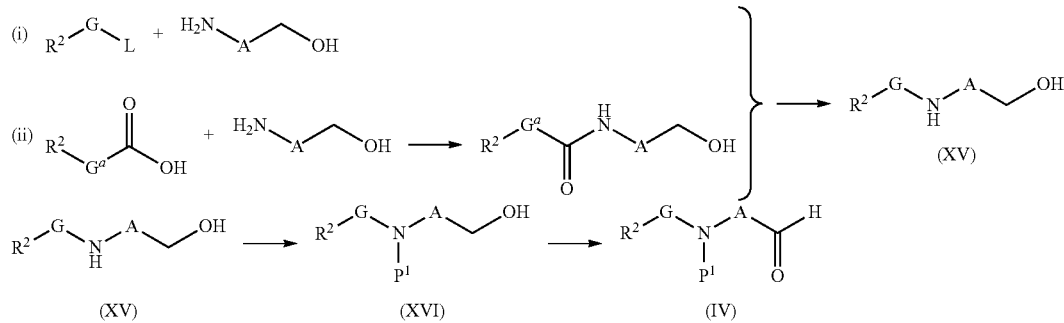

where $G^a$ is defined such that $G^a$-CH$_2$ is G and L is a leaving group. Alcohol (XV) can be prepared by the process of reaction (i) in which an alcohol of the formula H$_2$N-A-CH$_2$—OH is reacted with a substituted alkylhalide of the formula $R^2$-G-L under conditions similar to those described for the reaction of Scheme B2. Alcohol (XV) can also be prepared by the process of reaction (ii) under typical acid coupling conditions as described previously, to form the intermediate amide which is reduced, for example by a alcohol (XV) with the reagent $R^{4a}C(O)$-L to add —C(O)$R^{4a}$ to the nitrogen of (XV), followed by oxidation of the resulting alcohol to the aldehyde (XVII). Urea compounds of the invention of formula (Ib) may be prepared by processes analogous to that shown in Scheme G.

Further details regarding specific reaction conditions and other procedures for preparing representative compounds of the invention or intermediates thereto are described in the examples below.

Accordingly, in a method aspect, the invention provides a process for preparing a compound of formula (I), or a salt or protected derivative thereof, the process comprising (a) reacting a compound of formula (II) with (i) a compound of formula $R^{4a}C(O)$-L or (ii) a compound of formula $R^5$—N=C=O; or (b) reacting a compound of formula (III) with a compound of formula (XVII); and, optionally, removing the protecting group or groups from $R^{4a}$, to provide a compound of formula (I), or a salt or protected derivative thereof.

In separate aspects, the invention further provides a compound of formula (II) and a compound of formula (III), wherein the variables $R^1$, $R^2$, G, and A take any of the values described in aspects of the invention disclosed above. In particular, the invention provides a compound of formula (II), wherein $R^1$ is —C(O)NH$_2$, $R^2$ is cyclohexyl or phenyl wherein cyclohexyl and phenyl are each optionally substituted with one or two halo, G is —CH$_2$— and A is —CH$_2$—. In addition, in yet another specific aspect, the invention provides a compound of formula (III) wherein $R^1$ is —OR$^a$ or —C(O)NR$^a$R$^b$, or wherein $R^1$ is —OH or —C(O)NH$_2$.

Pharmaceutical Compositions

The 8-azabicyclooctane compounds of the invention are typically administered to a patient in the form of a pharmaceutical composition or formulation. Such pharmaceutical compositions may be administered to the patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a therapeutically effective amount of a compound of formula (I) or a pharmaceutically acceptable salt thereof. Optionally, such pharmaceutical compositions may contain other therapeutic and/or formulating agents if desired. When discussing compositions, the "compound of the invention" may also be referred to herein as the "active agent". As used herein, the term "compound of the invention" is intended to include compounds of formula (I) as well as the species embodied in formula (I'). "Compound of the invention" includes, in addition, pharmaceutically-acceptable salts and solvates of the compound unless otherwise indicated.

The pharmaceutical compositions of the invention typically contain a therapeutically effective amount of a compound of the present invention or a pharmaceutically-acceptable salt thereof. Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in *Remington: The Science and Practice of Pharmacy*, 20$^{th}$ Edition, Lippincott Williams & White, Baltimore, Md. (2000); and H. C. Ansel et al., *Pharmaceutical Dosage Forms and Drug Delivery Systems*, 7$^{th}$ Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid!methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

If desired, the compounds of this invention may be administered in combination with one or more other therapeutic agents. In this embodiment, a compound of this invention is either physically mixed with the other therapeutic agent to form a composition containing both agents; or each agent is present in separate and distinct compositions which are administered to the patient simultaneously or sequentially.

For example, a compound of formula I can be combined with second therapeutic agent using conventional procedures and equipment to form a composition comprising a compound of formula I and a second therapeutic agent. Additionally, the therapeutic agents may be combined with a pharmaceutically acceptable carrier to form a pharmaceutical composition comprising a compound of formula I, a second therapeutic agent and a pharmaceutically acceptable carrier. In this embodiment, the components of the composition are typically mixed or blended to create a physical mixture. The physical mixture is then administered in a therapeutically effective amount using any of the routes described herein. Alternatively, the therapeutic agents may remain separate and distinct before administration to the patient. In this embodiment, the agents are not physically mixed together before administration but are administered simultaneously or at separate times as separate compositions. Such compositions can be packaged separately or may be packaged together as a kit. The two therapeutic agents in the kit may be administered by the same route of administration or by different routes of administration.

Any therapeutic agent compatible with the compounds of the present invention may be used as the second therapeutic agent. In particular, prokinetic agents acting via mechanisms other than mu opioid receptor antagonism may be used in combination with the present compounds. For example, 5-HT$_4$ receptor agonists, such as tegaserod, renzapride, mosapride, prucalopride, 1-isopropyl-1H-indazole-3-carboxylic acid {(1S,3R,5R)-8-[2-(4-acetylpiperazin-1-yl)ethyl]-8-azabicyclo[3.2.1]oct-3-yl}amide, 1-isopropyl-2-oxo-1,2-dihydroquinoline-3-carboxylic acid {(1S,3R,5R)-8-

[(R)-2-hydroxy-3-(methanesulfonyl-methyl-amino)propyl]-8-azabicyclo[3.2.1]oct-3-yl}amide, or 4-(4-{[(2-isopropyl-1H-benzoimidazole-4-carbonyl)amino]methyl}-piperidin-1-ylmethyl)piperidine-1-carboxylic acid methyl ester may be used as the second therapeutic agent.

Additional useful prokinetic agents include, but are not limited to, 5-$HT_3$ receptor agonists (e.g. pumosetrag), 5-$HT_{1A}$ receptor antagonists (e.g. AGI 001), alpha-2-delta ligands (e.g. PD-217014), chloride channel openers (e.g. lubiprostone), dopamine antagonists (e.g. itopride, metaclopramide, domperidone), GABA-B agonists (e.g. baclofen, AGI 006), kappa opioid agonists (e.g. asimadoline), muscarinic $M_1$ and $M_2$ antagonists (e.g. acotiamide), motilin agonists (e.g. mitemcinal), guanylate cyclase activators (e.g. MD-1100) and ghrelin agonists (e.g. Tzp 101, RC 1139).

In addition, the compounds of the invention can be combined with opioid therapeutic agents. Such opioid agents include, but are not limited to, morphine, pethidine, codeine, dihydrocodeine, oxycontin, oxycodone, hydrocodone, sufentanil, fentanyl, remifentanil, buprenorphine, methadone, and heroin.

Numerous additional examples of such therapeutic agents are known in the art and any such known therapeutic agents may be employed in combination with the compounds of this invention. Secondary agent(s), when included, are present in a therapeutically effective amount, i.e. in any amount that produces a therapeutically beneficial effect when co-administered with a compound of the invention. Suitable doses for the other therapeutic agents administered in combination with a compound of the invention are typically in the range of about 0.05 µg/day to about 100 mg/day.

Accordingly, the pharmaceutical compositions of the invention optionally include a second therapeutic agent as described above.

The following examples illustrate representative pharmaceutical compositions of the present invention:

Formulation Example A: Hard Gelatin Capsules for Oral Administration

A compound of the invention (50 g), spray-dried lactose (200 g) and magnesium stearate (10 g) are thoroughly blended. The resulting composition is loaded into a hard gelatin capsule (260 mg of composition per capsule).

Formulation Example B: Hard Gelatin Capsules for Oral Administration

A compound of the invention (20 mg), starch (89 mg), microcrystalline cellulose (89 mg), and magnesium stearate (2 mg) are thoroughly blended and then passed through a No. 45 mesh U.S. sieve. The resulting composition is loaded into a hard gelatin capsule (200 mg of composition per capsule).

Formulation Example C: Gelatin Capsules for Oral Administration

A compound of the invention (10 mg), polyoxyethylene sorbitan monooleate (50 mg), and starch powder (250 mg) are thoroughly blended and then loaded into a gelatin capsule (310 mg of composition per capsule).

Formulation Example D: Tablets for Oral Administration

A compound of the invention (5 mg), starch (50 mg), and microcrystalline cellulose (35 mg) are passed through a No. 45 mesh U.S. sieve and mixed thoroughly. A solution of polyvinylpyrrolidone (10 wt % in water, 4 mg) is mixed with the resulting powders, and this mixture is then passed through a No. 14 mesh U.S. sieve. The granules so produced are dried at 50-60EC and passed through a No. 18 mesh U.S. sieve. Sodium carboxymethyl starch (4.5 mg), magnesium stearate (0.5 mg) and talc (1 mg), which have previously been passed through a No. 60 mesh U.S. sieve, are then added to the granules. After mixing, the mixture is compressed on a tablet machine to afford a tablet weighing 100 mg.

Formulation Example E: Tablets for Oral Administration

A compound of the invention (25 mg), microcrystalline cellulose (400 mg), fumed silicon dioxide (10 mg), and stearic acid (5 mg) are thoroughly blended and then compressed to form tablets (440 mg of composition per tablet).

Formulation Example F: Single-Scored Tablets for Oral Administration

A compound of the invention (15 mg), cornstarch (50 mg), croscarmellose sodium (25 mg), lactose (120 mg), and magnesium stearate (5 mg) are thoroughly blended and then compressed to form single-scored tablet (215 mg of compositions per tablet).

Formulation Example G: Suspension for Oral Administration

The following ingredients are thoroughly mixed to form a suspension for oral administration containing 100 mg of active ingredient per 10 mL of suspension:

| Ingredients | Amount |
| --- | --- |
| Compound of the invention | 0.1 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum k (Vanderbilt Co.) | 1.0 g |
| Flavoring | 0.035 mL |
| Colorings | 0.5 mg |
| Distilled water | q.s. to 100 mL |

Formulation Example H: Dry Powder Composition

A micronized compound of the invention (1 mg) is blended with lactose (25 mg) and then loaded into a gelatin inhalation cartridge. The contents of the cartridge are administered using a powder inhaler.

Formulation Example J: Injectable Formulation

A compound of the invention (0.1 g) is blended with 0.1 M sodium citrate buffer solution (15 mL). The pH of the resulting solution is adjusted to pH 6 using 1 N aqueous hydrochloric acid or 1 N aqueous sodium hydroxide. Sterile normal saline in citrate buffer is then added to provide a total volume of 20 mL.

It will be understood that any form of the compounds of the invention, (i.e. free base, pharmaceutical salt, or solvate)

that is suitable for the particular mode of administration, can be used in the pharmaceutical compositions discussed above.

Utility

The 8-azabicyclooctane compounds of the invention are antagonists at the mu opioid receptor and therefore are expected to be useful for treating medical conditions mediated by mu opioid receptors or associated with mu opioid receptor activity, i.e. medical conditions which are ameliorated by treatment with a mu opioid receptor antagonist. In particular, the compounds of the invention are expected to be useful for treating adverse effects associated with use of opioid analgesics, i.e. symptoms such as constipation, decreased gastric emptying, abdominal pain, bloating, nausea, and gastroesophageal reflux, termed collectively opioid-induced bowel dysfunction. The mu opioid receptor antagonists of the invention are also expected to be useful for treating post-operative ileus, a disorder of reduced motility of the gastrointestinal tract that occurs after abdominal or other surgery. In addition, it has been suggested that mu opioid receptor antagonist compounds may be used for reversing opioid-induced nausea and vomiting. Further, those mu opioid receptor antagonists exhibiting some central penetration may be useful in the treatment of dependency on, or addiction to, narcotic drugs, alcohol, or gambling, or in preventing, treating, and/or ameliorating obesity.

Since compounds of the invention increase motility of the gastrointestinal (GI) tract in animal models, the compounds are expected to be useful for treating disorders of the GI tract caused by reduced motility in mammals, including humans. Such GI motility disorders include, by way of illustration, chronic constipation, constipation-predominant irritable bowel syndrome (C-IBS), diabetic and idiopathic gastroparesis, and functional dyspepsia.

In one aspect, therefore, the invention provides a method of increasing motility of the gastrointestinal tract in a mammal, the method comprising administering to the mammal a therapeutically effective amount of a pharmaceutical composition comprising a pharmaceutically-acceptable carrier and a compound of the invention.

When used to treat disorders of reduced motility of the GI tract or other conditions mediated by mu opioid receptors, the compounds of the invention will typically be administered orally in a single daily dose or in multiple doses per day, although other forms of administration may be used. For example, particularly when used to treat post-operative ileus, the compounds of the invention may be administered parenterally. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating disorders of reduced motility of the GI tract or other disorders mediated by mu opioid receptors will range from about 0.0007 to about 20 mg/kg/day of active agent, including from about 0.0007 to about 1.4 mg/kg/day. For an average 70 kg human, this would amount to from about 0.05 to about 100 mg per day of active agent.

In one aspect of the invention, the compounds of the invention are used to treat opioid-induced bowel dysfunction. When used to treat opioid-induced bowel dysfunction, the compounds of the invention will typically be administered orally in a single daily dose or in multiple doses per day. Preferably, the dose for treating opioid-induced bowel dysfunction will range from about 0.05 to about 100 mg per day.

In another aspect of the invention, the compounds of the invention are used to treat post-operative ileus. When used to treat post-operative ileus, the compounds of the invention will typically be administered orally or intravenously in a single daily dose or in multiple doses per day. Preferably, the dose for treating post-operative ileus will range from about 0.05 to about 100 mg per day.

The invention also provides a method of treating a mammal having a disease or condition associated with mu opioid receptor activity, the method comprising administering to the mammal a therapeutically effective amount of a compound of the invention or of a pharmaceutical composition comprising a compound of the invention.

As described above, compounds of the invention are mu opioid receptor antagonists. The invention further provides, therefore, a method of antagonizing a mu opioid receptor in a mammal, the method comprising administering a compound of the invention to the mammal.

The mu opioid receptor antagonists of the invention are optionally administered in combination with another therapeutic agent or agents, in particular, in combination with prokinetic agents acting via non-mu opioid mechanisms. Accordingly, in another aspect, the methods and compositions of the invention further comprise a therapeutically effective amount of another prokinetic agent.

In addition, the compounds of the invention are also useful as research tools for investigating or studying biological systems or samples having mu opioid receptors, or for discovering new compounds having mu opioid receptor activity. Any suitable biological system or sample having mu opioid receptors may be employed in such studies which may be conducted either in vitro or in vivo. Representative biological systems or samples suitable for such studies include, but are not limited to, cells, cellular extracts, plasma membranes, tissue samples, mammals (such as mice, rats, guinea pigs, rabbits, dogs, pigs, etc.) and the like. The effects of contacting a biological system or sample comprising a mu opioid receptor with a compound of the invention are determined using conventional procedures and equipment, such as the radioligand binding assay and functional assay described herein or other functional assays known in the art. Such functional assays include, but are not limited to, ligand-mediated changes in intracellular cyclic adenosine monophosphate (cAMP), ligand-mediated changes in activity of the enzyme adenylyl cyclase, ligand-mediated changes in incorporation of analogs of guanosine triphosphate (GTP), such as [$^{35}$S]GTPγS (guanosine 5'-O-(γ-thio)triphosphate) or GTP-Eu, into isolated membranes via receptor catalyzed exchange of GTP analogs for GDP analogs, and ligand-mediated changes in free intracellular calcium ions. A suitable concentration of a compound of the invention for such studies typically ranges from about 1 nanomolar to about 500 nanomolar.

When using compounds of the invention as research tools for discovering new compounds have mu opioid receptor activity, binding or functional data for a test compound or a group of test compounds is compared to the mu opioid receptor binding or functional data for a compound of the invention to identify test compounds that have superior binding or functional activity, if any. This aspect of the invention includes, as separate embodiments, both the generation of comparison data (using the appropriate assays) and the analysis of the test data to identify test compounds of interest.

Among other properties, compounds of the invention have been found to exhibit potent binding to mu opioid receptors and little or no agonism in mu receptor functional assays. Therefore, the compounds of the invention are potent mu opioid receptor antagonists. Further, compounds of the invention have demonstrated predominantly peripheral activity as compared with central nervous system activity in animal models. Therefore, these compounds can be expected to reverse opioid-induced reductions in GI motility without interfering with the beneficial central effects of analgesia. These properties, as well as the utility of the compounds of the invention, can be demonstrated using various in vitro and in vivo assays well-known to those skilled in the art. Representative assays are described in further detail in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

Boc=tert-butoxycarbonyl
(Boc)$_2$O=di-tert-butyl dicarbonate
DABCO=1,4-diazaobicylco[2,2,2]octane triethylenediamine
DCM=dichloromethane
DIPEA=N,N-diisopropylethylamine
DMA=dimethylacetamide
DMAP=dimethylaminopyridine
DMF=N,N-dimethylformamide
DMSO=dimethyl sulfoxide
EtOAc=ethyl acetate
EtOH=ethanol
HATU=N,N,N',N'-tetramethyl-O-(7-azabenzotriazol-1-yl)uronium hexafluorophosphate
MeCN=acetonitrile
MeOH=methanol
MeTHF=2-methyltetrahydrofuran
MTBE=tert-butyl methyl ether
PyBop=benzotriazol-1-yloxytripyrrolidino-phosphonium hexafluorophosphate
TFA=trifluoroacetic acid
THF=tetrahydrofuran Reagents (including secondary amines) and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry, the details of which are given below and separately in specific examples of reactions. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC: a general protocol is described below. Characterization of reaction products was routinely carried out by mass and $^1$H-NMR spectrometry. For NMR measurement, samples were dissolved in deuterated solvent (CD$_3$OD, CDCl$_3$, or DMSO-d$_6$), and $^1$H-NMR spectra were acquired with a Varian Gemini 2000 instrument (300 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1100 LC/MSD instrument.

Preparation 1: Synthesis of 3-endo-(8-azabicyclo [3.2.1]oct-3-yl)-phenol a. Preparation of 8-benzyl-8-azabicyclo[3.2.1]octan-3-one A mixture of 2,5-dimethoxy tetrahydrofuran (20.5 g, 155.1 mmol), water (42.5 mL) and concentrated HCl (30 mL) was stirred at room temperature for about 30 minutes. To this stirring mixture was sequentially added water (62.5 mL), a premixed solution of benzylamine (17.9 mL, 162.9 mmol), water (87.5 mL) and concentrated HCl (23 mL), a premixed solution of 1,3-acetonedicarboxylic acid (25 g) and water (100 mL), and a solution of Na$_2$HPO$_4$ (16.5 g) in water (50 mL). The resulting mixture was adjusted to pH 4 to 5 with 40% aqueous NaOH and stirred overnight at room temperature. The mixture was acidified to pH 3 with concentrated HCl and heated to 85° C. for 3 hours. After cooling to room temperature, the mixture was basified with 20% aqueous NaOH, saturated with solid sodium chloride and extracted with dichloromethane. The organic layer was washed with brine, dried over sodium sulfate, filtered and concentrated to give a dark oil which was purified by flash column chromatography. The product was eluted with 20% ethyl acetate/hexanes. Desired fractions were combined and concentrated to give the title intermediate as a yellowish oil (16.17 g).

b. Preparation of 8-benzyl-3-exo-(3-methoxy-phenyl)-8-azabicyclo[3.2.1]octan-3-ol A solution of 8-benzyl-8-azabicyclo[3.2.1]octan-3-one (7.28 g, 33.8 mmol) in dry THF (113 mL) was cooled to −78° C. under nitrogen. To this cold solution was added a 1.0 M solution of 3-methoxyphenyl magnesium bromide in THF (44 mL) via a dropping funnel. The resulting mixture was warmed to room temperature and stirred for about 20 minutes. The reaction was cooled to 0° C. and additional 3-methoxyphenyl magnesium bromide (30 mL, 30.0 mmol) in THF was added. The reaction was warmed to room temperature again after addition and stirred for 30 minutes. The reaction was quenched with saturated ammonium chloride and the product extracted with ethyl acetate. The organic layer was washed with brine, dried over sodium sulfate, filtered and concentrated. The residue was purified by column chromatography and eluted with 5% (200 mL), 10% (200 mL), 15% (200 mL), 20% (200 mL), 30% (200 mL), and 100% ethyl acetate/hexanes. Desired fractions were combined and concentrated to give the title intermediate as a light yellowish oil (4.0 g). Starting material (3.87 g) was recovered. (m/z): [M+H]$^+$ calcd for C$_{21}$H$_{25}$NO$_2$ 324.20; found, 324.5.

c. Preparation of 3-(8-benzyl-8-aza-bicyclo[3.2.1] oct-2-en-3-yl)-phenol

To a solution of 8-benzyl-3-endo-(3-methoxy-phenyl)-8-azabicyclo[3.2.1]octan-3-ol (4.65 g, 14.4 mmol) in dichloromethane (70 mL) at 0° C. was added 1.0 M boron tribromide in dichloromethane (28 mL). The resulting mixture was stirred at 0° C. for one hour then allowed to warm to room temperature and stirred at that temperature overnight. The reaction mixture was concentrated and co-evaporated with methanol three times. The resulting residue was dissolved in 50% acetic acid in water (20 mL), filtered, and purified by reverse phase preparative HPLC to give the TFA salt of the title compound (4.6 g). (m/z): [M+H]$^+$ calcd for C$_{20}$H$_{21}$NO 292.17; found, 292.3.

d. Synthesis of 3-endo-(8-aza-bicyclo[3.2.1]oct-3-yl)-phenol

To a solution of the TFA salt of 3-(8-benzyl-8-aza-bicyclo[3.2.1]oct-2-en-3-yl)-phenol (2.0 g) in ethanol (200 mL) at room temperature was added palladium hydroxide on carbon (50 wt % water, 20% w/w on carbon, 800 mg). The resulting suspension was degassed and treated overnight under a hydrogen atmosphere. The reaction mixture was filtered through Celite and rinsed with ethanol. The filtrate was concentrated to give the TFA salt of the title compound (1.2 g). (m/z): [M+H]$^+$ calcd for C$_{13}$H$_{17}$NO 204.14; found, 204.3.

Preparation 2: Synthesis of 3-endo-[8-(2-benzylamino-ethyl)-8-aza-bicyclo[3.2.1]oct-3-yl]-phenol a. Preparation of 3-endo-[8-(2,2-dimethoxyethyl)-8-azabicyclo[3.2.1]oct-3-yl]phenol To a stirred suspension of 3-endo-(8-aza-bicyclo[3.2.1]oct-3-yl)-phenol (2.0 g, 6.3 mmol) in CH$_2$Cl$_2$ (25 mL) at room temperature was added sequentially N,N-diisopropylethylamine (814 mg, 6.3 mmol), 2,2-dimethoxyacetaldehyde (1.31 g, 12.6 mmol) and sodium triacetoxyborohydride (1.73 g, 8.19 mmol). The resulting mixture was sonicated to aid dissolution and stirred at room temperature for 30 minutes. The reaction was diluted with dichloromethane. The organic layer was washed with saturated sodium bicarbonate followed by brine, dried over sodium sulfate, filtered, and concentrated to give a yellowish oil, which was used directly in the next step without purification. (m/z): [M+H]$^+$ calcd for C$_{17}$H$_{25}$NO$_3$ 292.19; found, 292.3.

b. Preparation of [3-endo-(3-hydroxyphenyl)-8-azabicyclo [3.2.1]oct-8-yl]-acetaldehyde The oily product of the previous step was treated with 6N aq HCl (30 mL) at room temperature for two days. Solvents were removed under vacuum. The residue was then dissolved in water and freeze dried to give the title intermediate as its HCl salt (1.3 g). (m/z): [M+H]$^+$ calcd for C$_{15}$H$_{19}$NO$_2$ 246.15; found, 246.1.

c. Synthesis of 3-endo-[8-(2-benzylaminoethyl)-8-aza-bicyclo[3.2.1]oct-3-yl]-phenol To a stirred solution of the HCl salt of [3-endo-(3-hydroxyphenyl)-8-aza-bicyclo[3.2.1]oct-8-yl]-acetaldehyde (384 mg, 1.36 mmol) in dichloromethane (4.5 mL) at room temperature was added sodium triacetoxyborohydride (374 mg, 1.76 mmol) followed by N,N-diisopropylethylamine (176 mg, 1.36 mmol) and benzylamine (175 mg, 1.63 mmol). The solution was stirred at room temperature for 30 minutes, and the reaction was quenched with saturated sodium bicarbonate. The aqueous layer was extracted with dichloromethane. The resulting organic layer was washed with brine, dried over sodium sulfate, filtered and concentrated to give a oily residue. The residue was redissolved in 50% acetic acid in water, filtered and purified by reverse phase preparative HPLC to give the title compound as its bis TFA salt (191 mg). (m/z): [M+H]$^+$ calcd for C$_{22}$H$_{28}$N$_2$O 337.23; found, 337.3.

Preparation 3

Following the method of Preparation 2, step c, substituting the appropriate amine reagent for benzylamine, the bis TFA salts of the following compounds were prepared:

3-endo-{8-[2-(cyclohexylmethylamino)ethyl]-8-azabicyclo[3.2.1]oct-3-yl}phenol; (m/z): [M+H]$^+$ calcd for C$_{22}$H$_{34}$N$_2$O 343.28; found, 343.5.

3-endo-{8-[2-(3-fluorobenzylamino)ethyl]-8-azabicyclo [3.2.1]oct-3-yl}-phenol; (m/z): [M+H]$^+$ calcd for C$_{22}$H$_{27}$FN$_2$O 355.22; found, 355.5.

3-endo-{8-[2-(2,6-difluorobenzylamino)ethyl]-8-azabicyclo[3.2.1]oct-3-yl}-phenol; (m/z): [M+H]$^+$ calcd for C$_{22}$H$_{26}$F$_2$N$_2$O 373.21; found, 373.3.

3-endo-{8-[2-(4-fluorobenzylamino)ethyl]-8-azabicyclo [3.2.1]oct-3-yl}-phenol; (m/z): [M+H]$^+$ calcd for C$_{22}$H$_{27}$FN$_2$O 355.22; found, 355.3.

3-endo-{8-[2-(4-chlorobenzylamino)ethyl]-8-azabicyclo [3.2.1]oct-3-yl}-phenol; (m/z): [M+H]$^+$ calcd for C$_{22}$H$_{27}$ClN$_2$O 371.19; found, 371.4.

Preparation 4: Synthesis of 3-endo-(8-aza-bicyclo [3.2.1]oct-3-yl)-phenol a. Preparation of trifluoro-methanesulfonic Acid 8-benzyl-8-aza-bicyclo[3.2.1]oct-2-en-3-yl Ester To a solution of 8-benzyl-8-azabicyclo[3.2.1]octan-3-one (12.8 g, 59.5 mmol) in anhydrous tetrahydrofuran (200 mL) at –78° C. was added a 1.0 M solution of sodium hexamethyldisilazane (77 mL, 77.4 mmol) in THF dropwise. The resulting mixture was stirred at –78° C. for thirty minutes before a THF solution (100 mL) of N-phenyltrifluoromethanesulfonimide (PhNHTf$_2$) (25 g, 69.9 mmol) was added. After about forty minutes, thin layer chromatography indicated the reaction was not complete. Additional PhNTf$_2$ (2.0 g) in THF was added. After 30 minutes, the reaction was quenched with saturated ammonium chloride. The layers were separated and the organic layer was washed with saturated ammonium chloride twice, followed by brine, dried over sodium sulfate, filtered, and concentrated. The residue was further purified by flash chromatography and eluted with 0% (500 mL) to 5% (500 mL) to 10% (500 mL) to 15% (500 mL) to 20% (100 mL) ethyl acetate/hexanes. Desired fractions were combined and concentrated to give a yellowish oil (25.6 g, contaminated with N-phenyltrifluoromethanesulfonamide (PhNHTf). (m/z): [M+H]$^+$ calcd for C$_{15}$H$_{16}$F$_3$NO$_3$S 348.09; found, 348.0.

b. Preparation of 8-benzyl-3-(3-benzyloxyphenyl)-8-azabicyclo[3.2.1]oct-2-ene

To a solution of the product of the previous step (24.6 g, contaminated with PhNHTf) in THF (120 mL) and DMA (120 mL) at room temperature was added 3-benzyloxyphenylboronic acid (16.46 g), potassium carbonate (19.9 g) and tetrakis(triphenylphosphine)palladium(0) (5.0 g). The resulting mixture was degassed, flushed with nitrogen and then stirred under nitrogen atmosphere overnight. The reaction mixture was filtered through a pad of Celite and the filtrate was concentrated to give a dark thick oil which was purified by flash chromatography (and eluted with 40% ethyl acetate in hexanes) to yield the title intermediate (6.9 g). (m/z): [M+H]$^+$ calcd for $C_{27}H_{27}NO$ 382.22; found 382.5.

c. Preparation of 3-endo-(8-aza-bicyclo[3.2.1]oct-3-yl)-phenol

To palladium hydroxide (3.5 g, 20% w/w on carbon) was added the product of the previous step (6.9 g) in ethanol (50 mL). The slurry was stirred vigorously under a hydrogen atmosphere for 12 hours. The reaction mixture was filtered through a plug of Celite and the filtrate was concentrated to afford the title intermediate (5.6 g). (m/z): [M+H]$^+$ calcd for $C_{13}H_{17}NO$ 204.14; found 204.3.

d. Preparation of 3-endo-(3-hydroxyphenyl)-8-azabicyclo[3.2.1]octane-8-carboxylic Acid tert-butyl Ester The product of the previous step (5.6 g) was dissolved in tetrahydrofuran (75 mL) followed by the addition of N,N-diisopropylethylamine (3.6 mL). To the stirring solution, di-tert-butyl dicarbonate (5.4 g) dissolved in THF (20 mL) was added dropwise and the reaction was stirred for 1 hour. The reaction was quenched with methanol, concentrated under vacuum, diluted with dichloromethane (100 mL) and washed with 1.0 N HCl (100 mL), followed by saturated aqueous sodium chloride (100 mL). The organic layer was treated with anhydrous sodium sulfate and the solvent was dried under vacuum. The crude product was purified by flash chromatography (and eluted with 20% ethyl acetate in hexanes) to yield crude title intermediate (3.4 g). The resulting solid was dissolved with ethyl acetate (10 mL) and heated to 50° C., followed by the addition of heptane (50 mL). The solution was allowed to cool to room temperature over 2 hours. The resulting crystals were filtered to give the title intermediate (2.2 g).

e. Synthesis of 3-endo-(8-aza-bicyclo[3.2.1]oct-3-yl)-phenol 3-endo-(3-Hydroxyphenyl)-8-azabicyclo[3.2.1]octane-8-carboxylic acid tert-butyl ester (2.5 g) was treated with dichloromethane (10 mL) and TFA (10 mL) at room temperature for 10 minutes. The reaction mixture was concentrated, co-evaporated with ethyl acetate four times to give a white solid, and dried under vacuum to give the title compound as its TFA salt (3.5 g). (m/z): [M+H]$^+$ calcd for $C_{13}H_{17}NO$ 204.14; found 204.3.

Preparation 5: Synthesis of 3-endo-(8-azabicyclo[3.2.1]oct-3-yl)benzamide a. Preparation of 8-benzyl-3-exo-(3-bromophenyl)-8-azabicyclo[3.2.1]octan-3-ol To a solution of 1,3-dibromobenzene (7.4 g, 31.3 mmol) in anhydrous THF (80 mL) at −78° C. under nitrogen was added a solution of 1.6M n-butyllithium in hexanes (20 mL, 31.4 mmol) dropwise. The resulting mixture was stirred at −78° C. for 30 minutes before a solution of 8-benzyl-8-azabicyclo[3.2.1]octan-3-one (4.5 g, 20.9 mmol) in anhydrous THF (20 mL) was added dropwise. The reaction mixture was allowed to slowly warm to −40° C. over one hour and then to room temperature over 30 minutes. The reaction was quenched with saturated aqueous NH$_4$Cl and extracted with ethyl acetate. The organic layer was washed with brine, dried over sodium sulfate, filtered, concentrated, and further purified by flash chromatography. The product was eluted with 20% (300 mL) to 30% (600 mL) ethyl acetate/hexanes. Desired fractions were combined and concentrated to give the title intermediate as a yellowish oil (6.1 g). (m/z): [M+H]$^+$ calcd for $C_{20}H_{22}BrNO$ 372.10; found 372.3, 374.2 (isotope).

b. Preparation of 3-exo-(8-benzyl-3-hydroxy-8-azabicyclo[3.2.1]oct-3-yl)-benzonitrile To a solution of the product of the previous step (6.1 g, 16.4 mmol) in anhydrous DMF (82 mL) was added zinc cyanide (2.89 g, 24.6 mmol). The suspension was degassed and flushed with nitrogen before tetrakis(triphenylphosphine)palladium(0) (2.84 g, 2.5 mmol) was added. The resulting reaction mixture was then heated to 85° C. under a nitrogen atmosphere overnight. The reaction mixture was cooled to room temperature, filtered through Celite and rinsed with ethyl acetate. The organic layer was then washed with water three times. The aqueous layer was back extracted with ethyl acetate. The organic layers were combined and concentrated to about 25 mL and then extracted four times with aqueous 1N HCl. Combined aqueous layers were back extracted with diethyl ether twice and then basified to pH 10 with NaOH (pellet). The basic solution was extracted three times with ethyl acetate. The organic layers were combined and washed with brine, dried over Na$_2$SO$_4$, filtered and concentrated to give the title intermediate as a yellowish oil (4.0 g). (m/z): [M+H]$^+$ calcd for $C_{21}H_{22}N_2O$ 319.18; found 319.3.

c. Preparation of 3-exo-(8-benzyl-3-hydroxy-8-azabicyclo[3.2.1]oct-3-yl)-benzamide To a solution of 3-exo-(8-benzyl-3-hydroxy-8-azabicyclo[3.2.1]oct-3-yl)-benzonitrile (3.74 g, 11.76 mmol) in DMSO (80 mL) at room temperature was added potassium carbonate (243 mg) followed by 30% aqueous hydrogen peroxide (6 mL) dropwise. The reaction progress was monitored by mass spectrometry. After about 2.5 hr, the reaction was complete. The reaction was quenched with water (140 mL). The aqueous layer was extracted three times with ethyl acetate. The organic layers were combined and washed with half saturated brine (5×40 mL) or until an iodine starch test strip indicated no remaining peroxide. The organic layer was washed with brine, dried over sodium sulfate, filtered, and concentrated to give the title intermediate as a white solid (3.15 g). (m/z): [M+H]$^+$ calcd for $C_{21}H_{24}N_2O_2$ 337.19; found 337.3.

d. Preparation of 3-(8-benzyl-8-azabicyclo[3.2.1]oct-2-en-3-yl)benzamide

The product of the previous step (3.15 g) was treated with TFA (30 mL) at 75° C. for four hours. After concentration, the residue was dissolved in 50% acetic acid in water (15 mL), filtered, and purified by reversed phase preparative HPLC to give the TFA salt of the title intermediate as a white solid. (m/z): [M+H]$^+$ calcd for $C_{21}H_{22}N_2O$ 319.18; found 319.3.

e. Synthesis of 3-endo-(8-azabicyclo[3.2.1]oct-3-yl)-benzamide

The TFA salt of 3-endo-(8-benzyl-8-azabicyclo[3.2.1]oct-2-en-3-yl)benzamide (3.0 g) was dissolved in ethanol (50 mL) at room temperature and treated with palladium hydroxide on carbon (50 wt % water, 20% Pd on dry base, 300 mg). The resulting suspension was degassed and flushed with nitrogen three times and then exposed to a hydrogen atmosphere overnight. The reaction mixture was filtered through Celite and rinsed with ethanol. The filtrate was concentrated to give a light yellowish oil which turned into a foam upon drying under vacuum to give the title compound as its TFA salt (2.2 g). (m/z): [M+H]$^+$ calcd for $C_{14}H_{18}N_2O$ 231.15; found 231.3.

Preparation 6: Synthesis of 3-endo-[8-(2-benzylaminoethyl)-8-aza-bicyclo[3.2.1]oct-3-yl]benzamide a. Preparation of 3-endo-[8-(2,2-dimethoxyethyl)-8-azabicyclo[3.2.1]oct-3-yl]-benzamide To a solution of the TFA salt of 3-endo-(8-azabicyclo [3.2.1]oct-3-yl)-benzamide, prepared according to the method of Preparation 5 (1.03 g, 2.98 mmol) in dichloromethane (15.0 mL) at room temperature was added N,N-diisopropylethylamine (385 mg, 2.98 mmol) followed by 2,2-dimethoxy-acetaldehyde (621 mg, 5.96 mmol) and sodium triacetoxyborohydride (821 mg, 3.87 mmol). The resulting mixture was sonicated to aid dissolution. After about 30 minutes, the reaction was concentrated. The resulting residue was co-evaporated with methanol twice and then dissolved in 50% acetic acid in water (10 mL), filtered and purified by reverse phase preparative HPLC to give the title intermediate as its TFA salt (577 mg). (m/z): [M+H]$^+$ calcd for $C_{18}H_{26}N_2O_3$ 319.20; found 319.3.

b. Preparation of 3-endo-[8-(2-oxo-ethyl)-8-azabicyclo[3.2.1]oct-3-yl]benzamide

The product of the previous step (577 mg) was treated with 6N HCl (20 mL) at room temperature overnight. The reaction mixture was concentrated and the residue was diluted with water and freeze dried to give the title intermediate as its HCl salt (554 mg). (m/z): [M+H]$^+$ calcd for $C_{16}H_{20}N_2O_2$ 273.16; found 273.1.

c. Synthesis of 3-endo-[8-(2-benzylaminoethyl)-8-azabicyclo[3.2.1]oct-3-yl]-benzamide To a slurry of the HCl salt of 3-endo-[8-(2-oxo-ethyl)-8-azabicyclo [3.2.1]oct-3-yl]benzamide (220 mg, 0.71 mmol) in a mixture of dichloromethane (3 mL) and DMF (1 mL) at room temperature was added sodium triacetoxyborohydride (196 mg, 0.92 mmol) followed by benzylamine (91 mg, 0.85 mmol) and N,N-diisopropylethylamine (92 mg, 0.71 mmol). Thirty minutes later, mass spectrometry (electron spray) indicated the reaction was complete. The reaction mixture was diluted with dichloromethane. The organic layer was washed with saturated sodium bicarbonate and then brine, filtered and concentrated. The residue was redissolved in 50% acetic acid in water (10 mL), filtered and purified by reverse phase preparative HPLC to give the title compound as its bis TFA salt (27 mg). (m/z): [M+H]$^+$ calcd for $C_{23}H_{29}N_3O$ 364.24; found 364.3.

Preparation 7: Synthesis of 3-endo-{8-[2-(cyclohexylmethylamino)ethyl]-8-azabicyclo[3.2.1]oct-3-yl}benzamide To a solution of the HCl salt of 3-endo-[8-(2-oxo-ethyl)-8-azabicyclo[3.2.1]oct-3-yl]benzamide (554 mg, 1.80 mmol) in dichloromethane (9.0 mL) at 0° C. was added sodium triacetoxyborohydride (496 mg, 2.34 mmol) followed by cyclohexyl methylamine (244 mg, 2.16 mmol) and N,N-diisopropylethylamine (233 mg, 1.80 mmol). The ice-water cooling bath was removed after addition and the reaction was allowed to warm to room temperature and stirred at that temperature for one hour. The reaction mixture was then concentrated. The residue was redissolved in 50% acetic acid in water (10 mL), filtered, and purified by reverse phase preparative HPLC to give the title compound as its bis TFA salt (400 mg). (m/z): [M+H]$^+$ calcd for $C_{23}H_{35}N_3O$ 370.29; found 370.5.

Preparation 8: Synthesis of cyclohexylmethyl-(2-oxo-ethyl)carbamic Acid tert-butyl Ester a. Preparation of 2-(cyclohexylmethylamino)ethanol A mixture of cyclohexylmethylbromide (23.2 g, 131 mmol) and ethanolamine (47.9 g, 786 mmol) in EtOH (131 mL) was heated at 75° C. for 2 hours. NMR analysis of an aliquot showed the reaction was complete. The reaction was then concentrated to remove ethanol and the resulting residue was diluted with DCM. The organic layer was washed successively with water (3×100 mL) and brine (100 mL) and then dried over sodium sulfate, filtered, and concentrated to give the title intermediate as a light yellowish oil (10.57 g). (m/z): [M+H]$^+$ calcd for $C_9H_{19}NO$ 158.16; found 158.2. $^1$H NMR (CDCl$_3$, 300 MHz) δ (ppm): 3.59 (t, J=5.4 Hz, 2H), 2.73 (t, J=5.4 Hz, 2H), 2.42 (d, J=6.6 Hz, 2H), 1.6-1.77 (m, 6H), 1.36-1.6 (m, 1H), 1.10-1.28 (m, 2H), 0.82-0.95 (m, 2H).

b. Preparation of cyclohexylmethyl-(2-hydroxyethyl) carbamic Acid tert-butyl Ester To the solution of the product of the previous step (10.57 g, 67.3 mmol) in DCM (200 mL) at 0° C. was added a solution of di-tert-butyldicarbonate (13.2 g, 60.57 mmol) in DCM (100 mL) dropwise. The resulting mixture was allowed to slowly warm to room temperature overnight. The mixture was washed successively with 1N aq HCl (3×100 mL), saturated sodium bicarbonate (100 mL) and brine (100 mL). After drying over sodium sulfate, the organic layer was filtered and concentrated to give the title compound as a light yellowish oil (16.5 g). $^1$H NMR (CDCl$_3$, 300 MHz) δ (ppm): 3.71-3.73 (m, 2H), 3.37 (brs, 2H), 3.03-3.05 (m, 2H), 1.61-1.72 (m, 6H), 1.3-1.5 (m, 1H), 1.48 (s, 9H), 1.14-1.21 (m, 2H), 0.86-0.91 (m, 2H).

c. Synthesis of cyclohexylmethyl-(2-oxo-ethyl)carbamic Acid tert-butyl Ester

To the product of the previous step (16.5 g, 64.2 mmol) in DCM (256 mL) at 0° C. was added sequentially dimethylsulfoxide (7.52 g, 96.3 mmol), N,N-diisopropylethylamine (20.74 g, 160.5 mmol) and pyridine sulfur trioxide complex (25.5 g, 160.5 mmol). Thirty minutes later, NMR analysis of an aliquot showed the reaction was complete. The mixture was then washed successively with 1N aq HCl (3×100 mL), saturated sodium bicarbonate and brine, filtered through a pad of silica gel and eluted with DCM. After concentration, the title compound was obtained as a light yellowish oil (10.46 g). $^1$H NMR (CDCl$_3$, 300 MHz) δ (ppm): 9.55 (s, 1H), 3.88 (s, 1H), 3.79 (s, 1H), 3.07-3.15 (m, 2H), 1.56-1.72 (m, 6H), 1.3-1.5 (m, 1H), 1.4 (s, 9H), 1.1-1.25 (m, 2H), 0.87-0.98 (m, 2H).

Preparation 9: Synthesis of 3-endo-{8-[2-(cyclohexylmethylamino)ethyl]-8-azabicyclo[3.2.1]oct-3-yl}benzamide a. Preparation of {2-[3-endo-(3-carbamoylphenyl)-8-azabicyclo[3.2.1]oct-8-yl]-ethyl}cyclohexylmethyl-carbamic Acid tert-butyl Ester To a stirred solution of 3-endo-(8-azabicyclo[3.2.1]oct-3-yl)benzamide (1.16 g, 5.0 mmol) prepared according to the process sequence of Preparation 13, in DCM (20 mL) at 0° C. was added a solution of cyclohexylmethyl-(2-oxo-ethyl)-carbamic acid tert-butyl ester (1.53 g, 6.0 mmol) in DCM (5 mL) followed by sodium triacetoxyborohydride (1.27 g, 6.0 mmol). The resulting mixture was warmed to room temperature after addition and stirred at that temperature for 30 minutes until reaction was determined by mass spectrometry to be complete. The mixture was then diluted with DCM, washed twice with saturated sodium bicarbonate, followed by brine, dried over sodium sulfate, filtered and concentrated to give a yellowish oil, which was used in the next step without further purification. (m/z): [M+H]$^+$ calcd for $C_{28}H_{43}N_3O_3$ 470.34; found 470.6.

b. Synthesis of 3-endo-{8-[2-(cyclohexylmethylamino)ethyl]-8-azabicyclo[3.2.1]oct-3-yl}benzamide The oily residue of the previous step was dissolved in DCM (12 mL) and treated with TFA (12 mL) at room temperature for about 40 minutes. The reaction was judged complete by mass spectrometry. The mixture was then concentrated and co-evaporated three times with ethyl acetate, diluted with DCM and basified to pH 8.0 with saturated sodium bicarbonate. The layers were separated and aqueous layer was extracted with DCM one more time. The combined organic layer was then washed with brine, dried over sodium sulfate, filtered, and concentrated to give a brownish oil. Further drying under vacuum provided a light brownish foam (1.34 g). (m/z): [M+H]$^+$ calcd for $C_{23}H_{35}N_3O$ 370.29; found 370.4. $^1$H NMR (CDCl$_3$, 300 MHz) δ (ppm): 7.89 (s, 1H), 7.70-7.72 (m, 1H), 7.54-7.56 (m, 1H), 7.39-7.44 (m, 1H), 3.43 (brs, 2H), 3.16-3.21 (m, 1H), 3.06-3.10 (m, 2H), 2.91 (d, J=7.2 Hz, 2H), 2.65-2.69 (m, 2H), 2.05-2.51 (m, 2H), 2.01-2.05 (m, 2H), 1.79-1.91 (m, 8H) 1.60-1.63 (m, 2H), 1.27-1.42 (m, 3H), 1.09-1.17 (m, 2H).

Preparation 10: Synthesis of (2-oxo-ethyl)-(4-trifluoromethylbenzyl)-carbamic Acid tert-butyl Ester a. Preparation of 2-(4-trifluoromethylbenzylamino)ethanol Following the method of Preparation 8, step a, 4-trifluoromethylbenzyl bromide (664 mg, 2.78 mmol) was heated with ethanolamine (1.02 g, 16.7 mmol) in ethanol (3 mL) at 75° C. overnight. The product was isolated to give the title intermediate as a yellowish oil (585 mg). (m/z): [M+H]$^+$ calcd for $C_{10}H_{12}F_3NO$ 220.10; found 220.3. $^1$H NMR (CDCl$_3$, 300 MHz) δ (ppm): 7.59 (d, J=7.8 Hz, 2H), 7.45 (d, J=7.8 Hz, 2H), 3.88 (s, 2H), 3.66-3.70 (m, 2H), 2.80-2.83 (m, 2H).

b. Preparation of (2-hydroxyethyl)-(4-trifluoromethylbenzyl)carbamic Acid tert-butyl Ester Following the method of Preparation 8, step b, the product of the previous step (585 mg, 2.65 mmol) was treated with di-tert-butyl dicarbonate (525 mg, 2.41 mmol) to give the title intermediate as a light yellowish oil (796 mg). $^1$H NMR (CDCl$_3$, 300 MHz) δ (ppm): 7.57 (d, J=7.8 Hz, 2H), 7.32 (d, J=7.8 Hz, 2H), 4.52 (brs, 2H), 3.71 (brs, 2H), 3.40 (brs, 2H), 1.44 (brs, 9H).

c. Synthesis of (2-oxo-ethyl)-(4-trifluoromethylbenzyl)carbamic Acid tert-butyl Ester Following the method of Preparation 8, step c, the product of the previous step (796 mg, 2.49 mmol) was oxidized with sulfur trioxide pyridine complex (990 mg, 6.22 mmol) to give the title compound as a light yellowish oil (538 mg).

Preparation 11: Synthesis of 3-endo-{8-[2-(4-trifluoromethylbenzylamino)ethyl]-8-azabicyclo[3.2.1]oct-3-yl}phenol a. Preparation of {2-[3-endo-(3-hydroxyphenyl)-8-azabicyclo[3.2.1]oct-8-yl]ethyl}-(4-trifluoromethylbenzyl)carbamic Acid tert-butyl Ester Following the method of Preparation 9, step a, (2-oxo-ethyl)-(4-trifluoromethyl-benzyl)carbamic acid tert-butyl ester (253 mg, 1.84 mmol) was reacted with the TFA salt of 3-endo-(8-aza-bicyclo[3.2.1]oct-3-yl)-phenol, prepared by the method of Preparation 4 (126 mg, 0.92 mmol) to give the title intermediate as a yellowish oil, which was used directly in the next step.

b. Synthesis of 3-endo-{8-[2-(4-trifluoromethylbenzylamino)ethyl]-8-azabicyclo[3.2.1]oct-3-yl}phenol Following the method of Preparation 9, step b, the product of the previous step was treated with TFA (1.5 mL) and dichloromethane (1.5 mL) and purified by reverse phase preparative HPLC to give the title compound as its bis TFA salt (142 mg). (m/z): M+H]$^+$ calcd for $C_{23}H_{27}F_3N_2O$ 405.2. $^1$H NMR (CD$_3$OH, 300 MHz) δ (ppm): 7.75 (d, J=7.8 Hz, 2H), 7.68 (d, J=7.8 Hz, 2H), 7.11-7.16 (m, 1H), 6.91-6.94 (m, 1H), 6.87 (s, 1H), 6.62-6.65 (m, 1H), 4.34 (s, 2H), 4.04 (brs, 2H), 3.52 (t, J=6.3 Hz, 2H), 3.31-3.39 (m, 2H), 3.13-3.20 (m, 1H, 2.52-2.59 (m, 4H), 2.02-2.06 (m, 2H), 1.87-1.90 (m, 2H).

Preparation 12: Synthesis of 3-endo-(8-azabicyclo[3.2.1]oct-3-yl)-benzamide a. Preparation of 8-benzyl-3-(3-methoxyphenyl)-8-azabicyclo[3.2.1]oct-2-ene To a 500 mL flask fitted with a magnetic stir bar was added 8-benzyl-3-exo-(3-methoxy-phenyl)-8-azabicyclo[3.2.1]octan-3-ol (21.44 g, 66.2 mmol) followed by acetic anhydride (150 mL). Ytterbium triflate (20.51 g, 33.1 mmol) was added as a solid, and the reaction solidified. Additional acetic anhydride (100 mL) was added to suspend the solid. The reaction was then heated to 60° C. for 4 hours. The stirring was stopped and the reaction was diluted with ethyl acetate and quenched carefully with 1N NaOH. The organic layer was washed with brine then dried over magnesium sulfate. Solvent was removed in vacuo to give the title intermediate as a sticky yellow oil (9.9 g, 48% yield). (m/z): [M+H]$^+$ calcd for $C_{21}H_{23}NO$ 306.19; found 306.3.

b. Preparation of 3-endo-(3-methoxyphenyl)-8-azabicyclo[3.2.1]octane

To a small Parr flask containing the product of the previous step (9.9 g, 32.5 mmol) was added ethanol (70 mL). The mixture was stirred at room temperature until the reactant was fully dissolved. To the solution was added palladium hydroxide (4.45 g, ~50 wt %) as a solid, portionwise, with care. The reaction vessel was purged with dry nitrogen and placed under a hydrogen atmosphere (55 psi) overnight. When the reaction was complete by HPLC, the reaction was purged with nitrogen and filtered through Celite. The solvent was removed in vacuo to give the title intermediate as a yellow oil (6.9 g, 98% yield). (m/z): [M+H]$^+$ calcd for $C_{14}H_{19}NO$ 218.16; found 218.3.

c. Preparation of 3-endo-(8-azabicyclo[3.2.1]oct-3-yl)-phenol

To a 1-L round bottom flask fitted with a magnetic stirbar was added the product of the previous step (6.9 g, 31.79 mmol) and dichloromethane (200 mL). The reaction was cooled in a dry ice/acetone bath to −78° C. for 15 minutes. To the cooled reaction was added boron tribromide as a 1M solution in dichloromethane (64 mL, 63.59 mmol) quickly. The reaction was permitted to warm slowly to room temperature over a period of 20 hours. Methanol was carefully added to quench the reaction. The stir bar was removed and the solvent was removed in vacuo to give a crunchy brown solid. The solid was dissolved in methanol. The solvent was removed in vacuo to give a crunchy brown solid. The solid was dissolved again in methanol. The solvent was removed in vacuo to give a crunchy brown solid which was then dried under vacuum. The dried solid was then dissolved in dichloromethane and the solution was washed with 1N NaOH and saturated sodium chloride solution. The organic layer was separated and dried over anhydrous sodium sulfate. Solvent was removed in vacuo to afford the title intermediate as a yellow oil. (m/z): [M+H]$^+$ calcd for $C_{13}H_{17}NO$ 204.14; found, 204.3.

d. Preparation of 3-endo-(3-hydroxyphenyl)-8-azabicyclo[3.2.1]octane-8-carboxylic Acid tert-butyl Ester To a 500 mL reaction flask containing 3-endo-(8-azabicyclo[3.2.1]oct-3-yl)-phenol (2.5 g, 12.3 mmol) was added dichloromethane (100 mL) under a dry nitrogen atmosphere and then tetrahydrofuran (70 mL). To the slurry was then added N,N-diisopropylethylamine (3 mL) and di-tert-butyl dicarbonate (3 mL, 12.3 mmol) in one portion as a melted liquid. The reaction was allowed to stir at room temperature over a period of 16 hours. When the reaction was complete by HPLC, the reaction mixture was transferred to a larger flask and most of the solvent was removed. The remaining residue was dissolved in ethyl acetate and the organic layer was washed with saturated aqueous sodium bicarbonate and saturated aqueous sodium chloride. The organic layer was dried over anhydrous magnesium sulfate and solvent was removed in vacuo to yield crude title intermediate. The crude material was chromatographed on silica gel using 20-25% ethyl acetate/hexanes as the mobile phase. Fractions were combined and solvent was removed in vacuo to give 2.4 g of purified product. The purified material was dissolved in dichloromethane (~10 mL) and hexanes (150 mL) were added. Dichloromethane was removed by rotary evaporation. The solution was transferred to an Erlenmeyer flask and some seed crystals from a previous preparation by the same method were added. The solution was left to crystallize overnight. Crystals were isolated via filtration and washed with hexanes. Drying under vacuum gave the title intermediate as white needles (1.01 g, 27% yield). The mother liquor began to grow crystals, which were harvested, collected, washed with hexanes, and dried under vacuum to give the title intermediate as white needles (850 mg, 23% yield). (m/z): [M+H]$^+$ calcd for $C_{18}H_{25}NO_3$ 304.19; found 304.3, 248.3 (parent—tert-butyl).

e. Preparation of 3-endo-(3-trifluoromethanesulfonyloxy-phenyl)-8-aza-bicyclo[3.2.1]octane-8-carboxylic Acid tert-butyl Ester To a 50 mL reaction flask fitted with a magnetic stirbar and purged with dry nitrogen was added 3-endo-(3-hydroxyphenyl)-8-azabicyclo[3.2.1]octane-8-carboxylic acid tert-butyl ester (587 mg, 1.94 mmol) and dimethylformamide (10 mL). The reaction was stirred until a solution formed, then potassium carbonate (0.40 g, 2.90 mmol) and N-phenyltrifluoromethanesulfonimide (1.03 g, 2.90 mmol) were added together as solids in one portion. The reaction was heated to 50° C. overnight. The reaction was diluted with 1:1 ethyl acetate:hexanes and water and the organic layer was washed with brine and dried over anhydrous magnesium sulfate. Solvent was removed in vacuo to give the title intermediate as a colorless oil (856 mg, >100% yield). (m/z): [M+H]$^+$ calcd for $C_{19}H_{24}F_3NO_5S$ 436.14; found 436.2, 380.3 (parent—tert-butyl).

f. Preparation of 3-endo-(3-cyanophenyl)-8-azabicyclo[3.2.1]octane-8-carboxylic Acid tert-butyl Ester To a 1 L round bottom flask fitted with a magnetic stirbar and purged with dry nitrogen was added 3-endo-(3-trifluoromethanesulfonyloxy-phenyl)-8-aza-bicyclo[3.2.1]octane-8-carboxylic acid tert-butyl ester (38.4 g, 88.3 mmol) and dimethylformamide (320 mL). The solution was stirred for 5 minutes to dissolve all starting material, then degassed under vacuum. A dry nitrogen atmosphere was again introduced. To the degassed solution was added zinc cyanide (15.5 g, 132 mmol) and tetrakis(triphenylphosphine)palladium (0) (5.1 g, 4.41 mmol) together as solids in one portion. The reaction was again degassed under vacuum to remove incidental oxygen, and a dry nitrogen atmosphere was introduced. The reaction was heated to 80° C. for 4 hours. The reaction was cooled to room temperature and diluted with isopropyl acetate (500 mL). The resulting cloudy solution was filtered through Celite (10 g). The resulting organic solution was transferred to a separatory funnel and washed with saturated aqueous sodium bicarbonate (400 mL) and saturated aqueous sodium chloride (400 mL). The organic layer was separated and dried over anhydrous sodium sulfate (30 g). Drying agent was removed via filtration and solvent was removed in vacuo to give crude title intermediate as waxy brown crystals (29.9 g, >100% yield). (m/z): [M+H]$^+$ calcd for $C_{19}H_{24}N_2O_2$ 313.19; found 313.3, 257.3 (parent—tert-butyl).

g. Synthesis of 3-endo-(8-azabicyclo[3.2.1]oct-3-yl)-benzamide 3-endo-(3-Cyanophenyl)-8-aza-bicyclo[3.2.1]octane-8-carboxylic acid tert-butyl ester (4.8 g, 15.36 mmol) was weighed into a 500 mL round bottom flask and diluted with DMSO (105 mL). Potassium carbonate (3.18 g, 23.04 mmol) was added as a solid followed by 30% hydrogen peroxide in water (8 mL) carefully behind a blast shield. The reaction was stirred open to air overnight at room temperature. When the reaction was complete by HPLC, water (160 mL) was added and the reaction was extracted into ethyl acetate (3×150 mL). Combined organic layers were washed with sodium sulfite (all aqueous layers were quenched for peroxide with sodium sulfite) and brine and dried over sodium sulfate. Solvent was removed in vacuo to give the protected intermediate 3-(3-carbamoylphenyl)-8-aza-bicyclo[3.2.1]octane-8-carboxylic acid tert-butyl ester as a colorless oil (4.8 g, 95% yield). (m/z): [M+H]$^+$ calcd for $C_{19}H_{26}N_2O_3$ 331.20; found 331.4, 275.0 (parent—tert-butyl).

The protected intermediate is treated with dichloromethane and trifluoroacetic acid according to the method of Preparation 4, step e to provide the TFA salt of the title compound.

Preparation 13: Synthesis of 3-endo-(8-azabicyclo[3.2.1]oct-3-yl)-benzamide a. Preparation of 8-benzyl-3-exo-(3-methoxyphenyl)-8-azabicyclo[3.2.1]octan-3-ol To a 3 L-3-necked flask fitted with an overhead stirrer and flushed with dry nitrogen was added cerous chloride powder (88.2 g, 0.35 mol). The solid was diluted with anhydrous tetrahydrofuran (500 mL) and cooled to 0° C. To the suspension was added 1M 3-methoxyphenyl magnesium bromide in THF (360 mL, 0.36 mol) dropwise while the temperature was maintained below 10° C. The resulting solution was stirred at 0° C. for 1.5 hours. A solution of 8-benzyl-8-aza-bicyclo[3.2.1]octan-3-one (54.5 g, 0.25 mol) in tetrahydrofuran (50 mL) was then added dropwise, while maintaining the internal temperature below 5° C. The resulting solution was stirred at 0° C. for 2 hours. The reaction was quenched with 10% aqueous acetic acid (400 mL) and stirred for 30 minutes at room temperature. Saturated sodium chloride solution (400 mL) was then added and the resulting suspension was stirred at room temperature for 20 hours to allow complete crystallization of product as the acetate salt. The crystals were filtered and washed with cold water (200 mL) followed by isopropyl acetate (200 mL) and dried under vacuum to give the title intermediate as a white crystalline powder (91.1 g, 93% yield). (m/z): [M+H]$^+$ calcd for $C_{21}H_{25}NO_2$ 324.20; found, 324.5.

b. Preparation of 8-benzyl-3-(3-methoxyphenyl)-8-azabicyclo[3.2.1]oct-2-ene To a 1 L flask fitted with a magnetic stir bar was added 8-benzyl-3-exo-(3-methoxy-phenyl)-8-azabicyclo[3.2.1]octan-3-ol as the acetate salt (80.4 g, 0.209 mol) followed by 6M aqueous hydrochloride acid (300 mL). The reaction was heated to 70° C. for 2 hours. The stirring was stopped and the reaction was diluted with dichloromethane (200 mL). The mixture was transferred to a separatory funnel and the layers were mixed, then allowed to settle. The organic layer was removed and saved. The aqueous layer was extracted with dichloromethane (2×200 mL). The combined organic layers were washed with saturated aqueous sodium chloride solution (400 mL) and dried over anhydrous sodium sulfate (30 g). Solvent was removed in vacuo to give the hydrochloride salt of the title intermediate as a sticky yellow oil (65.4 g, 91% yield). (m/z): [M+H]$^+$ calcd for $C_{21}H_{23}NO$ 306.19; found 306.3.

c. Preparation of 3-endo-(3-methoxyphenyl)-8-azabicyclo[3.2.1]octane

To a 1 L round-bottom flask containing of the product of the previous step (65.4 g, 0.191 mol) was added ethanol (300 mL). The mixture was stirred at room temperature until the intermediate was fully dissolved. To the solution was added palladium hydroxide (6.7 g, ~10 wt %) as a solid, portionwise, with care. The reaction vessel was purged with dry nitrogen and hydrogen was introduced carefully via balloon and needle. The hydrogen was bubbled through the solution for 10 minutes, and the solution was allowed to stir overnight under a hydrogen atmosphere. When the reaction was complete by HPLC, the hydrogen was removed from the reaction mixture and the vessel was purged with dry nitrogen for 10 minutes. The reaction was then filtered through Celite (5 g), and the Celite cake was washed with ethanol (100 mL). The combined ethanol solution was evaporated in vacuo, and the resulting residue was dissolved in dichloromethane (400 mL). The organic layer was washed with 3N sodium hydroxide (300 mL). The layers were separated and the aqueous layer was extracted with dichloromethane (2×200 mL). Combined organic layers were washed with aqueous sodium chloride (300 mL) and dried over potassium carbonate (30 g). The drying agent was removed via filtration and solvent was removed in vacuo to give the title intermediate as a yellow oil (27.6 g, 66% yield). (m/z): [M+H]$^+$ calcd for $C_{14}H_{19}NO$ 218.16; found 218.3.

d. Preparation of 3-endo-(8-azabicyclo[3.2.1]oct-3-yl)-phenol

To a 1-L round bottom flask fitted with a magnetic stirbar and an addition funnel was added the product of the previous step (27.6 g, 0.127 mol) and dichloromethane (300 mL). The reaction was cooled in a dry ice/acetone bath to −78° C. To the cooled reaction was added boron tribromide (1M solution in dichloromethane, 152 mL, 0.152 mol). The reaction was permitted to warm slowly to room temperature over a period of 20 hours. The reaction was placed on an ice bath and methanol (100 mL) was carefully added to quench the reaction. The solvent was removed in vacuo to give a crunchy beige solid. The solid was redissolved in methanol (100 mL). The solvent was removed in vacuo to give a crunchy beige solid. The solid was redissolved again in methanol (100 mL). The solvent was removed in vacuo to give a crunchy beige solid which was then dried under vacuum for 2 hours. The dried solid was then suspended in ethanol (110 mL) and the solution was heated on an oil bath to 80° C. To the hot solution was added just enough methanol to dissolve all the solid material (72 mL). The solution was cooled slowly to room temperature, and white crystals of the hydrobromide salt of the title intermediate were allowed to form. The solution was then further cooled to −20° C. in the freezer for one hour. The crystallization was warmed to room temperature and the crystals were collected via filtration. The white crystals were washed with cold ethanol (35 mL) and dried under house vacuum to give the hydrobromide salt of the title intermediate as a white powder (19.5 g, 54% yield). The mother liquor was evaporated to give a crunchy beige solid. The solid was redissolved in ethanol (30 mL) and heated to 80° C. A clear brown solution formed. The solution was cooled to room temperature and then to −20° C. for one hour. Crystals were then collected via filtration, washed with cold ethanol (10 mL), and dried under vacuum to give a second crop of crystals (5.5 g, 15% yield). (m/z): [M+H]$^+$ calcd for $C_{13}H_{17}NO$ 204.14; found, 204.4.

e. Preparation of 3-endo-(3-hydroxyphenyl)-8-azabicyclo[3.2.1]octane-8-carboxylic Acid tert-butyl Ester To a 500 mL reaction flask containing the hydrobromide salt of 3-endo-(8-azabicyclo[3.2.1]oct-3-yl)-phenol (24.8 g, 0.087 mol) was added dichloromethane (200 mL) under a dry nitrogen atmosphere. The slurry was cooled to 0° C. To the slurry was then added N,N-diisopropylethylamine (22.75 mL, 0.13 mol) and di-tert-butyl dicarbonate (19.03 g, 0.087 mol) in one portion as a solid. The reaction was allowed to warm to room temperature over a period of 16 hours. When the reaction was complete by HPLC, the reaction mixture (now a clear light brown solution) was transferred to a separatory funnel and diluted with isopropyl acetate (200 mL). The organic mixture was washed with saturated aqueous sodium bicarbonate (300 mL). The organic layer was removed and the aqueous layer was extracted with isopropyl acetate (200 mL). The combined organic layers were washed with aqueous sodium chloride solution (300 mL), the layers were separated, and the organic layer was dried over anhydrous sodium sulfate (20 g). Solvent was removed in vacuo to afford the title intermediate as a white solid (27.1 g, >100% yield). (m/z): [M+H]$^+$ calcd for $C_{18}H_{25}NO_3$ 304.19; found 304.3, 248.3 (parent—tert-butyl).

f. Preparation of 3-endo-(3-trifluoromethanesulfonyloxy-phenyl)-8-aza-bicyclo[3.2.1]octane-8-carboxylic Acid tert-butyl Ester To a 500 mL reaction flask fitted with a magnetic stirbar and purged with dry nitrogen was added the product of the previous step (27.1 g, 0.089 mol) and dichloromethane (250 mL). The solution was cooled to 0° C. on an ice bath. To the cold solution was added triethylamine (12.4 mL, 0.097 mol) and trifluoromethane sulfonyl chloride (9.43 mL, 0.097 mol) dropwise while maintaining the internal temperature below 10° C. To this reaction was added solid 4-N,N-dimethylaminopyridine (0.544 g, 4.46 mmol) in one portion. The reaction was warmed to room temperature and stirred for 30 minutes. The final solution was transferred to a separatory funnel. The organic layer was washed with saturated aqueous sodium bicarbonate (200 mL) and saturated aqueous sodium chloride (200 mL). The organic layer was separated and dried over anhydrous sodium sulfate (20 g). Drying agent was removed via filtration and solvent was removed in vacuo to yield the title intermediate as a clear oil (38.4 g, 98% yield). (m/z): [M+H]$^+$ calcd for $C_{19}H_{24}F_3NO_5S$ 436.14; found 436.2, 380.3 (parent—tert-butyl).

g. Preparation of 3-endo-(3-cyanophenyl)-8-aza-bicyclo[3.2.1]octane-8-carboxylic Acid tert-butyl Ester To a 1 L round bottom flask fitted with a magnetic stirbar and purged with dry nitrogen was added the product of the previous step (38.4 g, 88.3 mmol) and dimethylformamide (320 mL). The solution was stirred for 5 minutes to dissolve all starting material, then degassed under vacuum. A dry nitrogen atmosphere was again introduced. To the degassed solution was added zinc cyanide (15.5 g, 132 mmol) and tetrakis(triphenylphosphine)palladium (0) (5.1 g, 4.41 mmol) together as solids in one portion. The reaction was again degassed under vacuum and a dry nitrogen atmosphere was introduced. The reaction was heated to 80° C. for 4 hours. The reaction was cooled to room temperature and diluted with isopropyl acetate (500 mL). The resulting cloudy solution was filtered through Celite (10 g). The resulting organic solution was washed with saturated aqueous sodium bicarbonate (400 mL) and saturated aqueous sodium chloride (400 mL). The organic layer was separated and dried over anhydrous sodium sulfate (30 g). Drying agent was removed via filtration and solvent was removed in vacuo to give crude title intermediate as waxy brown crystals (29.9 g, >100% yield). (m/z): [M+H]$^+$ calcd for $C_{19}H_{24}N_2O_2$ 313.19; found 313.3, 257.3 (parent—tert-butyl).

h. Synthesis of 3-endo-(8-azabicyclo[3.2.1]oct-3-yl)-benzamide

To a 15 mL round bottom flask fitted with a magnetic stirbar and a reflux condenser was added 3-endo-(3-cyanophenyl)-8-aza-bicyclo[3.2.1]octane-8-carboxylic acid tert-butyl ester (500 mg, 1.60 mmol) as a solid followed by trifluoroacetic acid (4 mL). To the solution was added concentrated sulfuric acid (440 µL, 5.0 equiv.). The reaction was heated to 65° C. for 10 hours. The reaction was poured into a solution of saturated aqueous sodium chloride (70 mL) and transferred to a separatory funnel. The aqueous layer was washed with isopropyl acetate (50 mL) to remove residual triphenylphosphine oxide from the previous step. To the aqueous layer was added 3 N aqueous sodium hydroxide (15 mL) to adjust the pH to 14. The aqueous layer was extracted with tetrahydrofuran (2×50 mL). Combined organic layers were dried over anhydrous sodium sulfate (3 g). Drying agent was removed via filtration and the solvent was removed in vacuo to give the title compound as a crunchy, partially crystalline foam (300 mg, 79% yield). (m/z): [M+H]$^+$ calcd for $C_{14}H_{18}N_2O$ 231.15; found 231.2.

Preparation 14: Synthesis of methoxycarbonylmethanesulfonyl-acetic Acid a. Preparation of methoxycarbonylmethylsulfanyl-acetic Acid tert-butyl Ester To a solution of mercapto-acetic acid methyl ester (1.0 g, 9.42 mmol) in dimethylformamide (10 mL) at room temperature was added potassium carbonate (1.69 g) followed by bromo-acetic acid tert-butyl ester (1.84 g, 9.42 mmol). The resulting suspension was stirred at ambient temperature overnight and then diluted with hexanes. The organic layer was washed with water three times and brine once, dried over sodium sulfate, filtered and concentrated to give a colorless oil, which was used directly in next step without purification. $^1$H NMR (CDCl$_3$, 300 MHz) δ (ppm): 3.72 (s, 3H), 3.37 (s, 2H), 3.27 (s, 2H), 1.45 (s, 9H).

b. Preparation of methoxycarbonylmethanesulfonyl-acetic Acid tert-butyl Ester

To a solution of the product of the previous step (830 mg, 3.75 mmol) in dichloromethane (25 mL) at 0° C. was added 3-chloroperoxybenzoic acid (1.94 g, 11.25 mmol). The resulting mixture was allowed to warm to room temperature after addition and stirred at ambient temperature for 2.5 hours. The reaction was quenched with saturated sodium sulfite (30 mL) and the mixture was stirred at ambient temperature for 15 minutes. The layers were separated and the organic layer was washed sequentially with 1N aqueous NaOH, saturated sodium bicarbonate, and brine. The organic layer was dried over sodium sulfate, filtered, and concentrated to give the title intermediate as a colorless oil (683 mg), which was used directly in the next step. $^1$H NMR (CDCl$_3$, 300 MHz) δ (ppm): 4.32 (s, 2H), 4.21 (s, 2H), 3.81 (s, 3H), 1.48 (s, 9H).

c. Synthesis of methoxycarbonylmethanesulfonyl-acetic Acid

The product of the previous step (683 mg) was treated with trifluoroacetic acid (10 mL) at ambient temperature for two hours. The mixture was concentrated, redissolved in ethyl acetate and the organic layer was washed with water followed by brine. The organic layer was dried over sodium sulfate, filtered, and concentrated to give title compound as a colorless oil which turned into a wax upon drying under vacuum. (345 mg). $^1$H NMR (CDCl$_3$, 300 MHz) δ (ppm): 4.39 (s, 2H), 4.33 (s, 2H), 3.83 (s, 3H).

Preparation 15: Synthesis of (S)-2,2-dimethyl-[1,3]dioxolane-4-carboxylic Acid

To a solution of α,β-isopropylidene-1-glyceric acid methyl ester (2.2 g, 13.7 mmol) in MeOH (20 mL) at ambient temperature was added lithium hydroxide monohydrate (1.15 g, 27.4 mmol) in water (5.0 mL). The resulting mixture was stirred at ambient temperature overnight. After concentration, the residue was acidified with 10% aqueous HCl (20 mL) and then extracted with dichloromethane three times. The combined organic layer was washed with brine twice, dried over sodium sulfate, filtered and concentrated to give the title compound as a colorless oil (819 mg). $^1$H NMR (CDCl$_3$, 300 MHz) δ (ppm): 4.60 (dd, J=4.5, 7.2 Hz, 1H), 4.28 (dd, J=7.2, 8.7 Hz, 1H), 4.18 (dd, J=4.5, 8.7 Hz, 1H), 1.51 (s, 3H), 1.40 (s, 3H).

Preparation 16: Synthesis of Acetic Acid [benzyl-(2-oxo-ethyl)carbamoyl]-methyl Ester a. Synthesis of Acetic Acid [benzyl-(2-hydroxyethyl)carbamoyl]methyl Ester Benzylethanolamine (1.78 g, 11.8 mmol.) was weighed into a 25 mL round bottom flask and diluted with dichloromethane. N,N-Diisopropylethylamine (2.66 mL, 15.3 mmol) was added quickly via syringe and the reaction was cooled to 0° C. After stirring at 0° C. for 10 minutes, acetoxyacetyl chloride (1.26 mL, 11.8 mmol) was added dropwise via syringe. The reaction was stirred overnight and allowed to warm to room temperature. The reaction mixture was diluted with ethyl acetate and washed with saturated aqueous sodium bicarbonate and saturated aqueous sodium chloride. The organic layer was separated and dried over anhydrous magnesium sulfate. The drying agent was removed via filtration and solvent was removed in vacuo to give crude title intermediate as a yellow oil. The crude material was chromatographed on silica gel using ethyl acetate as the mobile phase. Fractions were combined and solvent was removed in vacuo to give pure title intermediate as a clear oil (1.75 g, 59% yield). (m/z): [M+H]$^+$ calcd for C$_{13}$H$_{17}$NO$_4$ 252.13, found 252.3.

b. Synthesis of Acetic Acid [benzyl-(2-oxo-ethyl)carbamoyl]methyl Ester

Acetic acid [benzyl-(2-hydroxyethyl)carbamoyl]methyl ester (1.28 g, 5.10 mmol) was weighed into a 200 mL round bottom flask and purged with nitrogen. Dichloromethane (50 mL) was added, and the reaction was cooled to −15° C. for 10 minutes. Dimethylsulfoxide (3.61 mL, 51.0 mmol.), N,N-diisopropylethylamine (4.43 mL, 25.5 mmol), and pyridine-sulfur trioxide complex (4.06 g, 25.5 mmol) were then added sequentially at −15° C. The reaction was allowed to warm slowly to room temperature and stirred overnight. The reaction was complete by thin layer chromatography, and was diluted with ethyl acetate. The organic solution was washed with saturated aqueous sodium bicarbonate and saturated aqueous sodium chloride. The organic layer was separated and dried over anhydrous magnesium sulfate. The drying agent was removed via filtration and solvent was removed in vacuo to give crude title compound as a yellow oil. The crude material was chromatographed on silica gel using 1:1 ethyl acetate:dichloromethane as the mobile phase. Fractions were combined and solvent was removed in vacuo to give pure title compound as a colorless oil (0.72 g, 57% yield). (m/z): [M+H]$^+$ calcd for C$_{13}$H$_{15}$NO$_4$ 250.11, found 250.0.

Preparation 17: Synthesis of 3-endo-[8-(2-phenethylaminoethyl)-8-aza-bicyclo[3.2.1]oct-3-yl]benzamide a. Preparation of 2-phenethylaminoethanol A mixture of 2-bromoethyl benzene (2.0 g, 10.8 mmol) and ethanolamine (3.96 g, 64.8 mmol) in ethanol (11 mL) was heated at 75° C. for 16.5 hours at which time LC/MS showed the reaction was complete. The reaction mixture was then concentrated to remove ethanol and the resulting residue was diluted with DCM (100 mL). The organic layer was partitioned with water (100 mL) and the aqueous layer was extracted with DCM (50 mL). The combined organic layers were washed with water (2×5 mL), dried over sodium sulfate, filtered, and concentrated to give the title intermediate as a light yellowish oil (1.5 g). (m/z): [M+H]$^+$ calcd for C$_{10}$H$_{15}$NO, 166.13; found, 166.2) $^1$H NMR (d$_6$-DMSO, 300 MHz) δ (ppm): 7.13-7.29 (m, 5H), 4.4 (br, 1H), 3.42 (t, J=5.7 Hz, 2H), 2.61-2.76 (m, 4H), 2.55-2.59 (t, J=5.7 Hz, 2H), 1.55 (br, 1H).

b. Preparation of (2-hydroxyethyl)phenethylcarbamic Acid tert-butyl Ester

Following the procedure of Preparation 8 step b, the product of the previous step (1.5 g, 9.09 mmol) was reacted with di-tert-butyl dicarbonate (1.78 g, 8.2 mmol) in DCM (14 mL) to provide the title intermediate (2.26 g) as a light yellowish oil.

c. Preparation of (2-oxo-ethyl)phenethylcarbamic Acid tert-butyl Ester

Following the procedure of Preparation 8, step c, the product of the previous step (2.26 g, 8.5 mmol) was converted to the title intermediate, which was obtained as a yellowish oil (1.27 g) $^1$H NMR (d$_6$-DMSO, 300 MHz) δ (ppm): 9.37 (s, 1H), 7.21-7.28 (m, 2H), 7.17-7.20 (m, 3H), 3.93 (s, 2H), 3.41 (t, 2H), 2.74 (t, 2H), 1.30 (s, 9H).

d. Preparation of {2-[3-endo-(3-carbamoylphenyl)-8-aza-bicyclo[3.2.1]oct-8-yl]-ethyl}phenethylcarbamic Acid tert-butyl Ester Following the procedure of Preparation 9 step a, 3-endo-(8-azabicyclo[3.2.1]oct-3-yl)benzamide (60 mg, 0.28 mmol), prepared by the method of Preparation 13, was reacted with (2-oxo-ethyl)phenethylcarbamic acid tert-butyl ester (87 mg, 0.34 mmol) to provide the title intermediate as a yellowish oil. (m/z): [M+H]$^+$ calcd for C$_{29}$H$_{39}$N$_3$O$_3$ 478.30; found, 478.4.

e. Preparation of 3-endo-[8-(2-phenethylamino-ethyl)-8-azabicyclo[3.2.1]oct-3-yl]-benzamide Following the procedure of Preparation 9, step b, the product of the previous step was treated with TFA to provide the title intermediate as a dark oil. (m/z): [M+H]$^+$ calcd for C$_{24}$H$_{31}$N$_3$O 378.25; found, 378.2.

Preparation 18: Synthesis of 3-endo-[8-(2-(3-phenylpropylamino)ethyl)-8-aza-bicyclo[3.2.1]oct-3-yl]benzamide Following the procedure of Preparation 17 substituting 1-bromo-3-phenylpropane for 2-bromoethyl benzene, the following intermediates were prepared:
a. 2-(3-phenylpropylamino)ethanol $^1$H NMR (d$_6$-DMSO, 300 MHz) δ (ppm): 7.14-7.28 (m, 5H), 4.4 (br, 1H), 3.42 (t, J=5.7 Hz, 2H), 2.46-2.58 (m, 6H), 1.61-1.71 (p, 2H), 1.65 (br, 1H).
b. (2-hydroxyethyl)-(3-phenylpropyl)carbamic acid tert-butyl ester
c. (2-oxo-ethyl)-(3-phenylpropyl)carbamic acid tert-butyl ester $^1$H NMR (d$_6$-DMSO, 300 MHz) δ (ppm): 9.44 (s, 1H), 7.24-7.39 (m, 2H), 7.15-7.19 (m, 3H), 3.97 (s, 2H), 3.24 (t, 2H), 2.49 (t, 2H), 1.69-1.74 (m, 2H), 1.34 (s, 9H).
d. {2-[3-endo-(3-carbamoylphenyl)-8-aza-bicyclo[3.2.1]oct-8-yl]-ethyl}-(3-phenylpropyl)carbamic acid tert-butyl ester (m/z): [M+H]$^+$ calcd for C$_{30}$H$_{41}$N$_3$O$_3$ 492.31; found, 492.4.
e. 3-endo-{8-[2-(3-phenylpropylamino)ethyl]-8-azabicyclo[3.2.1]oct-3-yl}-benzamide (m/z): [M+H]$^+$ calcd for C$_{25}$H$_{33}$N$_3$O 392.26; found, 392.4.

Preparation 19: Synthesis of 3-endo-{8-(2-(2-cyclohexylethylamino)ethyl)-8-azabicyclo[3.2.1]oct-3-yl]benzamide Following the procedure of Preparation 17 substituting 1-bromo-2-cyclohexylethane for 2-bromoethyl benzene, the following intermediates were prepared:
a. 2-(2-cyclohexylethylamino)ethanol $^1$H NMR (d$_6$-DMSO, 300 MHz) δ (ppm): 4.4 (br, 1H), 3.38-3.42 (t, J=5.7 Hz, 2H), 2.46-2.54 (m, 4H), 1.58-1.65 (m, 5H), 1.06-1.29 (m, 6H), 0.82-0.89 (m, 2H).
b. (2-cyclohexylethyl)-(2-hydroxyethyl)carbamic acid tert-butyl ester
c. (2-cyclohexylethyl)-(2-oxo-ethyl)carbamic acid tert-butyl ester $^1$H NMR (d$_6$-DMSO, 300 MHz) δ (ppm): 9.43 (s, 1H), 3.93 (s, 2H), 3.20 (t, 2H), 1.64-1.68 (m, 4H), 1.38 (s, 9H), 1.30-1.37 (m, 4H), 1.14-1.27 (m, 3H), 0.83-0.87 (m, 2H).

d. {2-[3-endo-(3-carbamoylphenyl)-8-azabicyclo[3.2.1]oct-8-yl]-ethyl}-(2-cyclohexylethyl)carbamic acid tert-butyl ester (m/z): [M+H]$^+$ calcd for C$_{29}$H$_{45}$N$_3$O$_3$ 484.35; found, 484.4.
e. 3-endo-{8-[2-(2-cyclohexylethylamino)ethyl]-8-azabicyclo[3.2.1]oct-3-yl}-benzamide (m/z): [M+H]$^+$ calcd for C$_{24}$H$_{37}$N$_3$O 384.29; found, 384.4.

Preparation 20: Synthesis of 3-endo-{8-(2-(3-cyclohexylpropylamino)ethyl)-8-azabicyclo[3.2.1]oct-3-yl]benzamide a. Preparation of 3-cyclohexylpropionaldehyde 3-Cyclohexyl-1-propanol (3.96 g, 27.8 mmol) was dissolved in DCM (90 mL) at 0° C. and treated sequentially with dimethyl sulfoxide (3.25 g, 41.7 mmol), N,N-diisopropylethylamine (8.98 g, 69.6 mmol) and sulfur trioxide pyridine•complex (11 g, 69.6 mmol). After one hour, the reaction mixture was diluted with DCM (100 mL) and washed with 1N aqueous HCl (3×50 mL), saturated sodium bicarbonate (3×50 mL), and brine. The organic layer was dried over MgSO$_4$, filtered, and concentrated to yield the title intermediate as a light yellow oil (3.8 g). $^1$H NMR (d$_6$-DMSO, 300 MHz) δ (ppm): 9.72 (s, 1H), 3.65-3.72 (m, 2H), 2.46 (t, 2H), 1.65-1.73 (m, 3H), 1.51-1.56 (m, 2H), 1.14-1.48 (m, 4H), 0.85-0.96 (m, 2H).

b. Preparation of 2-(3-cyclohexylpropylamino)ethanol

To a solution of ethanolamine (0.44 g, 7.1 mmol) in DCM (15 mL) at 0° C. was added a solution of 3-cyclohexylpropionaldehyde (1.0 g, 7.1 mmol) in DCM (10 mL) followed by sodium triacetoxyborohydride (1.67 g, 7.86 mmol). The resulting mixture was warmed to room temperature. After 2.5 hours the desired product was observed by mass spectrometric analysis. The reaction mixture was stirred overnight, then diluted with DCM (50 mL), washed with saturated sodium bicarbonate (2×50 mL), and brine (50 mL), dried over sodium sulfate, filtered, and concentrated to give a clear oil (1.0 g) which was used in the next step without further purification. ((m/z): [M+H]$^+$ calcd for C$_{11}$H$_{23}$NO, 186.20; found, 186.0).

Following the procedure of Preparation 17 steps b to e, substituting 2-(3-cyclohexylpropylamino)ethanol for 2-phenethylaminoethanol of Preparation 17 step b, the following intermediates were prepared:
c. (3-cyclohexylpropyl)-(2-hydroxyethyl)carbamic acid tert-butyl ester
d. (3-cyclohexylpropyl)-(2-oxo-ethyl)carbamic acid tert-butyl ester $^1$H NMR (d$_6$-DMSO, 300 MHz) δ (ppm): 9.43 (s, 1H), 3.94 (s, 2H), 3.14 (t, 2H), 1.621 (m, 4H), 1.41-1.46 (m, 5H), 1.38 (s, 9H), 1.34-1.36 (m, 4H), 0.86-0.88 (m, 2H).
e. {2-[3-endo-(3-carbamoylphenyl)-8-azabicyclo[3.2.1]oct-8-yl]-ethyl}-(3-cyclohexylpropyl)carbamic acid tert-butyl ester (m/z): [M+H]$^+$ calcd for C$_{30}$H$_{47}$N$_3$O$_3$ 498.36; found, 498.6.
f. 3-endo-{8-[2-(3-cyclohexylpropylamino)ethyl]-8-azabicyclo[3.2.1]oct-3-yl}-benzamide (m/z): [M+H]$^+$ calcd for C$_{25}$H$_{39}$N$_3$O 398.31; found, 398.4.

Preparation 21: Synthesis of 3-endo-(8-{2-[(4,4-difluorocyclohexylmethyl)-amino]ethyl}8-azabicyclo[3.2.1]oct-3-yl)benzamide a. Preparation of (4,4-difluorocyclohexylmethyl)carbamic Acid tert-butyl Ester To a solution of 4-oxocyclohexylmethyl)carbamic acid tert-butyl ester (2.0 g, 8.81 mmol) in dichloromethane (50 mL) at 0° C. under nitrogen was added bis-(2-methoxyethyl) aminosulfur trifluoride (Deoxo-Fluor®) (3.90 g, 17.62 mmol) dropwise. The reaction was allowed to warm to room temperature after addition and stirred at that temperature overnight. The reaction was then slowly quenched with saturated sodium bicarbonate. Additional dichloromethane (300 mL) was added and the resulting mixture was filtered through a pad of Celite. The layers of filtrate were separated and the organic layer was washed with saturated sodium bicarbonate three times followed by brine. The residue was dried over sodium sulfate, filtered and concentrated to give a brownish oil which was further purified by flash chromatography. The compound was eluted with 25% (400 mL) to 30% (200 mL) and 40% (200 mL) ethyl acetate/hexanes. Desired fractions were combined and concentrated to give yellowish oil which solidified upon drying under vacuum. (694 mg).

b. Preparation of (4,4-difluorocyclohexyl)methylamine

The product of the previous step (694 mg) was treated with a 1:1 mixture of dichloromethane and trifluoroacetic acid (6 mL) at room temperature for thirty minutes. The reaction mixture was concentrated and co-evaporated with ethyl acetate three times. The resulting residue was dried under vacuum to give the TFA salt of the title intermediate as a brownish oil.

c. Synthesis of 3-endo-(8-{2-[(4,4-difluorocyclohexylmethyl)-amino]ethyl}8-azabicyclo[3.2.1]oct-3-yl)benzamide To a solution of 3-endo-[8-(2-oxo-ethyl)-8-azabicyclo [3.2.1]oct-3-yl]-benzamide (185 mg, 0.6 mmol) in dichloromethane (3 mL) at room temperature was added sodium triacetoxyborohydride (165 mg, 1.8 mmol) followed by the TFA salt of (4,4-difluorocyclohexyl)methylamine (315 mg, 1.2 mmol) in dichloromethane (2 mL). The reaction mixture was stirred at room temperature for about one and an half hours and then concentrated. The resulting residue was dissolved in 50% acetic acid in water (10 mL), filtered, and purified by reverse phase preparative HPLC to give the bis TFA salt of the title compound (73 mg). (m/z): [M+H]$^+$ calcd for $C_{23}H_{33}F_2N_3O$ 406.27; found, 406.2.

Preparation 22: Synthesis of 3-endo-[8-(2-benzylamino-propyl)-8-aza-bicyclo[3.2.1]oct-3-yl]-phenol a. Preparation of N-{2-[3-endo-(3-hydroxyphenyl)-8-azabicyclo[3.2.1]oct-8-yl]-1-methyl-2-oxo-ethyl}benzamide 2-Benzoylamino-propionic acid (319 mg, 1.65 mmol) and benzotriazol-1-yloxy)tris(dimethylamino)phosphonium hexafluorophosphate (BOP) (731 mg, 1.65 mmol) were added to a stirred solution of the TFA salt of 3-endo-(8-azabicyclo[3.2.1]oct-3-yl)phenol (prepared by the method of Preparation 4) (524 mg, 1.65 mmol) and N,N-diisopropylethylamine (0.86 mL, 4.96 mmol) in THF (14 mL) at room temperature, under an atmosphere of nitrogen. After 90 min, the reaction was quenched by the addition of water (1 mL) and diluted with ethyl acetate (60 mL) and washed with 1M HCl (20 mL), saturated aqueous sodium bicarbonate (20 mL), brine (20 mL), water (20 mL) and brine (20 mL). The organic layer was dried over magnesium sulfate, filtered and concentrated in vacuo. The residue was purified by flash chromatography (EtOAc:hexanes 7:3 to 4:1) to afford the title intermediate (597 mg) as a white solid.

b. Synthesis of 3-endo-[8-(2-benzylamino-propyl)-8-aza-bicyclo[3.2.1]oct-3-yl]-phenol Borane dimethylsulfide complex, 10-10.2M (2.16 mL, 21.6 mmol) was added dropwise to a stirred solution of the product of the previous step (544 mg, 1.44 mmol) in THF (15 mL) at −20° C., under an atmosphere of nitrogen. Upon addition the reaction mixture was warmed to reflux. After 3 hours, the reaction mixture was cooled to −20° C. and methanol (30 mL) was carefully added and stirred overnight. The reaction mixture was concentrated in vacuo and then diluted with 4M HCl in dioxane (10 mL) and stirred for 2 hours. The reaction mixture was again concentrated in vacuo and then diluted with methanol and potassium hydroxide (10 eq) was added. After 2 hours, the reaction mixture was concentrated in vacuo, diluted with water (10 mL) and extracted with a mixture of dichloromethane:THF 3:1 (2×20 mL). The organic layers were combined, dried over magnesium sulfate, filtered and concentrated in vacuo to afford the title compound (509 mg) as a white solid which was used without further purification. (m/z): [M+H]$^+$ calcd for $C_{23}H_{30}N_2O$ 351.25; found, 351.5.

Preparation 23: Synthesis of N-[3-endo-(8-azabicyclo[3.2.1]oct-3-yl)-phenyl]-methanesulfonamide a. Preparation of 3-endo-(3-aminophenyl)-8-azabicyclo[3.2.1]octane-8-carboxylic Acid tert-butyl Ester To a solution of 3-endo-(3-trifluoromethanesulfonyloxyphenyl)-8-aza-bicyclo[3.2.1]octane-8-carboxylic acid tert-butyl ester (400 mg, 0.92 mmol), prepared by the method of Preparation 13, in tetrahydrofuran (9.0 mL) was added benzophenone imine (216.7 mg, 1.2 mmol), potassium tert-butoxide (154.8 mg, 1.38 mmol) and rac-2,2'-bis(diphenylphosphino)-1,1'-binapthyl (BINAP) (51.5 mg, 0.08 mmol). The resulting mixture was degassed and flushed with nitrogen before palladium (II) acetate (19.3 mg, 0.08 mmol) was added. The mixture was then heated to 78° C. for two hours. After being cooled to room temperature, the reaction mixture was treated with 2 N HCl (5.0 mL) for three hours and then basified to pH 8 with 5% aqueous sodium hydroxide. The aqueous layer was extracted with ethyl acetate. The resulting organic layer was washed with saturated sodium bicarbonate and brine, dried over sodium sulfate, filtered, concentrated, and further purified by reverse phase preparative HPLC to provide the TFA salt of the title intermediate. (m/z): [M+H]$^+$ calcd for $C_{18}H_{26}N_2O_2$: 303.41; found: 303.2.

b. Preparation of 3-endo-(3-methanesulfonylaminophenyl)-8-aza-bicyclo[3.2.1]octane-8-carboxylic Acid tert-butyl Ester To a stirred mixture of the TFA salt of 3-endo-(3-aminophenyl)-8-azabicyclo[3.2.1]octane-8-carboxylic acid tert-butyl ester (114 mg, 0.37 mmol), N,N-diisopropylethylamine (146 mg, 1.13 mmol) and 4-dimethylaminopyridine (DMAP) (9 mg, 0.075 mmol) in DCM (2.0 mL) at 0° C. was added a solution of methanesulfonylchloride (45 mg, 0.39 mmol) in DCM (0.2 mL). Thirty minutes later, analytical HPLC indicated the reaction was not complete. Additional methanesulfonyl chloride (17 mg, 0.15 mmol) was added and the mixture was stirred at 0° C. for another thirty minutes before it was quenched with saturated sodium bicarbonate. The aqueous layer was extracted with DCM. The organic layer was washed with brine, dried over sodium sulfate, filtered and concentrated to give the title intermediate as a yellowish oil (140 mg).

c. Synthesis of N-[3-endo-(8-azabicyclo[3.2.1]oct-3-yl)-phenyl]-methanesulfonamide The oily product of the previous step was treated with DCM (2 mL) and TFA (20 mL) at room temperature for thirty minutes at which time analytical HPLC showed the reaction was complete. The reaction mixture was concentrated and the resulting residue was coevaporated with ethyl acetate three times and further dried under vacuum to give the TFA salt of the title intermediate as a yellowish oil, which was used without further purification.

Preparation 24: Synthesis of N-cyclohexylmethyl-(2-oxoethyl)-carbamic Acid Benzyl Ester Bisulfite Adduct a. Preparation of N-cyclohexylmethyl-(2,2-diethoxyethyl)amine

To a mixture of 2,2-diethoxyethylamine (209 mL, 1.43 mol) and MeTHF (1050 L) was added cyclohexanecarbaldehyde (107 mL, 0.89 mol). The reaction mixture was stirred for 30 min at room temperature and cooled to 0° C. Sodium triacetoxyborohydride (378 g, 1.79 mol) was added over 40 min and the reaction mixture was stirred for 2 h and cooled to 0° C. 1 M NaOH (1 L) was added. The organic layer was washed with brine in water (1:1, 2×1 L) and the volume was reduced to ~20%. MeTHF (1 L) was added and the volume reduced to ~20%. The solution of the crude title intermediate was used directly in the next step.

b. Preparation of N-cyclohexylmethyl-(2,2-diethoxyethyl)carbamic Acid Benzyl Ester To the product of the previous step (~213 g, ~0.9 mol) was added MeTHF (2 L) and DIPEA (233 mL, 1.34 mol). The reaction mixture was cooled to 0° C. and benzylchloroformate (140 mL, 0.98 mol) was added dropwise. The reaction mixture was stirred for 30 min at 0° C., for 2 h at 0° C. to room temperature, and then for 1 h at room temperature. Water (1.6 L) was added and the reaction mixture was stirred for 10 min. The phases were separated and the organic layer was washed with sodium bicarbonate (1.6 L) and water (1.6 L). The layers were separated and the organic layer was reduced to about 20%. MeTHF (1 L) was added and the volume reduced to ~20%. The solution of the crude title intermediate was used directly in the next step.

c. Synthesis of N-cyclohexylmethyl-(2-oxoethyl)-carbamic Acid Benzyl Ester Bisulfite Adduct To the product of the previous step (~302 g, ~0.62 mol) and acetonitrile (2 L) was added 1 M HCl (2 L) and the reaction mixture was stirred at 30° C. for 7 h. Ethyl acetate (2 L) was added and the reaction mixture was stirred for 10 min. The phases were separated, the organic layer was washed with 1 M HCl (1.5 L), the phases were again separated and the organic layer was washed with 0.5 M HCl (1 L). Sodium bisulfite (71.4 g, 0.69 mol) was added and the reaction mixture was stirred overnight, and then filtered. The reactor and filter cake were washed with ethyl acetate (1 L). The resulting solution was dried in air for 2 h and under vacuum overnight to provide the title compound as white solid (199 g, >99% area purity by HPLC). The filtrate was treated by the same procedure to provide a second lot of the title compound (30 g).

Preparation 25: Synthesis of 3-endo-(8-azabicyclo [3.2.1]oct-3-yl)-benzamide a. Preparation of 8-benzyl-3-(3-methoxyphenyl)-8-azabicyclo[3.2.1]oct-2-ene To a 3 L flask was added 8-benzyl-3-exo-(3-methoxyphenyl)-8-azabicyclo[3.2.1]octan-3-ol hydrochloride (383.9 g, 1.06 mol), 6 M HCl (800 mL), and MeTHF (200 mL). The resulting slurry was heated at 70° C. for 2.5 h under nitrogen. The reaction mixture was transferred to a 12 L reactor and cooled to 10° C. The reaction flask was washed with MeTHF (1 L) that was added to the 12 L reactor. NaOH (50 wt % in water, 200 mL) was added and additional NaOH (50 wt %, 150 mL) was added in portions until pH ~13 was reached. The phases were separated, the water layer was extracted with MeTHF (1 L), and combined MeTHF layers were washed with brine (1 L). Solvent was reduced by rotary evaporation at 30 to 40° C. yielding the title intermediate (360 g) as a thick oil. EtOH (1.5 L) was added and the volume was reduced to ~500 mL and then adjusted to 1.8 L.

b. Preparation of 3-endo-(3-methoxyphenyl)-8-azabicyclo[3.2.1]octane

To 8-benzyl-3-(3-methoxyphenyl)-8-azabicyclo[3.2.1] oct-2-ene (in EtOH 95%, 400 mL, 0.20 mol), prepared in the previous step, was added 6 M HCl (45 mL) and then MeTHF (50 mL). The reaction mixture was purged with nitrogen, heated to 40° C. and palladium on carbon (10 weight %, 8 g) was added. The reactor was pressurized with hydrogen (3×20 psi) and then hydrogenated at 20 psi at 40° C. for 18 h. The reaction mixture was filtered through Celite, concentrated, washed with MeTHF (2×100 mL), filtered through a coarse glass filter, washed with MeTHF (10 mL) and dried on the filter to provide the HCl salt of the title intermediate as white solid (31 g, single isomer, (exo isomer undetectable by HPLC)). An additional 5.2 g of product was recovered from the mother liquor.

c. Preparation of 3-endo-(8-azabicyclo[3.2.1]oct-3-yl)-phenol

To a 500 mL flask was added 3-endo-(3-methoxyphenyl)-8-azabicyclo[3.2.1]octane hydrochloride (115 g, 0.45 mol) and hydrobromic acid (48 weight % in water, 100 mL, 0.88 mol). The mixture was heated to 120° C. and held at that temperature for 24 h with stirring. Additional hydrobromic acid solution (25 mL) was added and the reaction mixture was heated with stirring for 6 h and then cooled to 70° C. Acetonitrile (200 mL) was added and the resulting slurry was cooled to 10° C. and then filtered, and the filter cake was washed with acetonitrile (50 mL) to yield the HBr salt of the title intermediate (99 g, >99% pure) as a white granular solid.

d. Preparation of 2,2,2-trifluoro-1-[3-endo-(3-hydroxyphenyl)-8-azabicyclo[3.2.1]oct-8-yl]ethanone To a solution of 3-endo-(8-azabicyclo[3.2.1]oct-3-yl)-phenol hydrobromide (54.4 g, 0.19 mol), toluene (210 mL), and triethylamine (40 mL, 0.29 mol), was added trifluoroacetic anhydride (54 mL, 0.38 mol) over 20 min. The reaction mixture was stirred at 40° C. for 2 h. Ethyl acetate (370 mL) and brine in water (1:1, 265 mL) were added. The reaction mixture was stirred for 15 min, the phases were separated. To the organic layer was added saturated sodium bicarbonate (300 mL) and the mixture was stirred vigorously overnight. The phases were separated and the organic layer was washed with brine in water (1:1, 265 mL) dried over sodium sulfate and most of the solvent was removed by rotary evaporation. Toluene (100 mL) was added and the solvent removed by rotary evaporation to provide the crude title intermediate.

e. Preparation of Trifluoromethanesulfonic Acid 3-endo-[8-(2,2,2-trifluoro-acetyl)-8-azabicyclo[3.2.1]oct-3-yl]phenyl Ester To a 500 mL flask was added the ethyl acetate solution (220 mL) of the intermediate of the previous step (32.8 g, 0.11 mol) and triethylamine (23 mL. 0.17 mol). The solution was cooled to 5° C. and trifluoromethane sulfonyl chloride (14 mL, 0.13 mol) was added dropwise. The mixture was allowed to warm to 25° C. and stirred at that temperature for 1 h. Saturated sodium bicarbonate (200 mL) was added, the layers were separated, brine (150 mL) was added to the organic layer, the layers were again separated, and solvent was removed from the organic layer to provide the crude title intermediate.

f. Preparation of 3-endo-[8-(2,2,2-trifluoroacetyl)-8-azabicyclo[3.2.1]oct-3-yl]-benzonitrile To a 100 mL flask was added trifluoromethanesulfonic acid 3-endo-[8-(2,2,2-trifluoro-acetyl)-8-azabicyclo[3.2.1]oct-3-yl]phenyl ester (25.3 g, 58.7 mmol), tris(dibenzylideneacetone) dipalladium (0) (0.81 g, 0.9 mmol), 1,1'-bis(diphenylphosphino) ferrocene (1.01 g, 1.8 mmol), and zinc cyanide (4.2 g, 35.8 mmol). Three times, the flask was purged with nitrogen for 5 min and then placed under house vacuum for 5 min. To the flask was added DMF (150 mL) and distilled water (2.5 mL). The solution was purged with nitrogen with stirring for 10 min, heated to 120° C. and stirred at 120° C. under nitrogen for 4 h. When the reaction was completed 20 g of product from a previous lot, prepared by the same procedure, was added and stirred for 20 min.

Most of the solvent was removed by distillation and the solution was cooled to 22° C. To the solution was added ethyl acetate (445 mL) and the resulting solution was filtered through Celite. Sodium bicarbonate (450 mL) was added and the solution was stirred for 15 min. The layers were separated and the organic layer was washed with diluted brine (2×95 mL), and filtered through sodium sulfate. The volume was reduced to about 50 mL by removal of ethyl acetate. Isopropyl alcohol (150 mL) was added and the solution was agitated at 22° C. for 1 h. Solids were isolated by filtration and washed with isopropyl alcohol (2×25 mL) to provide the title intermediate (33.5 g, 100% pure by HPLC) as an off-white/light brown solid. A second crop of product (6.3 g, >98% pure by HPLC) was isolated from the filtrate.

g. Synthesis of 3-endo-(8-azabicyclo[3.2.1]oct-3-yl)-benzamide

A solution of 3-endo-[8-(2,2,2-trifluoroacetyl)-8-azabicyclo[3.2.1]oct-3-yl]-benzonitrile (10 g, 32 mmol) in sulfuric acid (96%, 12 mL) was heated to 50° C. with stirring and held at that temperature with stirring for 2 h. The reaction mixture was cooled to 22° C. and added slowly to a 500 mL flask containing 5 N NaOH (90 mL) and methanol (100 mL) which was cooled to 10° C. Salt precipitates were filtered and the filtrate was stirred at 22° C. for 1 h. The reaction mixture was concentrated under reduced pressure. To the residue was added MeTHF (150 mL) and the reaction mixture was stirred at 22° C. for 5 min. The layers were separated and MeTHF (100 mL) was added to the aqueous layer. The layers were separated and brine (150 mL) was added to the combined organic layers. The layers were separated and the organic layer was dried over potassium carbonate and filtered, and the solvent was removed. A mixture of EtOH (25 mL) and concentrated HCl (2.6 mL) was added to the residue with stirring and then MTBE (25 mL) was added and the solution was stirred at 22° C. Precipitated solids were filtered and air dried to provide the HCl salt of the title compound (8 g, 97% purity by HPLC) as a white solid.

Example 1: Synthesis of N-benzyl-2-hydroxy-N-{2-[3-endo-(3-hydroxyphenyl)-8-azabicyclo[3.2.1]oct-8-yl]ethyl}acetamide 3-endo-[8-(2-Benzylaminoethyl)-8-azabicyclo[3.2.1]oct-3-yl]phenol, prepared by the methods of Preparations 1 and 2 (246 mg, 0.73 mmol) was dissolved in dichloromethane (3.6 mL) and N,N-diisopropylethylamine (123 mg, 0.95 mmol) at room temperature. The resulting mixture was cooled to 0° C. Acetoxyacetyl chloride (119 mg, 0.87 mmol) was added and the mixture was stirred at 0° C. for about 30 minutes. The reaction was quenched with saturated sodium bicarbonate and extracted with dichloromethane. The organic layer was washed with brine, dried over sodium sulfate, filtered and concentrated to give a yellowish oil. The oily mixture was then dissolved in 50% acetic acid/water (10 mL), filtered and purified by preparative HPLC to give TFA salts of a mono-acylated product (62 mg) and a bisacylated byproduct (160.9 mg). The bis acylated byproduct TFA salt (160.9 mg) was dissolved in ethanol (2 mL) at room temperature and treated with 1N aqueous sodium hydroxide (1.0 mL) for about 30 minutes. After concentration, the residue was dissolved in 50% acetic acid in water (10 mL), filtered and purified by reverse phase preparative HPLC to give the TFA salt of the title compound as a white solid (46.5 mg). (m/z): [M+H]$^+$ calcd for $C_{24}H_{30}N_2O_3$ 395.24; found, 395.3.

Example 2: Synthesis of N-benzyl-N-{2-[3-endo-(3-hydroxyphenyl)-8-aza-bicyclo[3.2.1]oct-8-yl]ethyl}acetamide To a solution of the TFA salt of 3-endo-[8-(2-benzylaminoethyl)-8-aza-bicyclo[3.2.1]oct-3-yl]phenol, prepared by the methods of Preparations 1 and 2 (25 mg, 0.044 mmol) in dichloromethane (0.2 mL) at room temperature was added N,N-diisopropylethylamine (23 mg, 0.177 mmol), followed by acetylchloride (0.044 mmol). After about 10 minutes, the reaction mixture was concentrated. The residue was redissolved in 50% acetic acid/water (1.5 mL), filtered, purified by reverse phase preparative HPLC to provide the TFA salt of the title compound (10 mg). (m/z): [M+H]$^+$ calcd for $C_{24}H_{30}N_2O_2$ 379.23; found, 379.2.

Examples 3-5

Using processes similar to that of Example 2, except replacing the acetylchloride with 0.044 mmol of the appropriate acyl chloride, the TFA salts of the compounds of Examples 3-5 were prepared.

Example 3 cyclopentanecarboxylic acid benzyl-{2-[3-endo-(3-hydroxyphenyl)-8-aza-bicyclo[3.2.1]oct-8-yl]-ethyl}-amide (18.3 mg) (m/z): [M+H]$^+$ calcd for $C_{28}H_{36}N_2O_2$, 433.29; found 433.2.

Example 4

N-benzyl-2-ethyl-N-{2-[3-endo-(3-hydroxyphenyl)-8-azabicyclo[3.2.1]oct-8-yl]ethyl}butyramide (15.1 mg) (m/z): [M+H]$^+$ calcd for $C_{28}H_{38}N_2O_2$, 435.30; found 435.2.

Example 5

N-benzyl-N-{2-[3-endo-(3-hydroxyphenyl)-8-azabicyclo[3.2.1]oct-8-yl]-ethyl}succinamic acid methyl ester (19.6 mg) (m/z): [M+H]$^+$ calcd for $C_{27}H_{34}N_2O_2$, 451.26; found 451.2.

Example 6: Synthesis of N-benzyl-N-{2-[3-endo-(3-hydroxyphenyl)-8-aza-bicyclo[3.2.1]oct-8-yl]-ethyl}succinamic Acid To a solution of the TFA salt of 3-endo-[8-(2-benzylaminoethyl)-8-aza-bicyclo[3.2.1]oct-3-yl]phenol, prepared by the methods of Preparations 1 and 2 (110 mg, 0.195 mmol) in dichloromethane (1.0 mL) at room temperature was added N,N-diisopropylethylamine (101 mg, 0.78 mmol) followed by 3-carbomethoxypropionyl chloride (44 mg, 0.29 mmol). After about thirty minutes, the reaction mixture was concentrated. The residue was redissolved in ethanol (2 mL), treated with lithium hydroxide monohydrate (33 mg, 0.78 mmol) in water (1 mL) for about thirty minutes, and then concentrated. The residue was redissolved in 50% acetic acid in water (10 mL), filtered and purified by reverse phase preparative HPLC to give the TFA salt of the title compound (46.5 mg). (m/z): [M+H]$^+$ calcd for $C_{26}H_{32}N_2O_2$, 437.25; found 437.12.

Example 7: Synthesis of N-cyclohexylmethyl-N-{2-[3-endo-(3-hydroxyphenyl)-8-azabicyclo[3.2.1]oct-8-yl]ethyl}acetamide To a solution of the TFA salt of 3-endo-{8-[2-(cyclohexylmethylamino)ethyl]-8-azabicyclo[3.2.1]oct-3-yl-phenol prepared by the method of Preparations 1 and 3 (25 mg, 0.044 mmol) in dichloromethane (0.2 mL) at room temperature was added N,N-diisopropylethylamine (34 mg, 0.26 mmol) followed by acetylchloride (0.044 mmol). The reaction mixture was concentrated by rotary evaporation. The residue was dissolved in ethanol (0.2 mL) and hydrolyzed with 1N aqueous NaOH (0.1 mL) at room temperature for 30 minutes. Solvents were removed by rotary evaporation and the resulting residue was dissolved in 50% acetic acid in water (1.5 mL), filtered and purified by preparative HPLC to give the TFA salt of the title compound (12 mg). (m/z): [M+H]$^+$ calcd for $C_{24}H_{36}N_2O_2$, 385.29; found 385.2.

Examples 8-14

Using processes similar to that of Example 7, except replacing the acetylchloride with 0.044 mmol of the appropriate acyl chloride, the TFA salts of the compounds of Examples 3-5 were prepared.

Example 8

N-cyclohexylmethyl-N-{2-[3-endo-(3-hydroxyphenyl)-8-azabicyclo[3.2.1]oct-8-yl]ethyl}propionamide (7.1 mg) (m/z): [M+H]$^+$ calcd for $C_{25}H_{38}N_2O_2$, 399.30; found 399.2.

Example 9 cyclopentanecarboxylic acid cyclohexylmethyl-{2-[3-endo-(3-hydroxy-phenyl)-8-azabicyclo[3.2.1]oct-8-yl]ethyl}amide (16.4 mg) (m/z): [M+H]$^+$ calcd for $C_{28}H_{42}N_2O_2$, 439.34; found 439.2.

Example 10 cyclohexanecarboxylic acid cyclohexylmethyl-{2-[3-endo-(3-hydroxy-phenyl)-8-azabicyclo[3.2.1]oct-8-yl]ethyl}amide (14 mg) (m/z): [M+H]$^+$ calcd for $C_{29}H_{44}N_2O_2$, 453.35; found 453.4.

Example 11

N-cyclohexylmethyl-3-cyclopentyl-N-{2-[3-endo-(3-hydroxyphenyl)-8-aza-bicyclo[3.2.1]oct-8-yl] ethyl}propionamide (11.4 mg) (m/z): [M+H]$^+$ calcd for $C_{30}H_{46}N_2O_2$, 467.37; found 467.4.

Example 12

N-cyclohexylmethyl-N-{2-[3-endo-(3-hydroxyphenyl)-8-aza-bicyclo[3.2.1]oct-8-yl]ethyl}-3-methylbutyramide (14.1 mg) (m/z): [M+H]$^+$ calcd for $C_{27}H_{42}N_2O_2$, 427.33; found 427.4.

Example 13

N-cyclohexylmethyl-2-hydroxy-N-{2-[3-endo-(3-hydroxyphenyl)-8-aza-bicyclo[3.2.1]oct-8-yl]ethyl}acetamide (10.8 mg) (m/z): [M+H]$^+$ calcd for $C_{24}H_{36}N_2O_3$, 401.28; found 401.2.

Example 14

N-cyclohexylmethyl-N-{2-[3-endo-(3-hydroxyphenyl)-8-aza-bicyclo[3.2.1]oct-8-yl]ethyl}-2-phenylacetamide (16.8 mg) (m/z): [M+H]$^+$ calcd for $C_{30}H_{40}N_2O_2$, 461.32; found 461.2.

Example 15: Synthesis of 1-[(cyclohexylmethyl-{2-[3-endo-(3-hydroxyphenyl)-8-azabicyclo[3.2.1]oct-8-yl]ethyl}carbamoyl)methyl]cyclohexyl}-acetic Acid To a solution of the TFA salt of 3-endo-{8-[2-(cyclohexylmethylamino)-ethyl]-8-azabicyclo[3.2.1]oct-3-yl-phenol prepared by the method of Preparations 1 and 3 (24 mg, 0.042 mmol) in dichloromethane (0.4 mL) at room temperature was added N,N-diisopropylethylamine (22 mg, 0.17 mmol) followed by 1,1-cyclohexanediacetic anhydride (0.042 mmol). After 20 minutes the reaction went to completion and the reaction mixture was concentrated. The residue was dissolved in methanol and hydrolyzed with 1N aqueous NaOH (0.1 mL) at room temperature for 30 minutes. Solvents were removed and the resulting residue was dissolved in 50% acetic acid in water (1.5 mL), filtered and purified by preparative HPLC to give the TFA salt of the title compound. (m/z): [M+H]$^+$ calcd for $C_{32}H_{48}N_2O_4$, 525.37; found 525.2.

Examples 16-17

Using processes similar to that of Example 15, except replacing the 1,1-cyclohexanediacetic anhydride with 0.042 mmol of the listed anhydride, the TFA salts of the compounds of Examples 16 and 17 were prepared.

Example 16

{1-[(cyclohexylmethyl-{2-[3-endo-(3-hydroxyphenyl)-8-azabicyclo[3.2.1]oct-8-yl]-ethyl}carbamoyl)methyl] cyclopentyl}acetic acid reagent: 3,3-tetramethyleneglutaric anhydride (m/z): [M+H]$^+$ calcd for $C_{31}H_{46}N_2O_4$, 511.36; found 511.2.

Example 17

2-(cyclohexylmethyl-{2-[3-endo-(3-hydroxyphenyl)-8-azabicyclo[3.2.1]oct-8-yl]-ethyl}carbamoyl)cyclohexanecarboxylic acid reagent: 1,2-cyclohexanedicarboxylic anhydride (m/z): [M+H]$^+$ calcd for $C_{30}H_{44}N_2O_4$, 497.34; found 497.2.

Example 18A: N-cyclohexylmethyl-N-{2-[3-endo-(3-hydroxyphenyl)-8-aza-bicyclo[3.2.1]oct-8-yl]ethyl}succinamic Acid To a solution of 3-endo-{8-[2-(cyclohexylmethylamino)-ethyl]-8-azabicyclo[3.2.1]oct-3-yl-phenol prepared by the method of Preparations 1 and 3 and converted to free base form (83 mg, 0.24 mmol) in dichloromethane (2.5 mL) at room temperature was added N,N-diisopropylethylamine (124 mg, 0.96 mmol) followed by 3-carbomethoxypropionyl chloride (72 mg, 0.48 mmol). The resulting mixture was stirred at room temperature for about 10 minutes and then concentrated, dissolved in ethanol (2 mL) and hydrolyzed with lithium hydroxide monohydrate (61 mg) in water (2 mL) for about 30 minutes. The reaction mixture was then concentrated, dissolved in 50% acetic acid in water (10 mL), filtered, and purified by reversed phase preparative HPLC to give the TFA salt of the title compound. (m/z): [M+H]$^+$ calcd for $C_{26}H_{38}N_2O_4$, 443.29; found 443.2.

Example 18B: N-cyclohexylmethyl-N-{2-[3-endo-(3-hydroxyphenyl)-8-aza-bicyclo[3.2.1]oct-8-yl]ethyl}succinamic Acid To a solution of the bis TFA salt of 3-endo-{8-[2-(cyclohexylmethylamino)ethyl]-8-azabicyclo[3.2.1]oct-3-yl}phenol, prepared by the method of Preparation 4 and analogously to that of Preparation 11 (70 mg, 0.12 mmol) in dichloromethane (0.4 mL) at room temperature was added N,N-diisopropylethyl amine (62 mg, 0.48 mmol) followed by succinic anhydride (0.16 mmol). The resulting mixture was stirred at room temperature for about 10 minutes before it was concentrated. The residue was then redissolved in 50% acetic acid in water (10 mL), filtered, and purified by reverse phase preparative HPLC. The residue was freeze dried, and then the solid was dissolved in a mixture of MeOH (1.0 mL) and water (2.0 mL) and treated with lithium hydroxide monohydrate (30 mg) at ambient temperature for thirty minutes. The product was concentrated, dissolved in 50% acetic acid in water (10 mL), filtered, and purified by reverse phase preparative HPLC to give the TFA salt of the title compound (28.9 mg). (m/z): [M+H]$^+$ calcd for $C_{26}H_{38}N_2O_4$, 443.29; found 443.5. $^1$H NMR (CD$_3$OD, 300 MHz) δ (ppm): 7.10-7.155 (m, 1H), 6.91 (d, J=8.4 Hz, 1H), 6.85 (s, 1H), 6.63 (d, J=8.1 Hz, 1H), 4.01 (brs, 2H), 3.71-3.79 (m, 2H), 3.26-3.28 (m, obscure 2H), 3.10-3.12 (m, 3H), 2.67 (s, 4H), 2.48-2.52 (m, 4H), 2.04-2.08 (m, 2H), 1.706-1.875 (m, 8H), 1.238-1.30 (m, 3H), 0.98-1.03 (m, 2H).

Example 19: Synthesis of 4-(cyclohexylmethyl-{2-[3-endo-(3-hydroxyphenyl)-8-azabicyclo[3.2.1]oct-8-yl]ethyl}carbamoyl)-3,3-dimethylbutyric Acid To a solution of the TFA salt of 3-endo-{8-[2-(cyclohexylmethylamino)-ethyl]-8-azabicyclo[3.2.1]oct-3-yl-phenol prepared by the method of Preparations 1 and 3 (25 mg, 0.044 mmol) in dichloromethane (0.4 mL) at room temperature was added N,N-diisopropylethylamine (23 mg, 0.18 mmol) followed by 3,3-dimethyl glutaric anhydride (9 mg, 0.07 mmol). The reaction was stirred at room temperature overnight. The reaction mixture was concentrated by rotary evaporation, dissolved in 50% acetic acid in water (1.5 mL), filtered, and purified by preparative HPLC to give the TFA salt of the title compound (13.3 mg). (m/z): [M+H]$^+$ calcd for $C_{29}H_{44}N_2O_4$, 485.34; found 485.4.

Example 20: Synthesis of [(cyclohexylmethyl-{2-[3-endo-(3-hydroxyphenyl)-8-aza-bicyclo[3.2.1]oct-8-yl]ethyl}carbamoyl)methanesulfonyl] acetic Acid To a solution of methoxycarbonylmethanesulfonyl acetic acid (10 mg, 0.525 mmol) in dimethylacetamide (1 mL) at room temperature was added 1,1'-carbonyldiimidazole (114 mg, 0.7 mmol). Two hours later, to this stirred mixture was added a solution of the TFA salt of 3-endo-{8-[2-(cyclohexylmethylamino)-ethyl]-8-azabicyclo[3.2.1]oct-3-yl-phenol prepared by the method of Preparations 1 and 3 (100 mg, 0.175 mmol) and N,N-diisopropylethylamine (91 mg, 0.7 mmol) in dimethylacetamide (1 mL). The reaction mixture was heated to 65° C. for 3 hours and then stirred at room temperature overnight. The reaction mixture was diluted with ethanol (2.0 mL) and treated with a solution of lithium hydroxide monohydrate (150 mg) in water (1.5 mL) for about 30 minutes. The solvents were removed and the residue was dissolved in 50% acetic acid in water (10 mL), filtered and purified by reversed phase preparative HPLC to give the TFA salt of the title compound as a white solid (28.3 mg). (m/z): [M+H]$^+$ calcd for $C_{26}H_{38}N_2O_6S$, 507.26; found 507.2. $^1$H NMR (CD$_3$OD, 300 MHz) δ (ppm): 7.1-7.17 (m, 1H), 6.87-6.94 (m, 2H), 6.63-6.72 (m, 1H), 4.63 (s, 2H), 4.44 (s, 2H), 4.07 (brs, 2H), 3.80 (t, J=5.7 Hz, 2H), 3.34 (d, J=7.2 Hz, obscure 2H), 3.13-3.2 (m, 3H), 2.51-2.53 (m, 4H), 1.69-1.88 (m, 8H), 1.19-1.33 (m, 3H), 0.92-1.06 (m, 2H).

Example 21: Synthesis of N-cyclohexylmethyl-N-{2-[3-endo-(3-hydroxy-phenyl)-8-azabicyclo[3.2.1]oct-8-yl]ethyl}malonamic Acid To a solution of malonic acid mono-tert-butyl ester (84 mg, 0.53 mmol) in dimethylacetamide (1.0 mL) at room temperature was added 1,1'-carbonyldiimidazole (114 mg, 0.7 mmol). Two hours later, to this stirred mixture was added a solution of the TFA salt of 3-endo-{8-[2-(cyclohexylmethylamino)-ethyl]-8-azabicyclo[3.2.1]oct-3-yl-phenol prepared by the method of Preparations 1 and 3 (100 mg, 0.175 mmol) and N,N diisopropylethylamine (91 mg, 0.7 mmol) in dimethylacetamide (1 mL). The resulting reaction mixture was heated to 65° C. for 3 hours and stirred at room temperature overnight. The reaction mixture was diluted with ethyl acetate, and washed successively with water and brine. The reaction mixture was dried over sodium sulfate, filtered, and concentrated to give a yellowish oil and further dried under vacuum for 30 min. The residue was treated with trifluoroacetic acid (5 mL) at room temperature for 10 minutes. The reaction mixture was diluted with water (5 mL), filtered, and purified by reversed phase preparative HPLC to give the TFA salt of the title compound as a white solid (51.5 mg). (m/z): [M+H]$^+$ calcd for $C_{25}H_{36}N_2O_4$, 429.28; found 429.2. $^1$H NMR (CD$_3$OD, 300 MHz) δ (ppm): 7.11-7.17 (m, 1H), 6.87-6.94 (m, 2H), 6.63-6.66 (m, 1H), 4.08 (brs, 2H), 3.77-3.81 (m, 2H), 3.58 (deformed s, 1H), 3.24 (d, J=6.9 Hz, obscure 2H), 3.14-3.18 (m, 3H), 2.51-2.54 (m, 4H), 2.05-2.09 (m, 2H), 1.69-1.89 (m, 8H), 1.24-1.31 (m, 3H), 0.98-1.03 (m, 2H).

Example 22: Synthesis of 3-sec-butyl-1-cyclohexylmethyl-1-{2-[3-endo-(3-hydroxyphenyl)-8-azabicyclo[3.2.1]oct-8-yl]ethyl}-urea To a solution of the TFA salt of 3-endo-{8-[2-(cyclohexylmethylamino)-ethyl]-8-azabicyclo[3.2.1]oct-3-yl-phenol prepared by the method of Preparations 1 and 3 (30 mg, 0.053 mmol) in dimethylformamide (0.2 mL) at room temperature was added N,N-diisopropylethylamine (27 mg, 0.21 mmol) followed by sec-butyl isocyanate (0.079 mmol). The resulting mixture was shaken at room temperature overnight, concentrated, dissolved in 50% acetic acid in water (1.5 mL), filtered, and purified by preparative HPLC to give the TFA salt of the title compound (17.8 mg). (m/z): [M+H]$^+$ calcd for $C_{27}H_{43}N_3O_2$, 442.35; found 442.4.

Examples 23-28

Using processes similar to that of Example 22, except replacing the sec-butyl isocyanate with 0.079 mmol of the listed isocyanate, the TFA salts of the compounds of Examples 23 to 28 were prepared.

Example 23

3-benzyl-1-cyclohexylmethyl-1-{2-[3-endo-(3-hydroxyphenyl)-8-aza-bicyclo[3.2.1]oct-8-yl]ethyl}urea (13.2 mg); reagent: benzylisocyanate (m/z): [M+H]$^+$ calcd for $C_{30}H_{41}N_3O_2$, 476.33; found 476.2.

Example 24

3-benzo[1,3]dioxol-5-yl-1-cyclohexylmethyl-1-{2-[3-endo-(3-hydroxy-phenyl)-8-azabicyclo[3.2.1]oct-8-yl]ethyl}urea (12.0 mg); reagent: 3,4-methylenedioxyphenyl isocyanate (m/z): [M+H]$^+$ calcd for $C_{30}H_{39}N_3O_4$, 506.30; found 506.2.

Example 25

1-cyclohexylmethyl-3-(3-fluorophenyl)-1-{2-[3-endo-(3-hydroxyphenyl)-8-azabicyclo[3.2.1]oct-8-yl]-ethyl}urea (14.3 mg); reagent: 3-fluorophenyl isocyanate (m/z): [M+H]$^+$ calcd for $C_{29}H_{38}FN_3O_2$, 480.30; found 480.2.

Example 26

1-cyclohexylmethyl-1-{2-[3-endo-(3-hydroxyphenyl)-8-aza-bicyclo[3.2.1]oct-8-yl]ethyl}-3-pentylurea (14.6 mg); reagent: pentylisocyanate (m/z): [M+H]$^+$ calcd for $C_{28}H_{45}N_3O_2$, 456.36; found 456.4.

Example 27

1-cyclohexylmethyl-3-(4-fluorobenzyl)-1-{2-[3-endo-(3-hydroxyphenyl)-8-azabicyclo[3.2.1]oct-8-yl]ethyl}urea (13.6 mg); reagent: 4-fluorobenzyl isocyanate (m/z): [M+H]$^+$ calcd for $C_{30}H_{40}FN_3O_2$, 494.34; found 494.2.

Example 28

1-cyclohexylmethyl-3-(4-difluoromethoxyphenyl)-1-{2-[3-endo-(3-hydroxy-phenyl)-8-azabicyclo[3.2.1]oct-8-yl]ethyl}urea (21.8 mg); reagent: 4-difluoromethoxyphenyl isocyanate (m/z): [M+H]$^+$ calcd for $C_{30}H_{39}F_2N_3O_3$, 528.31; found 528.2.

Example 29A: Synthesis of N-cyclohexylmethyl-N-{2-[3-endo-(3-hydroxyphenyl)-8-aza-bicyclo[3.2.1]oct-8-yl]ethyl}succinamic Acid Methyl Ester To a solution of 3-endo-{8-[2-(cyclohexylmethylamino)-ethyl]-8-azabicyclo[3.2.1]oct-3-yl-phenol prepared by the method of Preparations 1 and 3 (114 mg, 0.20 mmol) in dichloromethane (1 mL) at room temperature was added N,N-diisopropylethylamine (103 mg, 0.80 mmol) followed by a solution of 3-carbomethoxypropionyl chloride (0.20 mmol) in dichloromethane (0.3 mL). The resulting mixture was stirred at room temperature for about 10 minutes, concentrated, redissolved in 50% acetic acid in water (5 mL), filtered, and purified by reversed phase preparative HPLC to give the TFA salt of the title compound as a white salt (46.4 mg). (m/z): [M+H]$^+$ calcd for $C_{27}H_{40}N_2O_4$, 457.31; found 457.3.

Example 29B: Synthesis of N-cyclohexylmethyl-N-{2-[3-endo-(3-hydroxyphenyl)-8-azabicyclo[3.2.1]oct-8-yl]ethyl}succinamic Acid Methyl Ester To a solution of the bis TFA salt of 3-endo-{8-[2-(cyclohexylmethylamino)ethyl]-8-azabicyclo[3.2.1]oct-3-yl}phenol, prepared by the method of Preparation 4 and analogously to that of Preparation 11 (88 mg, 0.15 mmol) in dichloromethane (0.4 mL) at room temperature was added N,N-diisopropylethyl amine (80 mg, 0.62 mmol) followed by a DCM solution (0.15 mL) of 3-carbomethoxypropionyl chloride (0.18 mmol). The resulting mixture was stirred at room temperature for about 10 minutes. Mass spectrometry (electron spray) showed starting material was still present. Additional 3-carbomethoxypropionyl chloride (0.05 mmol) was added. When the reaction was judged complete by analytical HPLC, the reaction mixture was concentrated, dissolved in 50% acetic acid in water (10 mL), filtered, and purified by reversed phase preparative HPLC to give the TFA salt of the title compound as a white solid (44.7 mg). (m/z): [M+H]$^+$ calcd for $C_{27}H_{40}N_2O_4$, 457.31; found 457.5.

¹H NMR (CD₃OD, 300 MHz) δ (ppm): 7.10-7.15 (m, 1H), 6.90 (d, J=7.8 Hz, 1H), 6.85 (s, 1H), 6.63 (d, J=7.8 Hz, 1H), 4.02 (brs, 2H), 3.70-3.71 (m, 2H), 3.63 (s, 3H), 3.26-3.28 (m, obscure 2H), 3.08-3.11 (m, 3H), 2.67-2.71 (m, 4H), 2.47-2.49 (m, 4H), 2.04-2.1 (m, 2H), 1.708-1.878 (m, 8H), 1.21-1.38 (m, 3H), 0.95-1.03 (m, 2H).

Example 30: Synthesis of N-cyclohexylmethyl-N-{2-[3-endo-(3-hydroxy-phenyl)-8-azabicyclo[3.2.1]oct-8-yl]ethyl}-2-methanesulfonylacetamide To a solution of methanesulfonylacetic acid (0.10 mmol) in dimethylformamide (0.2 mL) at room temperature was added 1,1'-carbonyldiimidazole (21 mg, 0.13 mmol). The reaction mixture was shaken for about one hour before a mixture of the TFA salt of 3-endo-{8-[2-(cyclohexylmethylamino)-ethyl]-8-azabicyclo[3.2.1]oct-3-yl-phenol (prepared by the method of Preparations 1 and 3) (30 mg, 0.053 mmol) and N,N-diisopropylethylamine (0.10 mmol) in dimethylformamide (0.3 mL) was added. The resulting mixture was stirred at room temperature overnight, concentrated, diluted with 50% acetic acid in water (8 mL), filtered, and purified by reversed phase preparative HPLC to give the TFA salt of the title compound (7.5 mg). (m/z): [M+H]⁺ calcd for $C_{25}H_{38}N_2O_4S$, 463.27; found 463.5.

Example 31: Synthesis of N-cyclohexylmethyl-N-{2-[3-endo-(3-hydroxy-phenyl)-8-azabicyclo[3.2.1]oct-8-yl]ethyl}succinamide To a solution of N-cyclohexylmethyl-N-{2-[3-(3-hydroxyphenyl)-8-aza-bicyclo[3.2.1]oct-8-yl]ethyl}succinamic acid, the product of Example 18 (95 mg, 0.17 mmol) in dimethylacetamide (0.2 mL) at room temperature was added 1,1'-carbonyldiimidazole (165 mg, 1.02 mmol). One hour later, ammonium acetate (79 mg, 1.02 mmol) was added followed by N,N-diisopropylethylamine (132 mg, 1.02 mmol). The resulting mixture was shaken at room temperature overnight, dissolved in 50% acetic acid in water (10 mL), filtered, and purified by reversed phase preparative HPLC to give the TFA salt of the title compound (5.6 mg). (m/z): [M+H]⁺ calcd for $C_{26}H_{39}N_3O_3$, 442.31; found 442.5.

Example 32: Synthesis of 1-cyclohexylmethyl-3-(3,4-dimethoxyphenyl)-1-{2-[3-endo-(3-hydroxyphenyl)-8-azabicyclo[3.2.1]oct-8-yl]ethyl}urea To a solution of the TFA salt of 3-endo-{8-[2-(cyclohexylmethylamino)-ethyl]-8-azabicyclo[3.2.1]oct-3-yl-phenol prepared by the method of Preparations 1 and 3 (30 mg, 0.05 mmol) in dimethylformamide (0.2 mL) at room temperature was added N,N-diisopropylethylamine (27 mg, 0.21 mmol) followed by 3,4-dimethoxyphenyl isocyanate (14 mg, 0.078 mmol). The resulting mixture was allowed to stand at room temperature overnight, concentrated by rotary evaporation, redissolved in 50% acetic acid in water (1.5 mL), filtered, and purified by preparative HPLC to give the TFA salt of the title compound (13.5 mg). (m/z): [M+H]⁺ calcd for $C_{31}H_{43}N_3O_4$, 522.34; found 522.2.

Examples 33-38

Using the general method of Example 7, except replacing the cyclohexylamine intermediate with the appropriate substituted benzylamine prepared as in Preparation 3, using the 3-endo-(8-aza-bicyclo[3.2.1]oct-3-yl)-phenol intermediate prepared as in Preparation 1, and replacing the acetylchloride with the appropriate acyl chloride, the TFA salts of the compounds of Examples 33-38 were prepared.

Example 33

N-(3-fluorobenzyl)-2-hydroxy-N-{2-[3-endo-(3-hydroxyphenyl)-8-azabicyclo[3.2.1]oct-8-yl]ethyl}acetamide (9.6 mg) (m/z): [M+H]⁺ calcd for $C_{24}H_{29}FN_2O_3$, 413.23; found 413.2.

Example 34

N-(3-fluorobenzyl)-2-hydroxy-N-{2-[3-endo-(3-hydroxyphenyl)-8-azabicyclo[3.2.1]oct-8-yl]-ethyl} succinamic acid (12.0 mg) (m/z): [M+H]⁺ calcd for $C_{26}H_{31}FN_2O_4$, 455.24; found 455.2.

Example 35

N-(3-fluorobenzyl)-N-{2-[3-endo-(3-hydroxyphenyl)-8-aza-bicyclo[3.2.1]oct-8-yl]ethyl}-3-methylbutyramide (9.9 mg) (m/z): [M+H]⁺ calcd for $C_{27}H_{35}FN_2O_2$, 439.28; found 439.2.

Example 36

N-(2,6-difluorobenzyl)-2-hydroxy-N-{2-[3-endo-(3-hydroxyphenyl)-8-aza-bicyclo[3.2.1]oct-8-yl]ethyl}acetamide (9.0 mg) (m/z): [M+H]⁺ calcd for $C_{24}H_{28}F_2N_2O_3$, 431.22; found 431.2.

Example 37

N-(2,6-difluorobenzyl)-N-{2-[3-endo-(3-hydroxyphenyl)-8-aza-bicyclo[3.2.1]oct-8-yl]ethyl}-3-methylbutyramide (13.1 mg) (m/z): [M+H]⁺ calcd for $C_{27}H_{34}F_2N_2O_2$, 457.27; found 457.2.

Example 38

N-(2,6-difluorobenzyl)-N-{2-[3-endo-(3-hydroxyphenyl)-8-aza-bicyclo[3.2.1]oct-8-yl]ethyl}acetamide (11.7 mg) (m/z): [M+H]⁺ calcd for $C_{24}H_{28}F_2N_2O_2$, 415.22; found 415.2.

Examples 39-42

Using the general method of Example 21, except replacing the cyclohexylamine intermediate with the appropriate substituted benzylamine prepared as in Preparation 3, using the 3-endo-(8-aza-bicyclo[3.2.1]oct-3-yl)-phenol intermediate prepared as in Preparation 1, and replacing the malonic acid mono tert-butyl ester with methanesulphonyl acetic acid in Examples 40 and 42, the TFA salts of the compounds of Examples 39-42 were prepared.

Example 39

N-(3-fluorobenzyl)-N-{2-[3-endo-(3-hydroxyphenyl)-8-azabicyclo[3.2.1]oct-8-yl]-ethyl}malonamic acid (11.4 mg) (m/z): [M+H]$^+$ calcd for $C_{25}H_{29}FN_2O_4$, 441.22; found 441.2.

Example 40

N-(3-fluorobenzyl)-N-{2-[3-endo-(3-hydroxyphenyl)-8-aza-bicyclo[3.2.1]oct-8-yl]ethyl}-2-methanesulfonyl-acetamide (25.0 mg) (m/z): [M+H]$^+$ calcd for $C_{25}H_{31}FN_2O_4S$, 475.21; found 475.2.

Example 41

N-(2,6-difluorobenzyl)-N-{2-[3-endo-(3-hydroxyphenyl)-8-aza-bicyclo[3.2.1]oct-8-yl]ethyl}malonamic acid (11.1 mg) (m/z): [M+H]$^+$ calcd for $C_{25}H_{28}F_2N_2O_4$, 459.21; found 459.2.

Example 42

N-(2,6-difluorobenzyl)-N-{2-[3-endo-(3-hydroxyphenyl)-8-aza-bicyclo[3.2.1]oct-8-yl]ethyl}-2-methanesulfonyl-acetamide (11.1 mg) (m/z): [M+H]$^+$ calcd for $C_{25}H_{30}F_2N_2O_4S$, 493.20; found 493.2.

Example 43: Synthesis of N-(4-fluorobenzyl)-2-hydroxy-N-{2-[3-endo-(3-hydroxyphenyl)-8-aza-icyclo [3.2.1]oct-8-yl]ethyl}acetamide To a solution of the bis TFA salt of 3-endo-{8-[2-(4-fluorobenzylamino)ethyl]-8-azabicyclo[3.2.1]oct-3-yl}-phenol, prepared by the methods of Preparations 4 and 3 (30 mg, 0.05 mmol) in dichloromethane (0.2 mL) at room temperature was added N,N-diisopropylethylamine (26 mg, 0.2 mmol) followed by acetoxyacetyl chloride (0.075 mmol). After the reaction went to completion as indicated by mass spectrometric analysis, the mixture was concentrated by rotary evaporation and the residues were dissolved in EtOH (0.2 mL) and hydrolyzed with lithium hydroxide monohydrate (17 mg) in water (0.2 mL) at room temperature for 30 minutes. Solvents were removed by rotary evaporation and the resulting residue was dissolved in 50% acetic acid in water (1.5 mL), filtered and purified by preparative HPLC to give the TFA salt of the title compound (16.6 mg). (m/z): [M+H]$^+$ calcd for $C_{24}H_{29}FN_2O_3$, 413.23; found 413.2.

Example 44: Synthesis of N-(4-chlorobenzyl)-2-hydroxy-N-{2-[3-endo-(3-hydroxyphenyl)-8-aza-icyclo [3.2.1]oct-8-yl]ethyl}acetamide Following the procedure of Example 43, using the appropriate substituted benzylamine of Preparation 3, the TFA salt of the title compound (19.1 mg) was obtained. (m/z): [M+H]$^+$ calcd for $C_{24}H_{29}ClN_2O_3$, 429.20; found 429.2.

Example 45: Synthesis of 2-hydroxy-N-{2-[3-endo-(3-hydroxyphenyl)-8-aza-bicyclo[3.2.1]oct-8-yl]-ethyl}-N-(4-trifluoromethylbenzyl)acetamide Following the procedure of Example 43, using the substituted benzylamine prepared according to Preparation 11, the TFA salt of the title compound (19.5 mg) was obtained.

(m/z): [M+H]$^+$ calcd for $C_{25}H_{29}F_3N_2O_3$, 463.22; found 463.2.

Example 46A: Synthesis of 3-endo-(8-{2-[benzyl-(2-hydroxyacetyl)-amino]ethyl}-8-azabicyclo[3.2.1]oct-3-yl)benzamide To a solution of the bis TFA salt of 3-endo-[8-(2-benzylaminoethyl)-8-aza-bicyclo[3.2.1]oct-3-yl]benzamide, prepared by the method of Preparations 5 and 6 (111 mg, 0.188 mmol) in dichloromethane (0.94 mL) at −20° C. was added N,N-diisopropylethylamine (97 mg, 0.75 mmol) followed by acetoxyacetylchloride (27 mg, 0.29 mmol) in dichloromethane (0.5 mL). The reaction mixture was stirred at −20° C. to −10° C. for about 30 minutes before it was quenched with saturated sodium bicarbonate and then extracted with DCM. The organic layer was washed with brine, dried over sodium sulfate, filtered and concentrated to give a yellowish oil which was dissolved in EtOH (1.0 mL) and treated with lithium hydroxide monohydrate (24 mg, 0.56 mmol) in water (0.5 mL) at room temperature for 30 minutes. The solvents were removed by rotary evaporation and the resulting residue was dissolved in 50% acetic acid in water (10 mL), filtered, and purified by preparative HPLC to give the TFA salt of the title compound (58.7 mg). (m/z): [M+H]$^+$ calcd for $C_{25}H_{31}N_3O_3$, 422.25; found 422.3.

Example 46B: Synthesis of 3-endo-(8-{2-[benzyl-(2-hydroxyacetyl)-amino]ethyl}-8-azabicyclo[3.2.1]oct-3-yl)benzamide To a solution of 3-endo-(8-azabicyclo[3.2.1]oct-3-yl)benzamide, prepared by the method of Preparation 13 (102 mg, 0.44 mmol) in dichloromethane (2 mL) at ambient temperature was added a solution of acetic acid [benzyl-(2-oxo-ethyl)carbamoyl] methyl ester (164 mg, 0.66 mmol) in dichloromethane (2 mL) followed by sodium triacetoxyborohydride (131 mg). The reaction mixture was stirred at ambient temperature for about thirty minutes and judged complete by mass spectrometric analysis. The reaction was then concentrated and redissolved in EtOH (6 mL) and treated with lithium hydroxide monohydride (111 mg) in water (4 mL) for about thirty minutes. Then, the mixture was concentrated, redissolved in 50% acetic acid in water (10 mL), filtered, and purified by reverse phase preparative HPLC to give the TFA salt of the title compound (115.7 mg). (m/z): [M+H]$^+$ calcd for $C_{25}H_{31}N_3O_3$, 422.25; found 422.4; $^1$H NMR (CD$_3$OD, 300 MHz) δ (ppm) 8.0 (s, 1H), 7.68-7.75 (m, 2H), 7.26-7.47 (m, 6H), 4.57 (s, 2H), 4.37 (s, 2H), 4.08 (brs, 2H), 3.72 (t, J=5.7 Hz, 2H), 3.05 (t, J=5.4 Hz, 2H), 2.59-2.62 (m, 4H), 1.99-2.03 (m, 2H), 1.74-1.81 (m, 2H).

Example 47: Synthesis of N-{2-[3-endo-(3-carbamoylphenyl)-8-aza-bicyclo[3.2.1]oct-8-yl]ethyl}-N-cyclohexylmethyl-succinamic Acid To a solution of the bis TFA salt of 3-endo-{8-[2-(cyclohexylmethylamino)ethyl]-8-aza-bicyclo[3.2.1]oct-3-yl}benzamide prepared by the method of Preparations 5 and 7 (114 mg, 0.19 mmol) in dichloromethane (0.95 mL) at room temperature was added N,N-diisopropylethyl amine (98 mg, 0.76 mmol). The resulting mixture was then cooled to −30° C. before a solution of 3-carbomethoxypropionyl chloride (30 mg, 0.20 mmol) in DCM (0.5 mL) was added. After the reaction went to completion, the mixture was concentrated. The residue was redissolved in EtOH (2 mL)

and treated with lithium hydroxide monohydrate (32 mg) in water (1 mL) for about 30 minutes. The mixture was concentrated, dissolved in 50% acetic acid in water (10 mL), filtered and purified by reversed phase preparative HPLC to give the TFA salt of the title compound (63.2 mg). (m/z): [M+H]$^+$ calcd for $C_{27}H_{39}N_3O_4$, 470.30; found 470.5.

Example 48: Synthesis of 3-endo-(8-{2-[cyclohexylmethyl-(2-hydroxyacetyl)-amino]-ethyl}-8-azabicyclo[3.2.1]oct-3-yl)benzamide To a solution of the bis TFA salt of 3-endo-{8-[2-(cyclohexylmethylamino)ethyl]-8-aza-bicyclo[3.2.1]oct-3-yl}benzamide prepared by the method of Preparations 13 and 9 (734 mg, 1.23 mmol) in dichloromethane (5 mL) at room temperature was added N,N-diisopropylethyl amine (635 mg, 4.9 mmol). The resulting mixture was cooled to −20° C. before a solution of acetoxyacetyl chloride (184 mg, 1.35 mmol) in DCM (2 mL) was added. Five minutes later, the reaction went to completion as confirmed by mass spectrometric analysis. The reaction mixture was concentrated, dissolved in EtOH (15 mL) and treated with lithium hydroxide monohydrate (309 mg) in water (5 mL) for about 30 minutes. The reaction mixture was then concentrated, dissolved in 50% acetic acid in water (15 mL), filtered and purified by reversed phase preparative HPLC to give the TFA salt of the title compound (585.9 mg). (m/z): [M+H]$^+$ calcd for $C_{25}H_{37}N_3O_3$, 428.29; found 428.2. $^1$H NMR (CD$_3$OD, 300 MHz) δ (ppm): 8.0 (s, 1H), 7.68-7.74 (m, 2H), 7.42-7.47 (t, J=8.1 Hz, 1H), 4.27 (s, 2H), 4.09 (brs, 2H), 3.72 (t, J=5.7 Hz, 2H), 3.2-3.35 (m, obscure 1H), 3.09-3.14 (m, 4H), 2.59-2.62 (m, 4H), 2.07-2.12 (m, 2H), 1.62-1.83 (m, 8H), 1.15-1.35 (m, 3H), 0.87-1.16 (m, 2H).

Example 49: Synthesis of 3-endo-{8-[2-(cyclohexylmethyl-phenylacetylamino)-ethyl]-8-azabicyclo[3.2.1]oct-3-yl}benzamide To a solution of the bis TFA salt of 3-endo-{8-[2-(cyclohexylmethylamino)ethyl]-8-aza-bicyclo[3.2.1]oct-3-yl}benzamide prepared by the method of Preparations 5 and 7 (112 mg, 0.19 mmol) in dichloromethane (1 mL) at room temperature was added N,N-diisopropylethyl amine (97 mg, 0.75 mmol). The resulting mixture was then cooled to −40° C. before a solution of phenylacetyl chloride (32 mg, 0.21 mmol) in DCM (0.1 mL) was added. The resulting mixture was stirred at a temperature between −40° C. to −20° C. for about 30 minutes. The reaction was judged complete according to mass spectrometric analysis. After concentration, the residue was redissolved in 50% acetic acid in water (10 mL), filtered and purified by reversed phase preparative HPLC to give the TFA salt of the title compound (27.5 mg). (m/z): [M+H]$^+$ calcd for $C_{31}H_{41}N_3O_2$, 488.33; found 488.8.

Example 50: Synthesis of N-{2-[3-endo-(3-carbamoyl-phenyl)-8-aza-bicyclo[3.2.1]oct-8-yl]ethyl}-N-cyclohexylmethyl-succinamic Acid Methyl Ester To a solution of the bis TFA salt of 3-endo-{8-[2-(cyclohexylmethylamino)ethyl]-8-aza-bicyclo[3.2.1]oct-3-yl}benzamide prepared by the method of Preparations 5 and 7 (97 mg, 0.16 mmol) in dichloromethane (0.8 mL) at room temperature was added N,N-diisopropylethylamine (83 mg, 0.64 mmol). The resulting mixture was then cooled to −20° C. before a solution of 3-carbomethoxypropionyl chloride (29 mg, 0.19 mmol) in DCM (0.1 mL) was added. followed by another portion of 3-carbomethoxypropionyl chloride (0.20 mmol) in DCM (0.3 mL). After 30 minutes, LC-MS analysis of an aliquot showed desired molecular weight. The reaction mixture was then concentrated, redissolved in 50% acetic acid in water (8 mL), filtered, and purified by reversed phase preparative HPLC to give the TFA salt of the title compound as a white solid (46.4 mg). (m/z): [M+H]$^+$ calcd for $C_{28}H_{41}N_3O_4$, 484.32; found 484.5.

Example 51: Synthesis of 3-endo-{8-[2-(3-sec-butyl-1-cyclohexylmethyl-ureido)ethyl]-8-azabicyclo[3.2.1]oct-3-yl}benzamide Following the method of Example 32, the bis TFA salt of 3-endo-{8-[2-(cyclohexylmethylamino)ethyl]-8-aza-bicyclo[3.2.1]oct-3-yl}benzamide prepared by the method of Preparations 5 and 9 (30 mg, 0.05 mmol) was reacted with sec-butylisocyanate (0.075 mmol). Purification yielded the TFA salt of the title compound (24.2 mg). (m/z): [M+H]$^+$ calcd for $C_{28}H_{44}N_4O_2$, 469.35; found 469.4.

Example 52: Synthesis of 3-endo-{8-[2-(1-cyclohexylmethyl-3-pentylureido)-ethyl]-8-azabicyclo[3.2.1]oct-3-yl}benzamide To a solution of the bis TFA salt of 3-endo-{8-[2-(cyclohexylmethylamino)ethyl]-8-aza-bicyclo[3.2.1]oct-3-yl}benzamide prepared by the method of Preparations 5 and 9 (30 mg, 0.05 mmol) in DMF (0.4 mL) at room temperature was added N,N-diisopropylethylamine (27 mg, 0.20 mmol) followed by pentylisocyanate (0.075 mmol). The resulting mixture was shaken at room temperature overnight, concentrated, dissolved in 50% acetic acid in water (1.5 mL), filtered, and purified by preparative HPLC to provide the TFA salt of the title compound (23.3 mg). (m/z): [M+H]$^+$ calcd for $C_{29}H_{46}N_4O_2$, 483.37; found 483.4.

Examples 53-55

Using the general method of Example 52, replacing the pentylisocyanate with the appropriate isocyanate, the TFA salts of the compounds of Examples 53-55 were prepared.

Example 53

3-endo-(8-{2-[1-cyclohexylmethyl-3-(4-fluorobenzyl)-ureido]ethyl}-8-azabicyclo[3.2.1]oct-3-yl)benzamide (30.3 mg) (m/z): [M+H]$^+$ calcd for $C_{31}H_{41}FN_4O_2$, 521.33; found 521.2.

Example 54

3-endo-{8-[2-(3-benzo[1,3]dioxol-5-yl-1-cyclohexylmethylureido)ethyl]-8-azabicyclo[3.2.1]oct-3-yl}benzamide (24.5 mg) (m/z): [M+H]$^+$ calcd for $C_{31}H_{40}N_4O_4$, 533.31; found 533.2; $^1$H NMR (CD$_3$OD, 300 MHz) δ (ppm) 7.97 (s, 1H), 7.71 (d, J=7.8 Hz, 1H), 7.66 (d, J=8.1 Hz, 1H), 7.42 (dd, J=7.8 Hz, 1H), 3.90-3.99 (m, 3H), 3.60 (t, J=4.8 Hz, 2H), 3.25-3.29 (m, 1H, overlap with solvent), 3.02-3.09 (m, 4H), 2.55-2.58 (m, 4H), 2.03-2.07 (m, 2H), 1.63-1.78 (m, 8H), 1.07-1.25 (m, 9H), 0.92-1.01 (m, 2H).

Example 55

3-endo-{8-[2-(1-cyclohexylmethyl-3-isopropylureido)ethyl]-8-aza-bicyclo[3.2.1]oct-3-yl}benzamide (24.5 mg) (m/z): [M+H]$^+$ calcd for $C_{27}H_{42}N_4O_2$, 455.33; found 455.4; $^1$H NMR (CD$_3$OD, 300 MHz) δ (ppm) 7.97 (s, 1H), 7.71 (d, J=7.8 Hz, 1H), 7.66 (d, J=8.1 Hz, 1H), 7.42 (dd, J=7.8 Hz, 1H), 3.90-3.99 (m, 3H), 3.60 (t, J=4.8 Hz, 2H), 3.25-3.29 (m, 1H, overlap with solvent), 3.02-3.09 (m, 4H), 2.55-2.58 (m, 4H), 2.03-2.07 (m, 2H), 1.63-1.78 (m, 8H), 1.07-1.25 (m, 9H), 0.92-1.01 (m, 2H).

Example 56: Synthesis of 3-endo-(8-{2-[cyclohexylmethyl-(2-methanesulfonyl-acetyl)amino]ethyl}-8-aza-bicyclo[3.2.1]oct-3-yl)benzamide To a solution of methanesulfonylacetic acid (90 mg, 0.65 mmol) in DMF (0.2 mL) was added 1,1'-carbonyldiimidazole (105 mg, 0.65 mmol). One hour later, 3-endo-{8-[2-(cyclohexylmethylamino)ethyl]-8-aza-bicyclo[3.2.1]oct-3-yl}benzamide prepared by the method of Preparations 12 and 9 (60 mg, 0.16 mmol) was added followed by N,N-diisopropylethylamine (84 mg, 0.65 mmol). The resulting mixture was heated to 60° C. for two hours then cooled down to room temperature for 60 h. Then it was concentrated, dissolved in 50% acetic acid in water (3 mL), filtered and purified by preparative HPLC to give the TFA salt of the title compound (35.1 mg). (m/z): $[M+H]^+$ calcd for $C_{26}H_{39}N_3O_4S$, 490.27; found 490.2. $^1H$ NMR ($CD_3OD$, 300 MHz) δ (ppm): 7.98 (s, 1H), 7.66-7.74 (m, 2H), 7.41-7.46 (m, 1H), 4.77 (s, 2H), 4.38 (brs, 2H), 3.78-3.82 (m, 2H), 3.04-3.33 (m, obscure 5H), 3.21 (s, 3H), 2.57-2.61 (m, 4H), 2.07-2.10 (m, 2H), 1.66-1.79 (m, 8H), 1.22-1.29 (m, 3H), 0.94-1.01 (m, 2H).

Example 57: Synthesis of 3-endo-(8-{2-[(2-aminoacetyl)-cyclohexylmethyl-amino]ethyl}-8-aza-bicyclo [3.2.1]oct-3-yl)benzamide To a solution of n-tert-butoxycarbonylglycine (34 mg, 0.20 mmol) in DMF (0.2 mL) at room temperature was added 1,1'-carbonyldiimidazole (32 mg, 0.2 mmol). After shaking at room temperature for 2 hours, to this mixture was added the bis TFA salt of 3-endo-{8-[2-(cyclohexylmethylamino)ethyl]-8-azabicyclo[3.2.1]oct-3-yl}benzamide prepared by the method of Preparations 12 and 9 (30 mg, 0.05 mmol) and N,N-diisopropylethylamine (26 mg, 0.2 mmol). The resulting reaction mixture was shaken at room temperature overnight. After concentration, the residue was treated with 50% TFA in DCM (1 mL). The mixture was concentrated and the residue was dissolved in 50% acetic acid in water (1.5 mL), filtered and purified by reversed phase preparative HPLC to give the bis TFA salt of the title compound (15.9 mg). (m/z): $[M+H]^+$ calcd for $C_{25}H_{38}N_4O_2$, 427.31; found 427.2.

Example 58A: Synthesis of 3-endo-(8-{2-[cyclohexylmethyl-((S)-2,3-dihydroxy-propionyl)amino]ethyl}-8-aza-bicyclo[3.2.1]oct-3-yl)benzamide To a solution of (S)-2,2-dimethyl-[1,3]dioxolane-4-carboxylic acid (98 mg, 0.67 mmol) in DMF (0.2 mL) at room temperature was added 1,1'-carbonyldiimidazole (109 mg, 0.67 mmol). After being stirred at room temperature for one hour, to this mixture was added the bis TFA salt of 3-endo-{8-[2-(cyclohexylmethylamino)ethyl]-8-azabicyclo[3.2.1] oct-3-yl}benzamide prepared by the method of Preparations 12 and 9 (100 mg, 0.167 mmol) and N,N-diisopropylethylamine (87 mg, 0.67 mmol). The reaction mixture was heated at 60° C. for two hours and then at room temperature for 72 hours. The mixture was diluted with water and extracted with ethyl acetate. The organic layer was sequentially washed with water (2×2 mL), 1N NaOH (2 mL), brine (2 mL), dried over sodium sulfate, filtered, and concentrated. The resulting residue was then dissolved in acetic acid (1.5 mL) and water (0.5 mL) and heated to 65° C. overnight. The mixture was concentrated by rotary evaporation, redissolved in 50% acetic acid in water (3.0 mL), filtered and purified by reversed phase preparative HPLC to give the TFA salt of the title compound (15.5 mg). (m/z): $[M+H]^+$ calcd for $C_{26}H_{39}N_3O_2$, 458.30; found 458.2. $^1H$ NMR ($CD_3OD$, 300M Hz) δ (ppm): 7.98 (s, 1H), 7.67-7.73 (m, 2H), 7.40-7.45 (m, 1H), 4.57 (t, J=5.4 Hz, 1H), 3.94-4.12 (m, 3H), 3.69-3.72 (m, 2H), 3.50-3.58 (m, 1H), 3.35-3.43 (m, 1H), 3.20-3.27 (obscure 2H, partially overlap with solvent), 3.12-3.15 (m, 2H), 2.52 (brs, 4H), 1.98-2.02 (m, 2H), 1.61-1.70 (m, 8H), 1.09-1.22 (m, 3H), 0.88-0.95 (m, 2H).

The TFA salt of the title compound (4.45 g, 7.78 mmol), prepared by the method described above using as reagents 3-endo-{8-[2-(cyclohexylmethylamino)ethyl]-8-azabicyclo [3.2.1]oct-3-yl}benzamide, prepared by the method of Preparations 13 and 9, and lithium (4S)-2,2-dimethyl-1,3-dioxolane-4-carboxylate, was dissolved in methanol (<10 mL) and diluted with DCM (400 mL). The organic solution was washed with 1M NaOH (500 mL). The basic aqueous layer was extracted with DCM (2×150 mL). Combined organic layers were washed with saturated aqueous sodium chloride (500 mL). The organic layer was dried over potassium carbonate. The solution was filtered and solvent was removed in vacuo to give the title compound (3.09 g, 87% yield) as a glassy solid. (m/z): $[M+H]^+$ calcd for $C_{26}H_{39}N_3O_2$, 458.30; found 458.5. $^1H$ NMR (300 mHz, $d_6$-DMSO): 7.81-7.83 (s, 1H), 7.61-7.65 (br s, 1H), 7.55-7.60 (d, 1H), 7.30-7.35 (d, 1H), 7.18-7.22 (m, 2H), 4.80-4082 (d, 0.8H), 4.62-4.65 (d, 0.64H), 4.50-4.60 (m, 1.1H), 4.22-4.38 (m, 0.83H), 4.10-4.20 (m, 0.65H), 3.00-3.50 (m, 8H), 2.70-2.99 (m, 2H), 2.00-2.30 (m, 4H), 1.60-1.80 (m, 2H), 1.43-1.60 (m, 4H), 1.22-1.40 (m, 3H), 0.93-1.19 (m, 3H), 0.82-0.94 (m, 2H).

Example 58B: Synthesis of crystalline 3-endo-(8-{2-[cyclohexylmethyl-((S)-2,3-dihydroxy-propionyl) amino]ethyl}-8-aza-bicyclo[3.2.1]oct-3-yl)benzamide Sulfate a. Preparation of N-cyclohexylmethyl-(2-oxoethyl)-carbamic Acid Benzyl Ester To a 100 mL flask was added N-cyclohexylmethyl-(2-oxoethyl)-carbamic acid benzyl ester bisulfite adduct (3.94 g, 1 mmol) and MeTHF (35 mL), followed by water (25 mL). The resulting slurry was stirred at room temperature for 5 min and 1 M NaOH (8 mL) was added. The reaction mixture was stirred at room temperature for 45 min. The layers were separated and the volume of the organic layer was reduced to ~8 mL to provide the crude title intermediate.

b. Preparation of 2-[3-endo-(3-carbamoylphenyl)-8-azabicyclo[3.2.1]oct-8-yl]-ethyl}cyclohexylmethyl-carbamic Acid Benzyl Ester To the product of the previous step was added DMF (15 mL) followed by 3-endo-(8-azabicyclo[3.2.1]oct-3-yl)-benzamide hydrochloride (2.67 g, 1 mmol), prepared by the process of Preparation 25 and then DMF (10 mL). The mixture was stirred at room temperature for 30 min, cooled to 10° C. and then sodium triacetoxyborohydride (4.25 g, 2 mmol) was added. The reaction mixture was stirred at room temperature for 90 min and then cooled to 10° C. Isopropyl acetate (100 mL) was added, followed by 1 M NaOH (50 mL). The mixture was stirred for 15 min, and the phases were separated. The organic layer was washed with brine in water (1:1, 2×50 mL) and the volume of the organic layer was reduced to ~10 mL to provide the crude title intermediate.

c. Preparation of 3-endo-{8-[2-(cyclohexylmethyl-amino)ethyl]-8-aza-bicyclo[3.2.1]oct-3-yl}benzamide To the product of the previous step was added EtOH (30 mL) and concentrated HCl (1.5 mL). The solution was purged with nitrogen, 10% palladium on carbon (470 mg) was added and the mixture was purged with nitrogen for 5 min and then hydrogenated at 30 psi overnight. After purging with nitrogen for 2 min, the solution was filtered through Celite and solvent was removed to ~10 mL. Isopropyl acetate (40 mL) and 1 M NaOH (20 mL) were added. The layers were separated and the organic layer was washed with brine (20 mL), phases were separated and organic solvent removed to 5-10 mL. Isopropyl acetate (20 mL) was added and the volume reduced to ~8 mL to which isopropyl acetate (20 mL) was added. The resulting slurry was stirred at room temperature for 2 h. The product was isolated by filtration, the reaction flask and filter cake were washed with isopropyl acetate (10 mL) to yield the title intermediate (2.4 g, 98% pure) as an off-white solid.

d. Preparation of 3-endo-(8-{2-[cyclohexylmethyl-((S)-2,3-dihydroxy-propionyl)amino]ethyl}-8-aza-bicyclo[3.2.1]oct-3-yl)benzamide Sulfate (Hydrate Form)

To a 500 mL flask was added 3-endo-{8-[2-(cyclohexyl-methylamino)ethyl]-8-aza-bicyclo[3.2.1]oct-3-yl}benzamide (31 g, 83.9 mmol) and DMF (150 mL). The mixture was stirred for 10 min and then benzotriazol-1-yloxytris(pyrrolidino)-phosphonium hexafluoro-phosphate (56.8 g, 109 mmol) and lithium (4S)-2,2-dimethyl-1,3-dioxolane-4-carboxylate (15.6 g, 92.3 mmol) were added and the mixture was stirred at room temperature for 2 h. Ethyl acetate (600 mL) and 0.5 M NaOH (300 mL) were added and the phases were separated. The organic layer contained crude (S)-2,2-dimethyl-[1,3]dioxolane-4-carboxylic acid {2-[3-(3-carbamoyl-phenyl)-8-azabicyclo[3.2.1]oct-8-yl]ethyl}cyclohexylmethyl-amide (~84 mmol) which was not isolated.

The organic layer was washed with brine in water (1:1, 2×300 mL) and the phases were separated. To the organic layer was added 2 M $H_2SO_4$ (42 mL) and the reaction mixture was stirred at room temperature overnight. Acetonitrile (300 mL) was added and the resulting slurry was stirred for 2-6 h. The product was isolated by filtration, the filter cake were washed with acetonitrile (200 mL), dried in air for 2 h and then under vacuum at room temperature for 20 h to provide the title compound (40 g, 97% pure by HPLC) as a white powder.

e. Synthesis of crystalline 3-endo-(8-{2-[cyclohex-ylmethyl-((S)-2,3-dihydroxy-propionyl)amino]ethyl}-8-aza-bicyclo[3.2.1]oct-3-yl)benzamide Sulfate To a 100 mL flask was added 3-endo-(8-{2-[cyclohexyl-methyl-((S)-2,3-dihydroxy-propionyl)amino]ethyl}-8-aza-bicyclo[3.2.1]oct-3-yl)benzamide sulfate hydrate form (2 g) and MeOH (40 mL). The resulting slurry was heated to 65° C. under nitrogen for 20 min resulting in complete dissolution. The solution was cooled to room temperature with stirring. About 20 mL of solvent was removed under slightly reduced pressure and the resulting slurry stirred at room temperature overnight. The product was isolated by filtration, and the flask and filter cake were washed with acetonitrile (2×5 mL). The filter cake was dried in air for 2 h and then under vacuum at room temperature overnight to provide the title compound (1.71 g, >99% pure by HPLC, ~85% yield) as a white powder.

A sample prepared according to the above procedure was characterized by $^1H$ NMR (400 MHz, DMSO $d_6$): δ (ppm) 9.08 & 8.94 (two sets of brs, 1H), 7.99-8.04 (m, 2H), 7.74-7.76 (m, 1H), 7.68-7.70 (m, 1H), 7.41-7.45 (m, 2H), 4.81, 5.00 and 5.30 (three sets of brs, 2H), 4.34 (deformed m, 1H), 4.00 & 4.05 (deformed m, 2H), 3.01-3.25 and 3.47-3.55 and 3.75-3.82 (three sets of m, 10H), 2.50-2.55 (m, 2H), 1.99 (deformed m, 2H), 1.56-1.70 (m, 8H), 1.15-1.19 (m, 3H), 0.89-0.99 (m, 2H).

Example 58C: Synthesis of Crystalline 3-endo-(8-{2-[cyclohexylmethyl-((S)-2,3-dihydroxy-propionyl)amino]ethyl}-8-aza-bicyclo[3.2.1]oct-3-yl)benzamide Glycolate 3-endo-(8-{2-[Cyclohexylmethyl-((S)-2,3-dihydroxy-propionyl)amino]ethyl}-8-aza-bicyclo[3.2.1]oct-3-yl)benzamide (35 mg) was dissolved in aqueous acetone (2% water, 98% acetone, 0.46 mL). To this solution was added 0.78 M glycolic acid in acetonitrile (0.10 mL). A precipitate formed rapidly and over 2 h converted to a birefringent material. The mother liquor was decanted and the remaining solid was dried to provide the title compound. The x-ray powder diffraction pattern (XRPD) of the crystalline material is shown in FIG. 1. Diffraction peaks were observed at 2θ values of 8.00±0.2, 12.50±0.2, 16.19±0.2, 16.91±0.2, 18.41±0.2, 20.69±0.2, 22.04±0.2, 23.03±0.2, 25.44±0.2, 25.85±0.2, and 28.76±0.2.

All XRPD data presented herein was obtained with a Rigaku diffractometer using Cu Kα (30.0 kV, 15.0 mA) radiation operating in continuous-scan mode of 3° per min with a step size of 0.03°.

Figure 2:
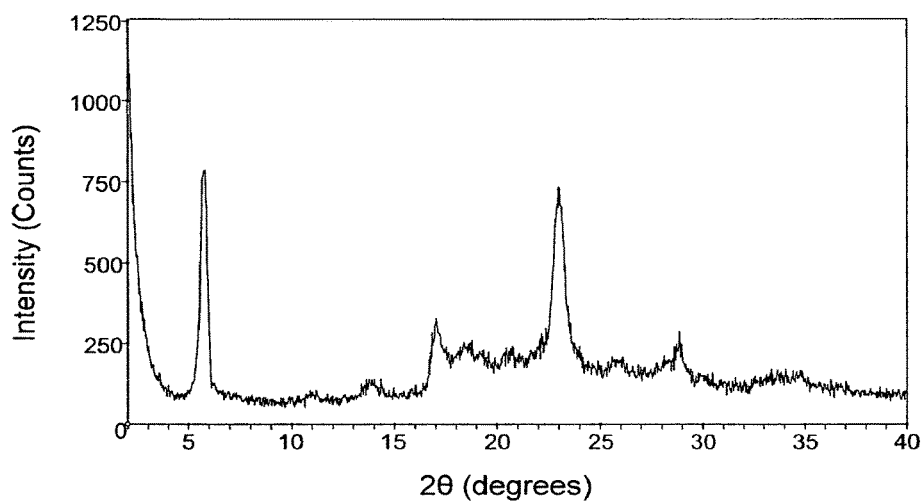
FIG. 2 shows an x-ray powder diffraction pattern of crystalline 3-endo-(8-{2-[cyclohexylmethyl-((S)-2,3-dihydroxy-propionyl)amino]ethyl}-8-azabicyclo[3.2.1]oct-3-yl)benzamide oxalate of the invention.

Example 58D: Synthesis of Crystalline 3-endo-(8-{2-[cyclohexylmethyl-((S)-2,3-dihydroxy-propionyl)amino]ethyl}-8-aza-bicyclo[3.2.1]oct-3-yl)benzamide Oxalate 3-endo-(8-{2-[Cyclohexylmethyl-((S)-2,3-dihydroxy-propionyl)amino]ethyl}-8-aza-bicyclo[3.2.1]oct-3-yl)benzamide (25.4 mg) was dissolved in acetone (0.34 mL). To this solution was added 0.4M oxalic acid in acetonitrile (0.14 mL) followed by water (0.24 mL). The resulting dispersion was sonicated for 30 seconds and then water (0.045 mL) and DCM (0.015 mL) was added. After 4 days, the title compound was recovered by vacuum filtration as a crystalline solid (19.8 mg). The XRPD of the crystalline material is shown in FIG. 2. Diffraction peaks were observed at 2θ values of 5.84±0.2, 13.80±0.2, 17.03±0.2, 23.00±0.2, and 28.85±0.2,

Example 59: Synthesis of 3-endo-(8-{2-[(2-hy-droxyacetyl)phenethylamino]-ethyl}-8-azabicyclo [3.2.1]oct-3-yl)benzamide The product of preparation 17 (~0.26 mmol) was dissolved in DCM (0.5 mL) and cooled to 0° C. The reaction mixture was treated with N,N-diisopropylethylamine (100 mg, 0.78 mmol) and then with acetoxy acetyl chloride (39 mg, 0.29 mmol). The reaction mixture was diluted with dichloromethane and washed with saturated sodium bicarbonate and brine. The organic layer was dried with sodium sulfate, filtered, and concentrated. The crude oil was dissolved in ethanol (1 mL) and treated with lithium hydroxide monohydrate (66 mg, 1.2 mmol) in water (0.5 mL). After an hour, the reaction mixture was concentrated and the residue was dissolved in 50% acetic acid in water (1.2 mL), filtered, and purified by preparative HPLC to give the TFA salt of the title compound (38.7 mg) (m/z): [M+H]$^+$ calcd for $C_{26}H_{33}N_3O_3$, 436.25; found 436.4.

Examples 60-62

Following the procedure of Example 59, substituting the product of Preparations 18, 19, and 20, respectively for the product of Preparation 17, the TFA salts of the compounds of Examples 60-62 were prepared.

Example 60

3-endo-(8-{2-[(2-hydroxyacetyl)-(3-phenylpropyl) amino]ethyl}-8-aza-bicyclo[3.2.1]oct-3-yl)benzamide (66.7 mg) (m/z): [M+H]$^+$ calcd for $C_{27}H_{35}N_3O_3$, 450.27; found 450.4.

Example 61

3-endo-(8-{2-[(2-cyclohexylethyl)-(2-hydroxyacetyl) amino]ethyl}-8-aza-bicyclo[3.2.1]oct-3-yl)-benzamide (68.6 mg) (m/z): [M+H]$^+$ calcd for $C_{26}H_{39}N_3O_3$, 442.30; found 442.6.

Example 62

3-endo-(8-{2-[(3-cyclohexylpropyl)-(2-hydroxyacetyl) amino]ethyl}-8-aza-bicyclo[3.2.1]oct-3-yl)-benzamide (37.1 mg) (m/z): [M+H]$^+$ calcd for $C_{27}H_{41}N_3O_3$, 456.31; found 456.4.

Example 63A: Synthesis of 3-endo-(8-{2-[(4,4-difluorocyclohexylmethyl)-(2-hydroxyacetyl)amino] ethyl}-8-azabicyclo[3.2.1]oct-3-yl)benzamide Following the procedure of Example 48, the product of Preparation 21, 3-endo-(8-{2-[(4,4-difluorocyclohexylmethyl)-amino]ethyl}8-azabicyclo[3.2.1]oct-3-yl)benzamide (72.5 mg, 1 eq) was treated with acetoxyacetyl chloride (1.3 eq), hydrolyzed, and purified by HPLC to provide the TFA salt of the title compound (14.4 mg). (m/z): [M+H]$^+$ calcd for $C_{25}H_{35}F_2N_3O_3$, 464.27; found 464.2.

Example 63B: Synthesis of 3-endo-(8-{2-[(4,4-difluorocyclohexylmethyl)-(2-hydroxyacetyl)amino] ethyl}-8-azabicyclo[3.2.1]oct-3-yl)benzamide To a solution of 3-endo-(8-azabicyclo[3.2.1]oct-3-yl)-benzamide prepared by the method of Preparation 13 (2.15 g, 9.34 mmol) in DCM (45.0 mL) at 0° C. was added acetic acid (0.56 g, 9.34 mmol) followed by a solution of acetic acid [(4,4-difluoro-cyclohexylmethyl)-(2-oxo-ethyl)-carbamoyl]-methyl ester (2.59 g, 8.9 mmol) in DCM (10.0 mL) and sodium triacetoxyborohydride (2.26 g, 10.7 mmol). The resulting mixture was stirred at 0° C. for 30 min and then diluted with DCM (40.0 mL). The organic layer was washed sequentially with saturated sodium bicarbonate (20.0 mL) and brine (20.0 mL), dried over sodium sulfate, filtered and concentrated to give acetic acid [{2-[3-endo-(3-carbamoyl-phenyl)-8-aza-bicyclo[3.2.1]oct-8-yl]-ethyl}-(4,4-difluoro-cyclohexylmethyl)carbamoyl] methyl ester as a light yellowish foam.

The product from the previous step was dissolved in methanol (20.0 mL) at ambient temperature and treated with lithium hydroxide monohydrate (0.56 g, 13.4 mmol) in water (5.0 mL) for 30 min. The reaction mixture was concentrated. The residue was dissolved in 25% acetic acid in water (48.0 mL), filtered and purified by reverse phase preparative HPLC. Desired fractions were combined and freeze dried to give the title compound as its TFA salt (2.1 g). $^1$H NMR (CD$_3$OD, 300 MHz) δ (ppm) 8.07 (s, 1H), 7.75-7.81 (m, 2H), 7.48-(dd, J=7.8 Hz, 1H), 4.35 (s, 2H), 4.17 (brs, 2H), 3.81 (t, J=6.0 Hz, 2H), 3.35-3.38 (obscure, 1H, overlap with solvent), 3.25 (d, J=6.9 Hz, 2H), 3.20 (t, J=5.4 Hz, 2H), 2.66-2.72 (m, 4H), 2.10-2.19 (m, 4H), 1.77-1.90 (m, 7H), 1.33-1.41 (m, 2H).

Figure 3:
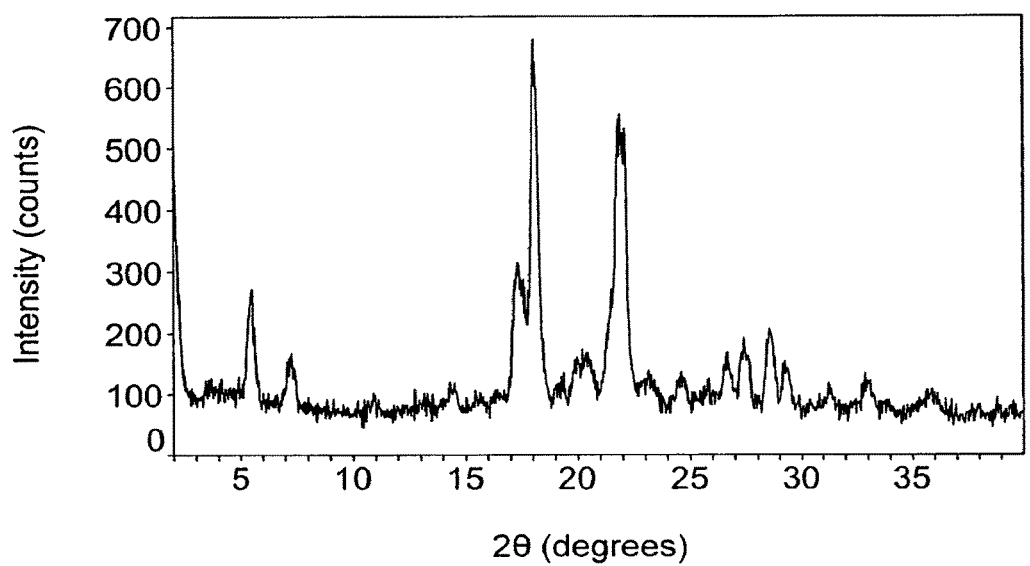
FIG. 3 shows an x-ray powder diffraction pattern of crystalline 3-endo-(8-{2-[(4,4-difluorocyclohexylmethyl)-(2-hydroxyacetyl)amino]ethyl}-8-azabicyclo[3.2.1]oct-3-yl)benzamide phosphate of the invention.

Example 63C: Synthesis of crystalline 3-endo-(8-{2-[(4,4-difluorocyclohexylmethyl)-(2-hydroxyacetyl)amino]ethyl}-8-azabicyclo[3.2.1]oct-3-yl) benzamide phosphate In a 4 mL glass vial at room temperature, 3-endo-(8-{2-[(4,4-difluorocyclohexylmethyl)-(2-hydroxyacetyl)amino] ethyl}-8-azabicyclo[3.2.1]oct-3-yl)benzamide (20 mg) was dissolved in methanol (0.172 mL). To this solution was added 1.0 M phosphoric acid in methanol (0.043 mL) and acetone (0.228 mL). The mixture was gently stirred for 16 h at room temperature. The title compound was recovered by vacuum filtration as a crystalline powder (13.4 mg). The XRPD of the crystalline material is shown in FIG. 3. Diffraction peaks were observed at 2θ values of 5.51±0.20, 7.27±0.20, 17.30±0.20, 18.05±0.20, 19.94±0.20, 20.39±0.20, 21.89±0.20, 24.62±0.20, 26.66±0.20, 27.38±0.20, 28.52±0.20, 29.21±0.20, and 32.87±0.20.

Examples 64 to 74

A solution of the product of Preparation 22, 3-endo-[8-(2-benzylamino-propyl)-8-aza-bicyclo[3.2.1]oct-3-yl]-phenol (509 mg, 1.45 mmol) and N,N-diisopropylethylamine (0.76 mL) in dichloromethane (12 mL) was dispensed in 12 equal portions into vials each containing an appropriate acid chloride (0.16 mmol). The vials were shaken at room temperature for 45 minutes and then concentrated in vacuo. Each residue was dissolved in ethanol (1 mL) and a solution of lithium hydroxide (6 eq.) in water (0.2 mL) was added and the vials shaken at 40° C. for 30 minutes. The contents of the vials were concentrated in vacuo, diluted with acetic acid:water 1:1 (1 mL), filtered and purified by preparative HPLC to afford the TFA salts of the compounds of Examples 64 to 74.

Example 64 cyclopropanecarboxylic acid (R)-benzyl-{2-3-endo-(3-hydroxyphenyl)-8-azabicyclo[3.2.1]oct-8-yl]-1-methylethyl}amide (7.9 mg) (m/z): [M+H]$^+$ calcd for $C_{27}H_{34}N_2O_2$, 419.26; found 419.2.

Example 65

N-benzyl-3-cyclopentyl-N—{(R)-2-[3-endo-(3-hydroxyphenyl)-8-aza-bicyclo[3.2.1]oct-8-yl]-1-methylethyl}propionamide (1.9 mg) (m/z): [M+H]$^+$ calcd for $C_{31}H_{42}N_2O_2$, 475.32; found 475.2.

Example 66

N-benzyl-N—{(R)-2-[3-endo-(3-hydroxyphenyl)-8-azabicyclo[3.2.1]oct-8-yl]-1-methyl-ethyl}-2-phenylacetamide (3.9 mg) (m/z): [M+H]$^+$ calcd for $C_{31}H_{36}N_2O_2$, 469.28; found 469.2.

Example 67

N-benzyl-N—{(R)-2-[3-endo-(3-hydroxyphenyl)-8-azabicyclo[3.2.1]oct-8-yl]-1-methy-ethyl}-3-methylbutyramide (6.5 mg) (m/z): [M+H]$^+$ calcd for $C_{28}H_{38}N_2O_2$, 435.29; found 435.2.

Example 68

N-benzyl-N—{(R)-2-[3-endo-(3-hydroxyphenyl)-8-azabicyclo[3.2.1]oct-8-yl]-1-methy-ethyl}-3-methylbutyramide (3.5 mg) (m/z): [M+H]$^+$ calcd for $C_{25}H_{32}N_2O_3$, 409.24; found 409.2.

Example 69

N-benzyl-2-cyclopentyl-N—{(R)-2-[3-endo-(3-hydroxyphenyl)-8-azabicyclo[3.2.1]oct-8-yl]-1-methylethyl}acetamide (2.6 mg) (m/z): [M+H]$^+$ calcd for $C_{30}H_{40}N_2O_2$, 461.31; found 461.2.

Example 70 cyclohexanecarboxylic acid (R)-benzyl-{2-[3-endo-(3-hydroxy-phenyl)-8-aza-bicyclo[3.2.1]oct-8-yl]-1-methyl-ethyl}-amide (3.8 mg) (m/z): [M+H]$^+$ calcd for $C_{30}H_{40}N_2O_2$, 461.31; found 461.2.

Example 71

N-benzyl-2-ethyl-N—{(R)-2-[3-endo-(3-hydroxyphenyl)-8-azabicyclo[3.2.1]oct-8-yl]-1-methylethyl}butyramide (3.8 mg) (m/z): [M+H]$^+$ calcd for $C_{29}H_{40}N_2O_2$, 449.31; found 449.2.

Example 72

N-benzyl-N—{(R)-2-[3-endo-(3-hydroxyphenyl)-8-azabicyclo[3.2.1]oct-8-yl]-1-methylethyl}succinamic acid (5.7 mg) (m/z): [M+H]$^+$ calcd for $C_{27}H_{34}N_2O_4$, 451.25; found 451.2.

Example 73 cyclopentanecarboxylic acid (R)-benzyl-{2-[3-endo-(3-hydroxyphenyl)-8-aza-bicyclo[3.2.1]oct-8-yl]-1-methylethyl}amide (5.2 mg) (m/z): [M+H]$^+$ calcd for $C_{29}H_{38}N_2O_2$, 447.29; found 447.2.

Example 74

N-benzyl-N—{(R)-2-[3-endo-(3-hydroxyphenyl)-8-azabicyclo[3.2.1]oct-8-yl]-1-methylethyl}acetamide (4.6 mg) (m/z): [M+H]$^+$ calcd for $C_{25}H_{32}N_2O_2$, 393.25; found 393.2.

Example 75: Synthesis of N-cyclohexylmethyl-2-hydroxy-N-{2-[3-endo-(3-methanesulfonylamino-phenyl)-8-azabicyclo[3.2.1]oct-8-yl]-ethyl}acetamide a. Preparation of cyclohexylmethyl-{2-[3-endo-(3-methanesulfonylamino-phenyl)-8-azabicyclo[3.2.1]oct-8-yl]-ethyl}-carbamic Acid tert-butyl Ester To a solution of the TFA salt of N-[3-endo-(8-azabicyclo[3.2.1]oct-3-yl)-phenyl]-methanesulfonamide, the product of Preparation 23 (140 mg, 0.35 mmol) in DCM (2 mL) at room temperature was added a solution of cyclohexylmethyl-(2-oxo-ethyl)carbamic acid tert-butyl ester (116 mg, 0.455 mmol) followed by sodium triacetoxyborohydride (96 mg, 0.455 mmol). The resulting mixture was stirred at room temperature overnight and then diluted with DCM. The organic layer was washed with saturated sodium bicarbonate and brine, dried over sodium sulfate, filtered and concentrated to give the title intermediate as an oily residue, which was used directly in the next step. (m/z): [M+H]$^+$ calcd for $C_{28}H_{45}N_3O_4S$: 520.31; found: 520.4.

b. Preparation of N-(3-endo-{8-[2-(cyclohexylmethylamino)ethyl]-8-aza-bicyclo[3.2.1]oct-3-yl}-phenyl)-methanesulfonamide The oily product of the previous step was treated with DCM (1.5 mL) and TFA (1.5 mL) at room temperature for thirty minutes. Then it was concentrated, redissolved in a 1:1 mixture of acetic acid and water (6 mL), filtered and purified by reverse phase preparative HPLC to give the title intermediate as its bis TFA salt (38.9 mg). (m/z): [M+H]$^+$ calcd for $C_{23}H_{37}N_3O_2S$: 420.26; found: 420.4.

c. Synthesis of N-cyclohexylmethyl-2-hydroxy-N-{2-[3-endo-(3-methanesulfonylamino-phenyl)-8-azabicyclo[3.2.1]oct-8-yl]-ethyl}acetamide To a solution of the product of the previous step (39 mg, 0.06 mmol) in DCM (0.2 mL) at room temperature was added N,N-diisopropylethylamine (31 mg, 0.24 mmol) followed by acetoxyacetylchloride (12 mg, 0.09 mmol). Five minutes later, the reaction was concentrated, redissolved in ethanol (0.2 mL) and treated with lithium hydroxide monohydrate (15 mg, 0.36 mmol) in water (0.2 mL) at room temperature for thirty minutes. The reaction mixture was then reconcentrated and the resulting residue was dissolved in a 1:1 mixture of acetic acid and water (1.5 mL), filtered and purified by reverse phase preparative HPLC to give the title compound as its TFA salt (16.9 mg). (m/z): [M+H]$^+$ calcd for $C_{25}H_{39}N_3O_4S$: 478.27; found: 478.2.

Examples 76-204

In the following examples, the 8-azabicyclooctane phenol or 8-azabicyclooctane benzamide intermediate was prepared according to the process of Preparation 13 with the following exceptions: Preparation 1: Example 137; Preparation 12, steps a to c: Examples 106-108 and 112; Preparation 12: Examples 91, 101, 109-111, and 131.

Example 76: Synthesis of N-cyclohexylmethyl-2-hydroxy-N-{2-[3-endo-(3-hydroxyphenyl)-8-azabicyclo[3.2.1]oct-8-yl]ethyl}-2-(S)-phenylacetamide To a solution of 3-endo-{8-[2-(cyclohexylmethylamino)ethyl]-8-azabicyclo[3.2.1]oct-3-yl}phenol (30 mg, 0.087 mmol) in DMF (0.4 mL) was added HATU (39.6 mg, 0.10 mmol) and (S)-hydroxyphenyl acetic acid (15.2 mg, 0.1 mmol). The reaction mixture was concentrated by rotary evaporation and the residue was dissolved in 50% acetic acid in water (1.2 mL), filtered, purified by preparative HPLC to give the title product as a TFA salt (8.6 mg). (m/z): [M+H]$^+$ calcd for $C_{30}H_{40}N_2O_3$ 477.30; found, 477.4.

Examples 77-84

Using processes similar to that of Example 76, except replacing (S)-hydroxy-phenyl-acetic acid with the appropriate carboxylic acid, the TFA salts of the compounds of Examples 77-84 were prepared.

Example 77

(S)—N-cyclohexylmethyl-2-hydroxy-N-{2-[3-endo-(3-hydroxyphenyl)-8-aza-bicyclo[3.2.1]oct-8-yl]ethyl}-3-phenyl-propionamide (15.9 mg). (m/z): [M+H]$^+$ calcd for $C_{31}H_{42}N_2O_3$, 491.68; found 491.4.

Example 78

(R)—N-cyclohexylmethyl-2-hydroxy-N-{2-[3-endo-(3-hydroxyphenyl)-8-aza-bicyclo[3.2.1]oct-8-yl]ethyl}-4-phenyl-butyramide (17.8 mg). (m/z): [M+H]$^+$ calcd for $C_{32}H_{44}N_2O_3$, 505.34; found 505.4.

Example 79

1-hydroxy-cyclopropanecarboxylic acid cyclohexylmethyl-{2-[3-endo-(3-hydroxyphenyl)-8-azabicyclo[3.2.1]oct-8-yl]ethyl}amide (5.7 mg). (m/z): [M+H]$^+$ calcd for $C_{26}H_{38}N_2O_3$, 427.29; found 427.4.

Example 80

(S)-2-hydroxy-4-methyl-pentanoic acid cyclohexylmethyl-{2-[3-endo-(3-hydroxyphenyl)-8-azabicyclo[3.2.1]oct-8-yl]ethyl}amide (12.7 mg). (m/z): [M+H]$^+$ calcd for $C_{28}H_{44}N_2O_3$, 457.34; found 457.4.

Example 81

(S)—N-cyclohexylmethyl-2-dimethylamino-N-{2-[3-endo-(3-hydroxy-phenyl)-8-azabicyclo[3.2.1]oct-8-yl]ethyl}-3-phenylpropionamide (9.4 mg). (m/z): [M+H]$^+$ calcd for $C_{33}H_{47}N_3O_2$, 518.37; found 518.6.

Example 82

2-hydroxy-hexanoic acid cyclohexylmethyl-{2-[3-endo (3-hydroxy-phenyl)-8-azabicyclo[3.2.1]oct-8-yl]ethyl}amide (10.6 mg). (m/z): [M+H]$^+$ calcd for $C_{28}H_{44}N_2O_3$, 457.34; found 457.5.

Example 83

(R)-2-cyclohexyl-N-cyclohexylmethyl-2-hydroxy-N-{2-[3-endo-(3-hydroxy-phenyl)-8-azabicyclo[3.2.1]oct-8-yl]-ethyl}acetamide (9.8 mg). (m/z): [M+H]$^+$ calcd for $C_{30}H_{46}N_2O_3$, 483.35; found 483.2.

Example 84

(S)-2-cyclohexyl-N-cyclohexylmethyl-2-hydroxy-N-{2-[3-endo (3-hydroxy-phenyl)-8-azabicyclo[3.2.1]oct-8-yl]-ethyl}acetamide (14.5 mg). (m/z): [M+H]$^+$ calcd for $C_{30}H_{46}N_2O_3$, 483.35; found 483.4.

Examples 85-89

Using processes similar to that of Example 76, replacing the azabicyclooctane phenol with 3-endo-{8-[2-(cyclohexylmethylamino)ethyl]-8-azabicyclo[3.2.1]oct-3-yl}benzamide and utilizing the appropriate carboxylic acid, the TFA salts of the compounds of Examples 85-89 were prepared.

Example 85

3-endo-(8-{2-[cyclohexylmethyl-((S)-2-hydroxy-3-phenylpropionyl)-amino]ethyl}-8-azabicyclo[3.2.1]oct-3-yl)benzamide (15.2 mg). (m/z): [M+H]$^+$ calcd for $C_{32}H_{43}N_3O_3$ 518.33; found, 518.4.

Example 86

3-endo-(8-{2-[cyclohexylmethyl-((S)-2-hydroxy-4-methylpentanoyl)-amino]ethyl}-8-azabicyclo[3.2.1]oct-3-yl)-benzamide (19 mg). (m/z): [M+H]$^+$ calcd for $C_{29}H_{45}N_3O_3$ 484.35; found, 484.4.

Example 87

3 endo-(8-{2-[cyclohexylmethyl-(1-hydroxy-cyclopropanecarbonyl)-amino]ethyl}-8-azabicyclo[3.2.1]oct-3-yl)-benzamide (15.5 mg). (m/z): [M+H]$^+$ calcd for $C_{27}H_{39}N_3O_3$ 454.30; found, 454.4.

Example 88

3-endo-(8-{2-[cyclohexylmethyl-((S)-2-dimethylamino-3-phenyl-propionyl)amino]ethyl}-8-azabicyclo[3.2.1]oct-3-yl)benzamide (17.4 mg). (m/z): [M+H]$^+$ calcd for $C_{34}H_{48}N_4O_2$ 545.38; found, 545.4.

Example 89

3-endo-(8-{2-[cyclohexylmethyl-(3-hydroxy-2,2-dimethyl-propionyl)-amino]-ethyl}-8-azabicyclo[3.2.1]oct-3-yl)benzamide (5.3 mg). (m/z): [M+H]$^+$ calcd for $C_{28}H_{43}N_3O_3$ 470.33; found, 470.4.

Example 90: Synthesis of 3-endo-(8-{2-[cyclohexylmethyl-(4-dimethylamino-butyryl)amino]ethyl}-8-azabicyclo[3.2.1]oct-3-yl) benzamide To a vial charged with 4-dimethylamino-butyric acid HCl salt (19.7 mg, 0.15 mmol) was added DMF (0.3 mL) followed by HATU (57.0 mg, 0.15 mmol). After stirring for 1 h, the reaction mixture was treated with DIPEA (25.8 mg, 0.2 mmol) and 3-endo-{8-[2-(cyclohexylmethylamino)

ethyl]-8-azabicyclo[3.2.1]oct-3-yl}benzamide bis TFA salt (30.0 mg, 0.05 mmol). The resulting mixture was stirred at ambient temperature for 4 h and then heated at 65° C. overnight. After concentration, the resulting residue was dissolved in 50% acetic acid in water (1.5 mL) and purified by reverse phase preparative HPLC to give the title compound as a bis TFA salt (4.9 mg) (m/z): [M+H]$^+$ calcd for $C_{29}H_{46}N_4O_2$ 483.36; found 483.4.

Examples 91-92

Using processes similar to that of Example 90, except replacing 4-dimethylamino-butyric acid with the appropriate carboxylic acid, the compounds of Examples 91-92 were prepared.

Example 91

3-endo-(8-{2-[cyclohexylmethyl-(1-hydroxycyclopropanecarbonyl)-amino]ethyl}-8-aza-bicyclo[3.2.1]oct-3-yl)-benzamide TFA salt (18.8 mg). (m/z): [M+H]$^+$ calcd for $C_{27}H_{39}N_3O_3$ 454.30; found 454.2.

Example 92

3-endo-(8-{2-[cyclohexylmethyl-((S)-3-hydroxy-2-methylamino-propionyl)amino]ethyl}-8-aza-bicyclo[3.2.1]oct-3-yl)-benzamide bis TFA salt (24. mg). (m/z): [M+H]$^+$ calcd for $C_{27}H_{42}N_4O_3$ 471.33; found 471.4.

Example 93: Synthesis of 3-endo-(8-{2-[cyclohexylmethyl-(3-hydroxy-2-hydroxymethyl-2-methylpropionyl)amino]ethyl}-8-azabicyclo[3.2.1]oct-3-yl)-benzamide a. Preparation of 5-methyl-2-phenyl-1,3-dioxinane-5-carboxylic Acid Into a round bottom flask was added sequentially 3-hydroxy-2-hydroxymethyl-2-methyl-propionic acid (10.0 g, 74.5 mmol), acetone (75.0 mL), benzaldehyde dimethyl acetal (17.02 g, 111.0 mmol) and para-toluenesulfonic acid monohydrate (0.71 g, 3.7 mmol). The resulting mixture was stirred at ambient temperature for 4 h and then filtered. The filter cake was rinsed with cold acetone and dried under vacuum to give the title compound as a white solid. $^1$H NMR (CDCl$_3$, 300 MHz) δ (ppm): 7.46-7.48 (m, 2H), 7.34-7.36 (m, 3H), 5.49 (s, 1H), 4.65 (d, J=10.8 Hz, 2H), 3.70 (d, J=11.4 Hz, 2H), 1.11 (s, 3H).

b. Synthesis of 3-endo-(8-{2-[cyclohexylmethyl-(3-hydroxy-2-hydroxymethyl-2-methylpropionyl)amino]ethyl}-8-azabicyclo[3.2.1]oct-3-yl)-benzamide To a solution of the product of the previous step (55.7 mg, 0.25 mmol) in DMF (0.5 mL) at ambient temperature was added HATU (95.0 mg, 0.25 mmol). After stirring for 2 h, the reaction was treated with 3-endo-{8-[2-(cyclohexylmethylamino)ethyl]-8-azabicyclo[3.2.1]oct-3-yl}benzamide bis TFA salt (75.0 mg, 0.13 mmol) followed by DIPEA (64.9 mg, 0.50 mmol). The reaction was heated at 40° C. overnight. After concentration, the residue was treated with a mixture of acetic acid (2.1 mL) and water (0.7 mL) at 70° C. for 2 h and then reconcentrated. The resulting residue was dissolved in 50% acetic acid in water (1.5 mL) and purified by reverse phase preparative HPLC to give the TFA salt of the title compound (24.6 mg). (m/z): [M+H]$^+$ calcd for $C_{28}H_{43}N_3O_4$ 486.33; found 486.4.

Example 94: Synthesis of 3-endo-(8-{2-[cyclohexylmethyl-((S)-4-dimethylamino-2-hydroxy-butyryl)-amino]-ethyl}-8-aza-bicyclo[3.2.1]oct-3-yl)-benzamide a. Preparation of lithium (S)-4-tert-butoxycarbonylamino-2-hydroxybutyrate A solution of (S)-4-tert-butoxycarbonylamino-2-hydroxybutyric acid methyl ester (1.52 g, 6.52 mmol) in methanol (20.0 mL) was treated with lithium hydroxide monohydrate (273.8 mg, 6.52 mmol) and water (2.0 mL) for 30 min, concentrated, and dried under vacuum to give a white solid (1.26 g)

b. Preparation of 3-endo-(8-{2-[((S)-4-amino-2-hydroxybutyryl)cyclohexylmethyl-amino]ethyl}-8-azabicyclo[3.2.1]oct-3-yl)benzamide The product of the previous step (150.0 mg, 0.67 mmol) was dissolved in DMF (1.5 mL) at room temperature. To this solution was added sequentially 3-endo-{8-[2-(cyclohexylmethylamino)ethyl]-8-azabicyclo[3.2.1]oct-3-yl}benzamide bis TFA salt (200.0 mg, 0.335 mmol), HATU (253.3 mg, 0.67 mmol) and DIPEA (173.2 mg, 1.34 mmol). After stirring for 2 h, the reaction mixture was diluted with EtOAc (100.0 mL), washed sequentially with half saturated sodium bicarbonate (20.0 mL), saturated sodium bicarbonate (15.0 mL) and brine (15.0 mL), dried over sodium sulfate, filtered, and concentrated to give the intermediate [(S)-3-(2-[3-(3-endo-carbamoylphenyl)-8-azabicyclo[3.2.1]oct-8-yl]ethyl}-cyclohexylmethyl-carbamoyl)-3-hydroxypropyl]-carbamic acid tert-butyl ester as a yellowish oil. (m/z): [M+H]$^+$ calcd for $C_{32}H_{50}N_4O_5$ 571.4; found 571.6.

The intermediate was then treated with DCM (1.5 mL) and TFA (2.5 mL) at room temperature for thirty minutes. After concentration, the residue was dissolved in 25% acetic acid in water (8.0 mL), filtered and purified by reverse phase preparative HPLC to give the bis TFA salt of the title compound (194.4 mg). (m/z): [M+H]$^+$ calcd for $C_{27}H_{42}N_4O_3$ 471.3; found 471.6.

c. Synthesis of 3-endo-(8-{2-[((S)-4-dimethylamino-2-hydroxybutyryl)cyclohexylmethyl-amino]ethyl}-8-azabicyclo[3.2.1]oct-3-yl)benzamide To the solution of the product of the previous step (65.3 mg, 0.09 mmol) in methanol (0.3 mL) was added 37% aqueous formaldehyde solution (0.02 mL, 0.27 mmol) followed by sodium cyanoborohydride (14.0 mg, 0.27 mmol). The resulting mixture was stirred at room temperature for twenty minutes before it was concentrated. The residue was redissolved in 25% acetic acid in water (6.0 mL), filtered and purified by reverse phase preparative HPLC to give the bis TFA salt of the title compound (33.0 mg). $^1$H NMR (CD$_3$OD, 400M Hz) δ (ppm): 8.06 (s, 1H), 7.74-7.81 (m, 2H), 7.49-7.51 (m, 1H), 4.66-4.69 (m, 1H), 4.14-4.18 (m, 2H), 3.84-3.89 (m, 1H), 3.73-3.78 (m, 1H), 3.37-3.44 (obscure, 3H, partial overlap with solvent), 3.28-3.30 (obscure 2H, partial overlap with solvent), 3.20-3.22 (m, 2H), 2.96 (s, 6H), 2.61-2.70 (m, 4H), 2.09-2.18 (m, 4H), 1.74-1.88 (m, 8H), 1.25-1.36 (m, 3H), 1.04-1.12 (m, 2H). (m/z): [M+H]$^+$ calcd for $C_{29}H_{46}N_4O_3$ 499.36; found 499.6.

Example 95: Synthesis of 3-endo-(8-{2-[((S)-4-tert-butylamino-2-hydroxy-butyryl)-cyclohexylmethyl-amino]-ethyl}-8-aza-bicyclo[3.2.1]oct-3-yl)-benzamide To a solution of 3-endo-(8-{2-[((S)-4-amino-2-hydroxybutyryl)cyclohexylmethyl-amino]ethyl}-8-azabicyclo[3.2.1]oct-3-yl)benzamide bis TFA salt (29.0 mg, 0.04 mmol) in DMF (0.5 mL) was added DIPEA (20.7 mg, 0.16 mmol) and tert-butyl iodide (14.7 mg, 0.08 mmol). The resulting mixture was heated at 75° C. for 2 h. After concentration, the residue was dissolved in 25% acetic acid in water, and purified by reverse phase preparative HPLC to give the bis TFA salt of the title compound (4.5 mg). (m/z): [M+H]$^+$ calcd for $C_{31}H_{50}N_4O_3$ 526.38; found 526.6.

Example 96: Synthesis of 3-endo-(8-{2-[cyclohexylmethyl-((S)-4-diethylamino-2-hydroxybutyryl)amino]ethyl}-8-azabicyclo[3.2.1]oct-3-yl)-benzamide Using a process similar to that of Example 95 replacing tert-butyl iodide with ethyl iodide (3.0 eq), the bis TFA salt of the title compound was prepared (m/z): [M+H]$^+$ calcd for $C_{31}H_{50}N_4O_3$ 527.39; found 527.2.

Example 97: Synthesis of 3-endo-(8-{2-[cyclohexylmethyl-(3-dimethylamino-2-hydroxypropionyl)amino]ethyl}-8-azabicyclo[3.2.1]oct-3-yl)benzamide a. Preparation of [2-({2-[3-endo-(3-carbamoylphenyl)-8-azabicyclo[3.2.1]oct-8-yl]-ethyl}-cyclohexylmethyl-carbamoyl)-2-hydroxy-ethyl]-carbamic Acid 9H-fluoren-9-ylmethyl Ester Using a process similar to Example 94 (b) replacing lithium (S)-4-tert-butoxycarbonylamino-2-hydroxy-butyrate with 3-(9H-fluoren-9-ylmethoxycarbonylamino)-2-hydroxy-propionic acid (163.7 mg, 0.5 mmol, 2.0 eq), the title compound was obtained as a yellowish oil. (m/z): [M+H]$^+$ calcd for $C_{41}H_{50}N_4O_5$ 679.4; found 679.6.

b. Preparation of 3-endo-(8-{2-[(3-amino-2-hydroxypropionyl)-cyclohexylmethyl-amino]ethyl}-8-azabicyclo[3.2.1]oct-3-yl)-benzamide The product of the previous step was treated with DMF (2.0 mL) and piperidine (0.4 mL) at ambient temperature for 5 min and then concentrated. The residue was purified by reverse phase preparative HPLC to give the bis TFA salt of the title compound (93.7 mg). (m/z): [M+H]$^+$ calcd for $C_{26}H_{40}N_4O_3$ 457.3; found 457.4.

c. Synthesis of 3-endo-(8-{2-[cyclohexylmethyl-(3-dimethylamino-2-hydroxypropionyl)amino]ethyl}-8-azabicyclo[3.2.1]oct-3-yl)benzamide Following the process of Example 94 c, the bis TFA salt of the title compound was prepared (m/z): [M+H]$^+$ calcd for $C_{28}H_{44}N_4O_3$ 485.34; found 485.4.

Example 98: Synthesis of 3-endo-(8-{2-[cyclohexylmethyl-(4-hydroxy-butyryl)amino]ethyl}-8-azabicyclo[3.2.1]oct-3-yl)benzamide To a solution of γ-butyrolactone (170.0 mg, 1.98 mmol) in methanol (0.5 mL) was added water (0.2 mL) and lithium hydroxide monohydrate (83 mg, 2.0 mmol). The resulting mixture was stirred at room temperature overnight. After concentration, the residue was dried over the vacuum line to give the intermediate, lithium 4-hydroxybutyrate as a white solid. The intermediate (18.3 mg, 0.17 mmol) was added to a mixture of 3-endo-{8-[2-(cyclohexylmethylamino)ethyl]-8-azabicyclo[3.2.1]oct-3-yl}benzamide bis TFA salt (50 mg, 0.083 mmol) and DIPEA (58.3 µL, 0.33 mmol) in DMF (0.4 mL). Then HATU (63.1 mg, 0.17 mmol) was added and the resulting reaction mixture was stirred at room temperature overnight. After concentration, the residue was redissolved in 50% acetic acid in water (6 mL), filtered and purified by preparative HPLC. Desired fractions were combined and freeze dried to give a white solid. $^1$H NMR (CD$_3$OD, 400 MHz) δ (ppm): 8.05 (s, 1H), 7.79 (d, J=8.0 Hz, 1H), 7.74 (d, J=7.6 Hz, 1H), 7.51 (dd, J=7.6, 8.0 Hz, 1H), 4.13 (brs, 2H), 3.78 (t, J=5.6 Hz, 2H), 3.69 (t, J=6.0 Hz, 2H), 3.31-3.35 (obscure 3H, overlap with solvent), 3.17 (t, J=5.6 Hz, 2H), 2.43-2.53 (m, 6H), 2.01-2.05 (m, 2H), 1.61-1.84 (m, 10H), 1.12-1.26 (m, 3H), 0.89-0.98 (m, 2H). (m/z): [M+H]$^+$ calcd for $C_{27}H_{41}N_3O_3$ 456.31; found 456.4.

Examples 99-100

Using processes similar to that of Example 98, replacing γ-butyrolactone with the appropriate lactone, the compounds of Examples 99-100 were prepared.

Example 99

3-endo-(8-2-[cyclohexylmethyl-((S)-2,4-dihydroxybutyryl)amino]ethyl-8-azabicyclo[3.2.1]oct-3-yl)benzamide TFA salt, (m/z): [M+H]$^+$ calcd for $C_{27}H_{41}N_3O_4$ 472.31; found 472.4.

Example 100

3-endo-(8-2-[cyclohexylmethyl-((S)-3,4-dihydroxybutyrylamino]ethyl-8-azabicyclo[3.2.1]oct-3-yl)benzamide TFA salt (m/z): [M+H]$^+$ calcd for $C_{27}H_{41}N_3O_4$ 472.31; found 472.4.

Example 101: Synthesis of 3-endo-(8-{2-[cyclohexylmethyl-(2-dimethylamino-acetyl)amino]ethyl}-8-azabicyclo[3.2.1]oct-3-yl)-benzamide a. Preparation of 3-endo-{(8-[2-(cyclohexylmethyl-amino)ethyl]-8-azabicyclo[3.2.1]oct-3-yl}benzamide Following the procedure of Preparations 9 and 12, 3-endo-(8-aza-bicyclo[3.2.1]oct-3-yl)benzamide (1.18 g) was reacted with cyclohexylmethyl-(2-oxo-ethyl)-carbamic acid tert-butyl ester (1.57 g) to give {2-[3-endo-(3-carbamoylphenyl)-8-azabicyclo[3.2.1]oct-8-yl]-ethyl}cyclohexylmethyl-carbamic acid tert-butyl ester, which was further treated with DCM and TFA. The resulting crude product was dissolved in 50% acetic acid in water (15.0 mL) and purified by reverse phase preparative HPLC. Desired fractions were combined and freeze dried to give the bis TFA salt of the title compound (1.65 g). $^1$H NMR (CD$_3$OD, 300 MHz) δ (ppm): 8.03 (s, 1H), 7.71-7.77 (m, 2H), 7.44-7.50 (m, 1H), 4.11 (brs, 2H), 3.52 (t, J=6.0 Hz, 2H), 3.33-3.40 (obscure 3H, overlap with solvent), 2.96 (d, J=6.6 Hz, 2H), 2.67-2.67 (m, 4H), 2.05-2.12 (m, 2H), 1.70-1.84 (m, 8H), 1.20-1.39 (m, 3H), 1.03-1.10 (m, 2H).

(m/z): [M+H]⁺ calcd for $C_{23}H_{35}N_3O$ 370.28; found 370.2.

b. Synthesis of 3-endo-(8-{2-[cyclohexylmethyl-(2-dimethylamino-acetyl)amino]ethyl}-8-azabicyclo[3.2.1]oct-3-yl)-benzamide To a solution of the product of the previous step (33.0 mg, 0.055 mmol) in DCM (0.3 mL) at ambient temperature was added DIPEA (28.4 mg, 0.22 mmol) followed by dimethylamino-acetyl chloride HCl salt (12.6 mg, 0.08 mmol). The reaction mixture was stirred for 10 min and then concentrated. The resulting residue was dissolved in 50% acetic acid in water (1.5 mL), filtered and purified by reverse phase preparative HPLC to give the bis TFA salt of the title compound. (16.1 mg). (m/z): [M+H]⁺ calcd for $C_{27}H_{42}N_4O_2$ 455.33; found 455.2.

Examples 102-103

Using processes similar to that of Example 101, replacing dimethylamino-acetyl chloride with the appropriate chloride, the compounds of Examples 102-103 were prepared.

Example 102

3-endo-(8-(2-((cyclohexylmethyl)(N,N-dimethylsulfamoyl)amino)ethyl)-8-azabicyclo[3.2.1]oct-3-yl)benzamide TFA salt (21.2 mg). (m/z): [M+H]⁺ calcd for $C_{25}H_{40}N_4O_3S$ 477.28; found 477.2.

Example 103

3-endo-(8-{2-[cyclohexylmethyl-(2-methoxyacetyl)amino]ethyl}-8-aza-bicyclo[3.2.1]oct-3-yl)-benzamide TFA salt (m/z): [M+H]⁺ calcd for $C_{26}H_{39}N_3O_3$ 442.30; found 442.4.

Example 104: Synthesis of 3-endo-(8-{2-[((S)-2,3-dihydroxypropionyl)-(3-hydroxy-adamantan-1-ylmethyl)amino]ethyl}-8-aza-bicyclo[3.2.1]oct-3-yl)benzamide a. Preparation of 3-aminomethyl-adamantan-1-ol

To a vigorously stirred mixture of concentrated sulfuric acid (22.7 mL) and 65% nitric acid (2.3 mL) at 0° C. was added C-adamantan-1-yl-methylamine (2.0 g, 12.12 mmol) dropwise. The reaction mixture was stirred for 2 h at 0° C., warmed to room temperature and stirred at that temperature for 24 h, cooled to 0° C. and slowly quenched with ice (10.8 g). The mixture was allowed to warm to ambient as ice melts overnight, cooled to 0° C. again and treated with sodium hydroxide (50 g) in small portions. The resulting brownish paste was filtered, and the filter cake was rinsed with DCM (200 mL). After separation, the organic layer was washed with brine (2×20 mL), dried over sodium sulfate, filtered and concentrated to give a white solid (1.09 g). (m/z): [M+H]⁺ calcd for $C_{11}H_{19}N$ 182.2; found 182.2.

b. Preparation of 3-endo-(8-{2-[(3-hydroxy-adamantan-1-ylmethyl)amino]ethyl}-8-azabicyclo[3.2.1]oct-3-yl)benzamide To a solution of 3-endo-[8-(2-oxoethyl)-8-azabicyclo[3.2.1]oct-3-yl)-benzamide HCl salt (108.6 mg, 0.60 mmol) in DCM (5.0 mL) was added sodium triacetoxyborohydride (137.8 mg, 0.65 mmol) followed by the product from the previous step (190.0 mg, 0.50 mmol). The resulting mixture was stirred at ambient for 2 h before it was concentrated. The residue was dissolved in 25% acetic acid in water (6.0 mL), filtered and purified by reverse phase preparative HPLC to give the bis TFA salt of the title compound (91.0 mg). (m/z): [M+H]⁺ calcd for $C_{27}H_{39}N_3O_2$ 438.3; found 438.4.

c. Synthesis of 3-endo-(8-{2-[((S)-2,3-dihydroxypropionyl)-(3-hydroxy-adamantan-1-ylmethyl)amino]ethyl}-8-aza-bicyclo[3.2.1]oct-3-yl) benzamide To a suspension of lithium (4S)-2,2-dimethyl-1,3-dioxolane-4-carboxylate (28.0 mg, 0.17 mmol) in DMF (0.5 mL) was added HATU (62.5 mg, 0.164 mmol) at room temperature. The mixture was sonicated to aid dissolving. After 1 h, DIPEA (87.9 mg, 0.68 mmol) was added followed by the product from previous step (60.0 mg, 0.085 mmol). The resulting mixture was stirred for 2 h and then concentrated. The residue was treated with a mixture of acetic acid (2.1 mL) and water (0.7 mL) at 70° C. for 1 h. After concentration, the oily residue was dissolved in 50% acetic acid in water (3.0 mL) and purified by reverse phase preparative HPLC to give the TFA salt of the title compound (6.2 mg). (m/z): [M+H]⁺ calcd for $C_{30}H_{43}N_3O_5$ 526.32; found 526.4.

Example 105 Synthesis of 3-endo-(8-{2-[(2-hydroxyacetyl)-(3-hydroxy-adamantan-1-ylmethyl)amino]ethyl}-8-azabicyclo[3.2.1]oct-3-yl)benzamide Salt To a solution of 3-endo-(8-{2-[(3-hydroxy-adamantan-1-ylmethyl)amino]ethyl}-8-azabicyclo[3.2.1]oct-3-yl)benzamide bis TFA salt (132.2 mg, 0.20 mmol) in DCM (1.0 mL) was added DIPEA (0.14 mL, 0.79 mmol) followed by acetoxyacetal chloride (54.6 mg, 0.40 mmol) at room temperature. The reaction mixture was stirred for 5 min, and then concentrated. The resulting residue was redissolved in methanol (2.0 mL) and treated with lithium hydroxide monohydrate (50.0 mg, 1.2 mmol) for 30 min and reconcentrated. The residue was dissolved in 50% acetic acid in water (1.5 mL), filtered and purified by reverse phase preparative HPLC to give the TFA salt of the title compound (23.4 mg). ¹H NMR (CD₃OD, 400 MHz) δ (ppm): 8.16 (s, 1H), 7.88 (d, J=7.6 Hz, 1H), 7.85 (d, J=8.0 Hz, 1H), 7.60 (dd, J=7.6, 8.0 Hz, 1H), 4.46 & 4.44 (two sets of s, 2H total), 4.25 & 4.20 (two sets of brs, 2H total), 3.92 (t, J=5.6 Hz, 2H), 3.44-3.46 (m, 1H), 3.31 (t, J=5.6 Hz, 2H), 3.25 (s, 2H), 2.75-2.82 (m, 4H), 2.36 (brs, 2H), 2.24-2.30 (m, 2H), 1.92-1.98 (m, 2H), 1.62-1.85 (m, 12H). (m/z): [M+H]⁺ calcd for $C_{29}H_{41}N_3O_4$ 496.31; found 496.4.

Examples 106-112

Using processes similar to that of Examples 104b and 105, using the appropriate oxoethyl-8-azabicyclooctane and appropriate chloride, the compounds of Examples 106-112 were prepared.

Example 106

N-adamantan-1-ylmethyl-2-hydroxy-N-{2-[3-endo-(3-hydroxyphenyl)-8-azabicyclo[3.2.1]oct-8-yl]-ethyl}acetamide TFA salt (m/z): [M+H]⁺ calcd for $C_{28}H_{40}N_2O_3$ 453.31; found 453.2.

Example 107

N-adamantan-1-ylmethyl-N-{2-[3-endo-(3-hydroxyphenyl)-8-aza-bicyclo[3.2.1]oct-8-yl]-ethyl}acetamide TFA salt (m/z): [M+H]+ calcd for $C_{28}H_{40}N_2O_2$ 437.31; found 437.2.

Example 108

N-adamantan-1-ylmethyl-N-{2-[3-endo-3-hydroxyphenyl)-8-aza-bicyclo[3.2.1]oct-8-yl]-ethyl}succinamic acid TFA salt (m/z): [M+H]+ calcd for $C_{30}H_{42}N_2O_4$ 495.31; found 495.2.

Example 109

3-endo-(8-{2-[adamantan-1-ylmethyl-(2-hydroxyacetyl) amino]ethyl}-8-azabicyclo[3.2.1]oct-3-yl)-benzamide TFA salt (m/z): [M+H]+ calcd for $C_{29}H_{41}N_3O_3$ 480.31; found 480.2.

Example 110

N-adamantan-1-ylmethyl-N-{2-[3-endo-(3-carbamoylphenyl)-8-aza-bicyclo[3.2.1]oct-8-yl]-ethyl}succinamic acid TFA salt (m/z): [M+H]+ calcd for $C_{31}H_{43}N_3O_4$ 522.33; found 522.2.

Example 111

3-endo-{8-[2-(acetyl-adamantan-1-ylmethyl-amino) ethyl]-8-azabicyclo[3.2.1]oct-3-yl}benzamide TFA salt (m/z): [M+H]+ calcd for $C_{29}H_{41}N_3O_2$ 464.32; found 464.2.

Example 112

N-(2,6-difluorobenzyl)-N-{2-[3-endo-(3-hydroxyphenyl)-8-aza-bicyclo[3.2.1]oct-8-yl]-ethyl}succinamic acid TFA salt (m/z): [M+H]+ calcd for $C_{26}H_{30}F_2N_2O_4$ 473.22; found 473.2.

Example 113: Synthesis of N-(2,6-Difluoro-benzyl)-N-{2-[3-(3-hydroxy-phenyl)-8-aza-bicyclo[3.2.1]oct-8-yl]-ethyl}-succinamic acid 3-endo-(8-{2-[(2,6-difluorobenzyl)-(2-hydroxy-acetyl)amino]ethyl}-8-azabicyclo[3.2.1]oct-3-yl)benzamide a. Preparation of 2-(2,6-difluorobenzylamino)ethanol

A mixture of 2,6-difluorobenzyl bromide (3.7 g, 17.8 mmol) and ethanolamine (6.46 mL, 107 mmol) in ethanol (18 mL) was heated at 75° C. for 16 h. The reaction mixture was concentrated and the resulting residue was diluted with dichloromethane (50 mL). The organic layer was partitioned with water (75 mL) and the aqueous layer extracted with dichloromethane (50 mL). Combined organic layers were dried over magnesium sulfate, filtered, and concentrated to give the title compound as a yellow solid (3.25 g). (m/z): [M+H]+ calcd for $C_9H_{11}F_2NO$, 188.08; found, 188.1. $^1H$ NMR ($d_6$-DMSO, 300 MHz) δ (ppm): 7.37-7.34 (m, 1H), 7.10-7.05 (m, 2H), 4.47 (t, J=5.4 Hz, 1H), 3.75 (s, 2H), 3.42 (q, J=5.5 Hz, 2H), 2.25 (t, J=5.7 Hz, 2H), 1.82 (br s, 1H).

b. Preparation of (2,6-difluorobenzyl)-(2-hydroxyethyl)-carbamic Acid tert-butyl Ester To the solution of the product of the previous step (3.25 g, 17.4 mmol) in dichloromethane (20 mL) at 0° C. was added a solution of di-tert-butyl dicarbonate (3.40 g, 15.6 mmol) via a syringe dropwise over 5 min. The resulting mixture was slowly warmed to room temperature and stirred overnight under an atmosphere of nitrogen. The crude reaction mixture was diluted with DCM (50 mL) and washed successively with 1 N aq HCl (2×50 mL), saturated NaHCO$_3$ (3×50 mL) and brine (50 mL). The organic layer was dried with magnesium sulfate, filtered, and concentrated to yield the title compound (4.46 g). (m/z): [M+H]+ calcd for $C_{14}H_{19}F_2NO_3$, 288.13; found, 288.2.

c. Preparation of (2,6-difluoro-benzyl)-(2-oxo-ethyl)-carbamic Acid tert-butyl Ester To the solution of the product of the previous step (4.46 g, 15.5 mmol) in DCM (50 mL) at 0° C. was added sequentially dimethyl sulfoxide (1.79 g, 23 mmol), DIPEA (5.01 g, 38.9 mmol) and sulfur trioxide pyridium complex (6.20 g, 38.9 mmol). After 30 min, the reaction was washed successively with 1N aq HCl (3×100 mL), saturated NaHCO$_3$ (100 mL) and brine (100 mL), filtered, and eluted with DCM. After concentration, the title compound was obtained as a yellow oil (2.31 g). $^1H$ NMR ($d_6$-DMSO, 300 MHz) δ (ppm): 9.42 (s, 1H), 7.40 (m, 1H), 7.09 (m, 2H), 4.49 (s, 2H), 4.00 (d, J=24.6, 2H), 1.31 (s, 9H).

d. Preparation of {2-[3-endo-(3-carbamoylphenyl)-8-azabicyclo[3.2.1]oct-3-yl]-ethyl}-(2,6-difluorobenzyl)-carbamic Acid tert-butyl Ester To a solution of 3-endo-(8-azabicyclo[3.2.1]oct-3-yl)benzamide (120 mg, 0.56 mmol) in DCM (2 mL) at 0° C. was added a solution of the product of the previous step (193 mg, 0.68 mmol) in DCM (1 mL) followed by sodium triacetoxyborohydride (144 mg, 0.68 mmol). The resulting mixture was warmed to room temperature and allowed to react for 1 h. The reaction mixture was diluted with DCM, washed with saturated sodium bicarbonate and brine, dried over sodium sulfate, filtered, and concentrated to give a yellowish oil and used in next step without further purification. (m/z): [M+H]+ calcd for $C_{28}H_{35}F_2N_3O_3$, 500.26; found, 500.1.

e. Preparation of: 3-endo-{8-[2-(2,6-difluorobenzylamino) ethyl]-8-aza-bicyclo[3.2.1]oct-3-yl}-benzamide The oily residue from the previous step was dissolved in DCM (2 mL) and treated with TFA (2 mL) at room temperature for 2 h. The mixture was concentrated and coevaporated with ethyl acetate three times, diluted with DCM and basified to pH=8.0 with saturated sodium bicarbonate. The layers were separated and the aqueous layer was extracted with DCM. The combined organic layer was washed with brine, dried over sodium sulfate, filtered, and concentrated to yield a dark oil (200 mg). (m/z): [M+H]+ calcd for $C_{23}H_{27}F_2N_3O$, 400.21; found, 400.4.

f. Synthesis of 3-endo-(8-{2-[(2,6-difluorobenzyl)-(2-hydroxyacetyl)amino]ethyl}-8-azabicyclo[3.2.1]oct-3-yl)benzamide To a solution of the mono-TFA salt of 3-endo-{8-[2-(2, 6-difluorobenzylamino)-ethyl]-8-azabicyclo[3.2.1]oct-3-yl}benzamide (132 mg, 0.26 mmol) in DCM (1 mL) at 0° C. was added DIPEA (132 mg, 1.0 mmol). The reaction mixture was then treated with acetoxy acetyl chloride (46 mg, 0.34 mmol) for 30 min. The reaction mixture was concentrated and the crude oil was dissolved in ethanol (0.5 mL) and treated with lithium hydroxide monohydrate (66 mg, 1.65 mmol) in water (0.2 mL). The solvent was concentrated and the residue was dissolved in 50% acetic acid in water (5 mL), filtered, and purified by preparative HPLC to give the TFA salt of the title compound (30.8 mg). (m/z): [M+H]$^+$ calcd for $C_{25}H_{29}F_2N_3O_3$, 458.22; found, 458.2. $^1$H NMR (CD$_3$OD, 400 MHz) δ (ppm): 8.025 (s, 1H), 7.75 (d, J=7.6 Hz, 1H), 7.72 (d, J=8.4 Hz, 1H), 7.49-7.45 (m, 2H), 7.103 (t, J=8.8 Hz, 2H), 4.67 (s, 2H), 4.52 (s, 2H), 4.10 (br s, 2H), 3.71 (t, J=6.0 Hz, 2H), 3.4-3.3 (obscure, 1H, overlap with solvent), 3.08 (t, J=5.6 Hz, 2H), 2.63-2.61 (m, 4H), 2.06-2.03 (m, 2H), 1.83-1.79 (m, 2H).

Examples 114-118

Using processes similar to that of Example 113 (f), utilizing the appropriate chloride, the compounds of Examples 114-118 were prepared.

Example 114

3-endo-(8-(2-((2,6-difluorobenzyl)(N,N-dimethylsulfamoyl)amino)ethyl)-8-azabicyclo[3.2.1]oct-3-yl)benzamide TFA salt (m/z): [M+H]$^+$ calcd for $C_{25}H_{32}F_2N_4O_3S$, 507.22; found, 507.4.

Example 115

3-endo-(8-{2-[(2,6-difluorobenzyl)-(2-hydroxy-2-methylpropionyl)-amino]ethyl}-8-azabicyclo[3.2.1]oct-3-yl)-benzamide TFA salt (m/z): [M+H]$^+$ calcd for $C_{27}H_{33}F_2N_3O_3$, 486.25; found, 486.4.

Example 116

3-endo-(8-{2-[(2,6-difluorobenzyl)-(2-methoxyacetyl)-amino]ethyl}-8-aza-bicyclo[3.2.1]oct-3-yl)benzamide TFA salt (m/z): [M+H]$^+$ calcd for $C_{26}H_{31}F_2N_3O_3$, 472.23; found, 472.4. $^1$H NMR (CD$_3$OD, 400 MHz) δ (ppm): 8.023 (s, 1H), 7.75 (d, J=8.0 Hz, 1H), 7.72 (d, J=8.8 Hz, 1H) 7.49-7.45 (m, 2H), 7.103 (t, J=8.4 Hz, 2H), 4.72 (s, 2H), 4.45 (s, 2H), 4.08 (br s, 2H), 3.71 (t, J=6.0 Hz, 2H), 3.48 (s, 3H), 3.4-3.3 (obscure, 1H, overlap with solvent), 3.05 (t, J=5.6 Hz, 2H), 2.62-2.59 (m, 4H), 2.05-2.02 (m, 2H), 1.81-1.79 (m, 2H).

Example 117

3-endo-(8-{2-[(2,6-difluorobenzyl)-(2,2-dimethylpropionyl)amino]-ethyl}-8-aza-bicyclo[3.2.1]oct-3-yl)benzamide TFA salt (m/z): [M+H]$^+$ calcd for $C_{28}H_{35}F_2N_3O_2$, 484.27; found, 484.4.

Example 118

3-endo-(8-{2-[(2,6-difluorobenzyl)-methanesulfonylamino]-ethyl}-8-aza-bicyclo[3.2.1]oct-3-yl)-benzamide TFA salt (m/z): [M+H]$^+$ calcd for $C_{24}H_{29}F_2N_3O_2S$, 478.19; found, 478.2; $^1$H NMR (CD$_3$OD, 400 MHz) δ (ppm): 8.00 (s, 1H), 7.76 (d, J=7.6 Hz, 1H), 7.70 (d, J=8.4 Hz, 1H) 7.49-7.45 (m, 2H), 7.10 (t, J=8.4 Hz, 2H), 4.67 (s, 2H), 4.10 (br s, 2H), 3.65 (t, J=6.0 Hz, 2H), 3.4-3.3 (obscure, 1H, overlap with solvent), 2.99 (s, 3H), 2.62-2.59 (m, 4H), 2.04-2.02 (m, 2H), 1.83-1.81 (m, 2H).

Example 119: Synthesis of 3-endo-(8-{2-[(2,6-difluorobenzyl)-(2-methanesulfonylacetyl)amino]ethyl}-8-aza-bicyclo[3.2.1]oct-3-yl)benzamide To a solution of methanesulfonyl-acetic acid (80.8 mg, 0.58 mmol) in DMF (1.0 mL) was added HATU (220 mg, 0.58 mmol). After stirring for 1 h at room temperature, the reaction mixture was treated with the mono-TFA salt of 3-endo-{8-[2-(2,6-difluorobenzylamino)ethyl]-8-azabicyclo [3.2.1]oct-3-yl}benzamide (150 mg, 0.29 mmol) and DIPEA (74.8 mg, 0.58 mmol) at 45° C. for 16 h. The solvent was concentrated and the residue dissolved in 50% acetic acid in water (5 mL), filtered, and purified by preparative HPLC to give the TFA salt of the title compound (52.4 mg). (m/z): [M+H]$^+$ calcd for $C_{26}H_{31}F_2N_3O_4S$, 520.20; found, 520.4; $^1$H NMR (CD$_3$OD, 400 MHz) δ (ppm): 8.01 (s, 1H), 7.76 (d, J=7.6 Hz, 1H), 7.70 (d, J=8.0 Hz, 1H) 7.51-7.45 (m, 2H), 7.11 (t, J=8.4 Hz, 2H), 4.89 (s, 2H), 4.68 (s, 2H), 4.10 (br s, 2H), 3.78 (t, J=6.0 Hz, 2H), 3.4-3.3 (obscure, 1H, overlap with solvent), 3.26 (s, 3H), 3.15 (t, J=5.6 Hz, 2H), 2.63-2.60 (m, 4H), 2.09-2.06 (m, 2H), 1.83-1.80 (m, 2H).

Examples 120-129

Using processes similar to that of Example 119, utilizing the appropriate carboxylic acid or carboxylate, the compounds of Examples 120-129 were prepared.

Example 120

3-endo-(8-{2-[(2,6-difluorobenzyl)-((S)-2-hydroxy-3-phenylpropionyl)-amino]ethyl}-8-aza-bicyclo[3.2.1]oct-3-yl)benzamide TFA salt (m/z): [M+H]$^+$ calcd for $C_{32}H_{35}F_2N_3O_3$, 548.26; found, 548.4.

Example 121

3-endo-(8-{2-[(2,6-difluorobenzyl)-((S)-2-hydroxy-4-methylpentanoyl)-amino]ethyl}-8-aza-bicyclo[3.2.1]oct-3-yl)benzamide TFA salt (m/z): [M+H]$^+$ calcd for $C_{29}H_{37}F_2N_3O_3$ 514.28; found, 514.4.

Example 122

3-endo-(8-{2-[(2,6-difluoro-benzyl)-((R)-2,3-dihydroxypropionyl)-amino]ethyl}-8-azabicyclo[3.2.1]oct-3-yl)benzamide TFA salt (m/z): [M+H]$^+$ calcd for $C_{26}H_{31}F_2N_3O_4$, 488.23; found, 488.4.

Example 123

3-endo-(8-{2-[(2,6-difluorobenzyl)-((S)-2,3-dihydroxypropionyl)-amino]ethyl}-8-aza-bicyclo[3.2.1]oct-3-yl)benzamide TFA salt (m/z): [M+H]$^+$ calcd for $C_{26}H_{31}F_2N_3O_4$, 488.23; found, 488.2.

Example 124

3-endo-(8-{2-[(2,6-difluorobenzyl)-((S)-2-hydroxypropionyl)amino]-ethyl}-8-aza-bicyclo[3.2.1]oct-3-yl)benzamide TFA salt (m/z): [M+H]$^+$ calcd for $C_{26}H_{31}F_2N_3O_3$, 472.23; found, 472.4; $^1$H NMR (CD$_3$OD, 400 MHz) δ (ppm): 8.02 (s, 1H), 7.77-7.70 (m, 2H), 7.50-7.45 (m, 2H), 7.10 (t, J=8.0 Hz, 2H), 4.91 (s, 2H), 4.08-4.00 (m, 2H), 3.87-3.83 (m, 1H), 3.61-3.60 (m, 1H), 3.01 (t, J=6.0 Hz, 2H), 2.63-2.61 (m, 4H), 2.04-1.99 (m, 2H), 1.81-1.79 (m, 2H), 1.40 (d, J=6.4 Hz, 3H).

Example 125

3-endo-(8-{2-[(2,6-difluorobenzyl)-(3-hydroxy-2,2-dimethylpropionyl)-amino]ethyl}-8-azabicyclo[3.2.1]oct-3-yl)benzamide TFA salt (m/z): [M+H]$^+$ calcd for $C_{28}H_{35}F_2N_3O_3$, 500.26; found, 500.4; $^1$H NMR (CD$_3$OD, 400 MHz) δ (ppm): 8.01 (s, 1H), 7.76 (d, J=7.6 Hz, 1H), 7.70 (d, J=7.6 Hz, 1H), 7.49 (m, 2H), 7.09 (t, J=8.4 Hz, 2H), 5.02 (s, 2H), 4.04 (br s, 2H), 3.78 (s, 2H), 3.66 (t, J=6.4 Hz, 2H), 3.4-3.3 (obscure, 1H, overlap with solvent), 2.98 (t, J=6.0 Hz, 2H), 2.66-2.54 (m, 4H), 2.02-1.99 (m, 2H), 1.80-1.76 (m, 2H), 1.41 (s, 6H). Reagent lithium-3-hydroxy-2,2-dimethyl-propionic carboxylate prepared by treating 3-hydroxy-2,2-dimethyl-propionic acid methyl ester (5.0 g, 37.7 mmol) in methanol (45 mL) with lithium hydroxide monohydrate (1.6 g, 37.8 mmol).

Example 126

3-endo-(8-{2-[(2-cyanoacetyl)-(2,6-difluorobenzyl)amino]ethyl}-8-aza-bicyclo[3.2.1]oct-3-yl)-benzamide TFA salt (m/z): [M+H]$^+$ calcd for $C_{26}H_{28}F_2N_4O_2$ 467.22; found, 467.2; $^1$H NMR (CD$_3$OD, 400 MHz) δ (ppm): 8.02 (s, 1H), 7.76 (d, J=8.0 Hz, 1H), 7.72 (d, J=7.6 Hz, 1H), 7.50-7.48 (m, 2H), 7.12 (t, J=8.4 Hz, 2H), 4.72 (s, 2H), 4.11 (br s, 2H), 3.70 (t, J=6.4 Hz, 2H), 3.4-3.3 (obscure, 1H, overlap with solvent), 3.09 (t, J=6 Hz, 2H), 2.65-2.59 (m, 4H), 2.06-2.05 (m, 2H), 1.82-1.79 (m, 2H).

Example 127

3-endo-(8-{2-[(2,6-difluorobenzyl)-(1-hydroxycyclopropanecarbonyl)-amino]ethyl}-8-azabicyclo[3.2.1]oct-3-yl)benzamide TFA salt (m/z) [M+H]$^+$ calcd for $C_{27}H_{31}F_2N_3O_3$ 484.23; found, 484.4.

Example 128

3-endo-(8-{2-[(2-tert-butoxyacetyl)-(2,6-difluorobenzyl)amino]ethyl}-8-azabicyclo[3.2.1]oct-3-yl)benzamide TFA salt (m/z): [M+H]$^+$ calcd for $C_{29}H_{37}F_2N_3O_3$ 514.28; found, 514.4.

Example 129

3-endo-(8-{2-[(2,6-difluorobenzyl)-(trans-4-hydroxy-cyclohexanecarbonyl)amino]ethyl}-8-azabicyclo[3.2.1]oct-3-yl)benzamide TFA salt (m/z): [M+H]$^+$ calcd for $C_{30}H_{37}F_2N_3O_3$ 526.28; found, 526.4.

Example 130 Synthesis of 3-endo-(8-{3-[cyclohexylmethyl-(2-hydroxy-acetyl)amino]propyl}-8-azabicyclo[3.2.1]oct-3-yl)benzamide a. Preparation of 3-endo-[8-(3-hydroxypropyl)-8-azabicyclo[3.2.1]oct-3-yl]-benzamide A mixture of 3-(8-azabicyclo[3.2.1]oct-3-yl)benzamide (326.7 mg, 1.42 mmol) and 3-bromo-1-propanol (217.1 mg, 1.56 mmol) in EtOH (1.0 mL) was heated at 70° C. for one hour. After concentration, the residue was coevaporated with DCM three times and dried under vacuum to give the title compound as a light yellowish foam. (m/z): [M+H]$^+$ calcd for $C_{17}H_{24}N_2O_2$ 289.2; found 289.0.

b. Preparation of Methanesulfonic Acid 3-endo-[3-(3-carbamoyl-phenyl)-8-aza-bicyclo[3.2.1]oct-8-yl] propyl Ester The product of the previous step was dissolved in DCM (7.0 mL). To the resulting solution was added DIPEA (367.1 mg, 2.84 mmol) followed by methanesulfonyl chloride (275.2 mg, 2.41 mmol) and DMAP (24.2 mg, 0.20 mmol). The reaction was stirred at room temperature for 3 h and then stored at 4° C. overnight. The reaction mixture was concentrated and the oily residue was dried under vacuum line to give an orange color oil which was used directly in the next step.

c. 3-endo-{8-[3-(cyclohexylmethylamino)propyl]-8-azabicyclo[3.2.1]oct-3-yl}-benzamide Half of the crude product of the previous step was dissolved in DMF (0.8 mL) and treated with DIPEA (183.2 mg, 1.42 mmol) and cyclohexylmethyl amine (200.6 mg, 1.77 mmol) at 75° C. for 1 h. After concentration, the residue was dissolved in 50% acetic acid in water (8.0 mL), filtered and purified by reverse phase preparative HPLC to give the title compound as its bis TFA salt (103.9 mg). (m/z): [M+H]$^+$ calcd for $C_{24}H_{37}N_3O$ 384.3; found 384.4.

d. Synthesis of 3-endo-(8-{3-[cyclohexylmethyl-(2-hydroxy-acetyl)amino]propyl}-8-azabicyclo[3.2.1]oct-3-yl)benzamide To a solution of the product of the previous step (100.0 mg, 0.164 mmol) in DCM (0.6 mL) was added DIPEA (84.4 mg, 0.65 mmol) followed by acetoxyacetyl chloride (24.5 mg, 0.18 mmol). Five min later, the reaction was concentrated. The residue was redissolved in methanol (0.6 mL) and treated with lithium hydroxide monohydrate (41.32 mg, 0.984 mmol) in water (0.6 mL) for thirty minutes. The reaction mixture was concentrated and the resulting residue was dissolved in a mixture of 50% acetic acid in water (6.0 mL) and water (2.0 mL), filtered and purified by reverse phase preparative HPLC to give the title compound as its TFA salt (22.1 mg). (m/z): [M+H]$^+$ calcd for $C_{26}H_{39}N_3O_3$ 442.30; found 442.6; $^1$H NMR (CD$_3$OD, 400M Hz) δ (ppm): 8.08 (s, 1H), 7.76-7.80 (m, 2H), 7.48-7.55 (m, 6H), 4.28 (s, 2H), 4.08 (brs, 2H), 3.36-3.38 (obscure 1H, partially overlap with solvent), 3.20 (t, J=7.2 Hz, 2H), 3.12 (t, J=8.4 Hz, 2H), 2.62-2.78 (m, 4H), 2.21-2.29 (m, 2H), 2.09-2.12 (m, 2H), 1.78-1.84 (m, 2H).

Example 131 Synthesis of 3-endo-{8-[3-(acetylcyclohexylmethylamino)-propyl]-8-azabicyclo[3.2.1]oct-3-yl}benzamide To a solution of 3-endo-{8-[3-(cyclohexylmethylamino)-propyl]-8-aza-bicyclo[3.2.1]oct-3-yl}benzamide bis TFA salt (30.0 mg, 0.05 mmol) in DCM (0.2 mL) was added DIPEA (25.8 mg, 0.20 mmol) followed by acetic anhydride (7.65 mg, 0.075 mmol). Thirty minutes later, the reaction was concentrated. The residue was dissolved in ethanol (0.4 mL) and treated with lithium hydroxide monohydrate (12.6 mg, 0.30 mmol) in water (0.4 mL) for thirty minutes. The reaction mixture was concentrated and the resulting residue was dissolved in 50% acetic acid in water (1.5 mL), filtered and purified by reverse phase preparative HPLC to give the title compound as its TFA salt (26.7 mg). (m/z): [M+H]$^+$ calcd for $C_{26}H_{39}N_3O_2$ 426.30; found 426.2.

Example 132 Synthesis of 3-endo-(8-{3-[cyclohexylmethyl-(2-methanesulfonyl-acetyl)amino]propyl}-8-azabicyclo[3.2.1]oct-3-yl)-benzamide To a solution of methanesulfonyl acetic acid (20.7 mg, 0.15 mmol) in DMF (0.2 mL) was added N,N-carbonyl diimidazole (24.3 mg, 0.15 mmol) at room temperature. Thirty minutes later, to the stirred mixture was added DIPEA (25.8 mg, 0.20 mmol) and 3-endo-{8-[3-(cyclohexylmethylamino)-propyl]-8-aza-bicyclo[3.2.1]oct-3-yl}-benzamide bis TFA (30.0 mg, 0.05 mmol). The resulting reaction mixture was then heated at 65° C. for 3 h, concentrated, dissolved in 50% acetic acid in water (1.5 mL), filtered and purified by reverse phase preparative HPLC to give title compound as its TFA salt (16.0 mg). (m/z): [M+H]$^+$ calcd for $C_{27}H_{41}N_3O_4S$ 504.28; found 504.2.

Example 133: Synthesis of 3-endo-(8-{3-[benzyl-(2-hydroxyacetyl)amino]-propyl}-8-azabicyclo[3.2.1]oct-3-yl)-benzamide Using the process of Example 130, 3-endo-[8-(3-benzylaminopropyl)-8-aza-bicyclo[3.2.1]oct-3-yl]-benzamide bis TFA salt (100 mg, 0.165 mmol) was reacted with acetoxyacetyl chloride (24.5 mg, 0.18 mmol) to provide the TFA salt of the title compound (22.6 mg). $^1$H NMR (CD$_3$OD, 400M Hz) δ (ppm): 8.08 (s, 1H), 7.77-7.81 (m, 2H), 7.51 (t, J=7.6, 8.0 Hz, 1H), 7.31-7.46 (m, 5H), (m/z): [M+H]$^+$ calcd for $C_{26}H_{33}N_3O_3$ 436.25; found 436.4.

Example 134: Synthesis of 3-endo-(8-{3-[benzyl-((S)-2-hydroxypropionyl)-amino]propyl}-8-azabicyclo[3.2.1]oct-3-yl)-benzamide a. Preparation of benzyl-(3-hydroxypropyl)-carbamic Acid tert-butyl Ester To a mixture of 3-benzylamino-1-propanol HCl salt (2.0 g, 9.9 mmol) in DCM (49.0 mL) at 0° C. was added DIPEA (1.72 mL, 9.9 mmol) followed by a solution of di-tert-butyl-dicarbonate (1.94 g, 8.91 mmol) in DCM (20.0 mL). After being stirred for 3 h at 0° C., the reaction mixture was washed sequentially with 1N HCl (2×10.0 mL), saturated sodium bicarbonate (10.0 mL) and brine (10.0 mL), dried over sodium sulfate, filtered, and concentrated to give a yellowish oil (2.22 g). $^1$H NMR (CDCl$_3$, 300 MHz) δ (ppm): 7.20-7.39 (m, 5H), 4.40 (s, 2H), 3.55 (brs, 2H), 3.38 (brs, 2H), 1.61 (brs, 2H), 1.44 (s, 9H).

b. Preparation of benzyl-(3-oxo-propyl)-carbamic Acid tert-butyl Ester

To the solution of the product of the previous step (2.22 g, 7.38 mmol) in DCM (37.0 mL) at 0° C. was added DIPEA (2.38 g, 18.45 mmol) followed by DMSO (0.86 g, 11.07 mmol) and pyridine sulfur trioxide complex (2.93 g, 18.45 mmol). After being stirred for 30 min at 0° C., the reaction mixture was diluted with DCM (20.0 mL) and washed sequentially with 1N HCl (10.0 mL), saturated sodium bicarbonate (10.0 mL) and brine (10.0 mL), dried over sodium sulfate, filtered and concentrated to give a yellowish oil which was further purified by normal phase chromatography to give the title compound as a colorless oil (1.54 g). $^1$H NMR (CDCl$_3$, 300M Hz) δ (ppm): 9.73 (s, 1H), 7.24-7.36 (m, 5H), 4.45 (s, 2H), 3.51 (brs, 2H), 2.65 (brs, 2H), 1.46 (s, 9H).

c. Preparation of 3-endo-[8-(3-benzylamino-propyl)-8-azabicyclo[3.2.1]oct-3-yl]-benzamide To a solution of the product from previous step (972.6 mg, 3.25 mmol) in DCM (16.0 mL) at room temperature was added 3-(8-azabicyclo[3.2.1]oct-3-yl)-benzamide (747.5 mg, 3.25 mmol) followed by sodium triacetoxyborohydride (826.6 mg, 3.9 mmol). The resulting mixture was stirred at room temperature for 30 min before it was diluted with DCM (40.0 mL). The organic layer was washed with saturated sodium bicarbonate (20.0 mL) followed by brine (20.0 mL), dried over sodium sulfate, filtered and concentrated to give a yellowish oil. The oily residue was treated with a mixture of TFA (5.0 mL) and DCM (5.0 mL) at room temperature for 30 min. Then it was concentrated and the resulting residue was dissolved in a mixture of water (4.0 mL) and acetonitrile (3.0 mL), filtered and purified by reverse phase preparative HPLC to give the title compound as its bis TFA salt (1.22 g). $^1$H NMR (CD$_3$OD, 400 MHz) δ (ppm): 8.06 (s, 1H), 7.74-7.78 (m, 2H), 7.46-7.53 (m, 6H), 4.27 (s, 2H), 4.08 (br s, 2H), 3.35-3.38 (obscure 1H, partially overlap with solvent), 3.20 (t, J=8.0 Hz, 2H), 3.12 (t, J=8.4 Hz, 2H), 2.62-2.78 (m, 4H), 2.21-2.29 (m, 2H), 2.09-2.12 (m, 2H), 1.79-1.84 (m, 2H). (m/z): [M+H]+ calcd for $C_{24}H_{31}N_3O$ 378.25; found 378.4.

d. Synthesis of 3-endo-(8-{3-[benzyl-((S)-2-hydroxy-propionyl)amino]propyl}-8-aza-bicyclo[3.2.1]oct-3-yl)-benzamide To a solution of the product of the previous step (30.0 mg, 0.06 mmol) in DCM (0.5 mL) was added DIPEA (32.4 mg, 0.24 mmol) followed by acetoxyacetyl chloride (9.8 mg, 0.072 mmol) at room temperature. The reaction completed instantly. After concentration, the resulting residue was redissolved in methanol (0.5 mL) and treated with lithium hydroxide monohydrate (15.1 mg, 0.36 mmol) for overnight. The reaction was concentrated and the residue was dissolved in 50% acetic acid in water (1.5 mL), filtered and purified by reverse phase prep HPLC to give the title compound as its TFA salt (23.4 mg). (m/z): [M+H]$^+$ calcd for $C_{27}H_{35}N_3O_3$ 450.27; found 450.4.

Examples 135-199

Using processes described in the above examples, the following additional compounds were prepared by reaction of the corresponding intermediate of formula (II) with a suitable acid chloride, carboxylic acid or carboxylate reagent as depicted in Scheme A (i), followed in specific instances by an N-alkylation step. The intermediates of formula (II) were prepared by reaction of an aldehyde of formula (IV) with an azabicyclooctyl benzamide according to the process of Example 134 (c), as depicted in Scheme B. The aldehydes of formula (IV) were prepared using the general process depicted in Scheme F, as described, for example, in Example 134 (a) and (b).

Example 135

3-endo-(8-{2-[((S)-2,3-dihydroxypropionyl)phenethyl-amino]ethyl}-8-azabicyclo[3.2.1]oct-3-yl)-benzamide TFA salt (m/z): [M+H]$^+$ calcd for $C_{27}H_{35}N_3O_4$ 466.27; found 466.4.

Example 136

3-endo-(8-{2-[(2-methanesulfonylacetyl)phenethylamino]ethyl}-8-azabicyclo[3.2.1]oct-3-yl)-benzamide TFA salt (m/z): [M+H]$^+$ calcd for $C_{27}H_{35}N_3O_4S$ 498.23; found 498.4.

Example 137 acetic acid (benzyl-{2-[3-endo-(3-hydroxyphenyl)-8-azabicyclo[3.2.1]oct-8-yl]-ethyl}carbamoyl)methyl ester TFA salt (m/z): [M+H]$^+$ calcd for $C_{26}H_{32}N_2O_4$ 437.24; found 437.4.

Example 138

3-endo-(8-{2-[benzyl-((S)-2,3-dihydroxypropionyl)amino]ethyl}-8-aza-bicyclo[3.2.1]oct-3-yl)-benzamide TFA salt $^1$H NMR (CD$_3$OD, 400 MHz) δ (ppm): 8.05 (s, 1H), 7.79 (d, J=7.6 Hz, 1H), 7.74 (d, J=8.0 Hz, 1H), 7.37-7.52 (m, 6H), 4.90-4.95 (m, 1H), 4.77-4.83 (m, 1H), 4.72 (t, J=5.2 Hz, 1H), 4.10 (brs, 2H), 3.85-3.91 (m, 3H), 3.63-3.69 (m, 1H), 3.31-3.34 (obscure 1H, partially overlap with solvent), 3.09-3.12 (m, 2H), 2.64 (brs, 4H), 2.04-2.07 (m, 2H), 1.80-1.83 (m, 2H); (m/z): [M+H]$^+$ calcd for $C_{26}H_{33}N_3O_4$ 452.25; found 452.2.

Example 139

3-endo-(8-{3-[benzyl-((S)-2,3-dihydroxypropionyl)amino]propyl}-8-azabicyclo[3.2.1]oct-3-yl)-benzamide TFA salt (m/z): [M+H]+ calcd for $C_{27}H_{35}N_3O_4$ 466.26; found 466.4.

Example 140

3-endo-(8-{3-[benzyl-((R)-2,3-dihydroxypropionyl)amino]propyl}-8-azabicyclo[3.2.1]oct-3-yl)-benzamide TFA salt (m/z): [M+H]$^+$ calcd for $C_{27}H_{35}N_3O_4$ 466.26; found 466.4.

Example 141

3-endo-(8-{3-[benzyl-(2,3-dihydroxybutyryl)amino]propyl}-8-azabicyclo[3.2.1]oct-3-yl)-benzamide TFA salt (m/z): [M+H]$^+$ calcd for $C_{28}H_{37}N_3O_4$ 480.28; found 480.4.

Example 142

3-endo-(8-{3-[benzyl-(2-methanesulfonylacetyl)amino]propyl}-8-azabicyclo[3.2.1]oct-3-yl)-benzamide TFA salt $^1$H NMR (CD$_3$OD, 400 MHz) δ (ppm): 8.04 (s, 1H), 7.72-7.77 (m, 2H), 7.48 (t, J=7.6 Hz, 1H), 7.31-7.37 (m, 5H), 4.79 (s, 2H), 4.49 (s, 2H), 3.99&3.92 (two sets of brs, 2H), 3.61 (t, J=6.4 Hz, 2H), 3.34-3.38 (m, 1H), 3.22 (s, 3H), 2.98 (t, J=8.0 Hz, 2H), 2.53-2.72 (m, 4H), 1.96-2.11 (m, 4H), 1.74-1.80 (m, 2H). (m/z): [M+H]$^+$ calcd for $C_{27}H_{35}N_3O_4S$ 498.23; found 498.2.

Example 143

3-endo-(8-{3-[benzyl-(2-hydroxy2-methylpropionyl)amino]-propyl}-8-azabicyclo[3.2.1]oct-3-yl)-benzamide TFA salt (m/z): [M+H]$^+$ calcd for $C_{28}H_{37}N_3O_3$ 464.28; found 464.4.

Example 144

3-endo-(8-{3-[benzyl-(2,2-dimethylpropionyl)amino]propyl}-8-azabicyclo[3.2.1]oct-3-yl)-benzamide TFA salt (m/z): [M+H]$^+$ calcd for $C_{29}H_{39}N_3O_2$ 462.30; found 462.4.

Examples 145

3-endo-(8-{2-[(4,4-difluoro-cyclohexylmethyl)-(3-hydroxy-2-hydroxymethyl-2-methylpropionyl)amino]ethyl}-8-azabicyclo[3.2.1]oct-3-yl)-benzamide TFA salt (m/z): [M+H]$^+$ calcd for $C_{28}H_{41}F_2N_3O_4$ 522.31; found 522.2.

Example 146

3-endo-(8-{2-[(4,4-difluorocyclohexylmethyl)-((S)-2,3-dihydroxy-propionyl)amino]ethyl}-8-azabicyclo[3.2.1]oct-3-yl)-benzamide TFA salt (m/z): [M+H]$^+$ calcd for $C_{26}H_{37}F_2N_3O_4$ 494.28; found 494.4.

Example 147

3-endo-(8-{2-[(4,4-difluorocyclohexylmethyl)-((R)-2,3-dihydroxy-propionyl)amino]ethyl}-8-azabicyclo[3.2.1]oct-3-yl)-benzamide TFA salt (m/z): [M+H]$^+$ calcd for $C_{26}H_{37}F_2N_3O_4$ 494.28; found 494.4.

Example 148

3-endo-(8-{2-[(4,4-difluorocyclohexylmethyl)-(2-methanesulfonylacetyl)amino]ethyl}-8-azabicyclo[3.2.1]oct-3-yl)-benzamide TFA salt $^1$H NMR (CD$_3$OD, 400 MHz) δ (ppm): 8.06 (s, 1H), 7.79 (d, J=7.6 Hz, 1H), 7.75 (d, J=8.8 Hz, 1H), 7.51 (dd, J=7.6, 8.0 Hz, 1H), 4.51 (s, 2H), 4.18 (deformed m, 2H), 3.89 (t, J=6.0 Hz, 2H), 3.48 (d, J=7.2 Hz, 2H), 3.28 (s, 3H), 3.24 (t, J=6.0 Hz, 2H), 2.65-2.68 (m, 4H), 2.10-2.19 (m, 4H), 1.75-1.90 (m, 7H), 1.36-1.45 (m, 2H). (m/z): [M+H]$^+$ calcd for $C_{26}H_{37}F_2N_3O_4S$ 526.25; found 526.4.

Example 149

3-endo-(8-{2-[(4,4-difluorocyclohexylmethyl)-((S)-4-dimethylamino-2-hydroxybutyryl)amino]ethyl}-8-azabicyclo[3.2.1]oct-3-yl)-benzamide bis TFA salt (m/z): [M+H]+ calcd for $C_{29}H_{44}F_2N_4O_3$ 535.34; found 535.4.

Example 150

3-endo-(8-2-[(4,4-difluorocyclohexylmethyl)-((S)-2-hydroxypropionyl)-amino]ethyl-8-azabicyclo[3.2.1]oct-3-yl)-benzamide TFA salt $^1$H NMR (CD$_3$OD, 400 MHz) δ (ppm): 8.05 (s, 1H), 7.78 (d, J=7.6 Hz, 1H), 7.74 (d, J=7.6 Hz, 1H), 7.49 (dd, J=7.6 Hz, 1H), 4.64 (q, J=6.0 Hz, 1H), 4.10-4.14 (m, 2H), 3.72-3.86 (m, 1H), 3.32-3.46 (obscure m, 3H, partially overlap with solvent), 3.18 (t, J=5.6 Hz, 2H), 2.64-2.67 (m, 4H), 2.11-2.16 (m, 4H), 1.78-1.88 (m, 7H), 1.37-1.43 (m, 5H); (m/z): [M+H]$^+$ calcd for $C_{26}H_{37}F_2N_3O_3$ 478.28; found 478.4.

Example 151

3-endo-(8-{2-[(4-fluorocyclohexylmethyl)-((S)-2,3-dihydroxy-propionyl)amino]ethyl}-8-azabicyclo[3.2.1]oct-3-yl)-benzamide TFA salt (m/z): [M+H]$^+$ calcd for $C_{26}H_{38}FN_3O_4$ 476.28; found 476.4.

Example 152

3-endo-(8-{2-[(4-fluorocyclohexylmethyl)-(2-hydroxyacetyl)amino]-ethyl}-8-azabicyclo[3.2.1]oct-3-yl)-benzamide TFA salt (m/z): [M+H]$^+$ calcd for $C_{25}H_{36}FN_3O_3$ 446.27; found 446.4.

Example 153

3-endo-(8-{2-[cyclopentylmethyl-(3-hydroxy-2-hydroxymethyl-2-methyl-propionyl)amino]ethyl}-8-azabicyclo[3.2.1]oct-3-yl)-benzamide TFA salt (m/z): [M+H]$^+$ calcd for $C_{27}H_{41}N_3O_4$ 472.31; found 472.4.

Example 154

3-endo-(8-{2-[cyclopentylmethyl-((S)-2,3-dihydroxypropionyl)-amino]ethyl}-8-azabicyclo[3.2.1]oct-3-yl)-benzamide TFA salt (m/z): [M+H]$^+$ calcd for $C_{25}H_{37}N_3O_4$ 444.28; found 444.4.

Example 155

3-endo-(8-{2-[cyclopentylmethyl-((R)-2,3-dihydroxypropionyl)-amino]ethyl}-8-azabicyclo[3.2.1]oct-3-yl)-benzamide TFA salt (m/z): [M+H]$^+$ calcd for $C_{25}H_{37}N_3O_4$ 444.28; found 444.4.

Example 156

3-endo-(8-{2-[cyclopentylmethyl-(2-methanesulfonylacetyl)-amino]ethyl}-8-azabicyclo[3.2.1]oct-3-yl)-benzamide TFA salt (m/z): [M+H]$^+$ calcd for $C_{25}H_{37}N_3O_4S$ 476.25; found 476.2.

Example 157

3-endo-(8-{2-[cyclopentylmethyl-(2-hydroxyacetyl)amino]-ethyl}-8-azabicyclo[3.2.1]oct-3-yl)-benzamide (m/z): [M+H]+ calcd for $C_{24}H_{35}N_3O_3$ 414.27; found 414.4.

Example 158

3-endo-(8-{2-[cyclobutylmethyl-(3-hydroxy-2-hydroxymethyl-2-methyl-propionyl)-amino]ethyl}-8-azabicyclo[3.2.1]oct-3-yl)-benzamide TFA salt (m/z): [M+H]$^+$ calcd for $C_{26}H_{39}N_3O_4$ 458.29; found 458.4.

Example 159

3-endo-(8-{2-[cyclobutylmethyl-((S)-2,3-dihydroxypropionyl)-amino]ethyl}-8-azabicyclo[3.2.1]oct-3-yl)-benzamide TFA salt (m/z): [M+H]$^+$ calcd for $C_{24}H_{35}N_3O_4$ 430.26; found 430.4.

Example 160

3-endo-(8-{2-[cyclobutylmethyl-((R)-2,3-dihydroxypropionyl)-amino]ethyl}-8-azabicyclo[3.2.1]oct-3-yl)-benzamide TFA salt (m/z): [M+H]$^+$ calcd for $C_{24}H_{35}N_3O_4$ 430.26; found 430.4.

Example 161

3-endo-(8-{2-[cyclobutylmethyl-(2-methanesulfonylacetyl)-amino]ethyl}-8-azabicyclo[3.2.1]oct-3-yl)-benzamide TFA salt (m/z): [M+H]$^+$ calcd for $C_{24}H_{35}N_3O_4S$ 462.23; found 462.2.

Example 162

3-endo-(8-{2-[cyclobutylmethyl-(2-methanesulfonyl-2-methyl-propionyl)amino]ethyl}-8-azabicyclo[3.2.1]oct-3-yl)-benzamide TFA salt (m/z): [M+H]$^+$ calcd for $C_{26}H_{39}N_3O_4S$ 490.27; found 490.2.

Example 163

3-endo-(8-{2-[cyclobutylmethyl-(2-hydroxyacetyl)amino]ethyl}-8-azabicyclo[3.2.1]oct-3-yl)-benzamide TFA salt (m/z): [M+H]$^+$ calcd for $C_{23}H_{33}N_3O_3$ 400.25; found 400.4.

Example 164

3-endo-(8-{2-[cyclobutylmethyl-((S)-2-hydroxypropionyl)amino]ethyl}-8-azabicyclo[3.2.1]oct-3-yl)-benzamide TFA salt (m/z): [M+H]$^+$ calcd for $C_{24}H_{35}N_3O_3$ 414.27; found 414.4.

Example 165

3-endo-(8-{2-[benzyl-(2-methanesulfonylacetyl)amino]ethyl}-8-aza-bicyclo[3.2.1]oct-3-yl)-benzamide TFA salt (m/z): [M+H]$^+$ calcd for $C_{26}H_{33}N_3O_4S$, 484.22; found, 484.2; $^1$H NMR (CD$_3$OD, 400 MHz) δ (ppm): 8.01 (s, 1H), 7.76 (d, J=7.6 Hz, 1H), 7.70 (d, J=8.0 Hz, 1H), 7.49-7.35 (m, 6H), 4.80 (s, 2H), 4.57 (s, 2H) 4.07 (br s, 2H), 3.80 (t, J=6.0 Hz, 2H), 3.4-3.3 (obscure, 1H, overlap with solvent), 3.25 (s, 3H), 3.08 (t, J=6 Hz, 2H), 2.61-2.60 (m, 4H), 2.03-2.00 (m, 2H), 1.82-1.79 (m, 2H).

Example 166

3-endo-(8-{2-[benzyl-(2-hydroxy-2-methylpropionyl)amino]ethyl}-8-aza-bicyclo[3.2.1]oct-3-yl)-benzamide TFA salt (m/z): [M+H]$^+$ calcd for $C_{27}H_{35}N_3O_3$, 450.27; found, 450.2.

Example 167

3-endo-(8-{2-[benzyl-((S)-2-hydroxy-1-oxopropyl)amino]ethyl}-8-aza-bicyclo[3.2.1]oct-3-yl)-benzamide TFA salt (m/z): [M+H]$^+$ calcd for $C_{26}H_{33}N_3O_3$, 436.25; found, 436.5; $^1$H NMR (CD$_3$OD, 400 MHz) δ (ppm): 8.02 (s, 1H), 7.77-7.70 (m, 2H), 7.50-7.32 (m, 6H), 4.83-4.71 (m, 2H), 4.07-4.01 (m, 2H), 3.81 (m, 1H), 3.64 (m, 1H), 3.03 (t, J=6.0 Hz, 2H), 2.63-2.60 (m, 4H), 2.03-1.94 (m, 2H), 1.80-1.77 (m, 2H), 1.40 (d, J=6.4 Hz, 3H).

Example 168

3-endo-(8-{2-[benzyl-(2,2-dimethylpropionyl)amino]ethyl}-8-aza-bicyclo[3.2.1]oct-3-yl)-benzamide TFA salt (m/z): [M+H]$^+$ calcd for $C_{28}H_{37}N_3O_2$, 448.29; found, 448.

Example 169

3-endo-{8-[2-(benzyl-methanesulfonylamino)ethyl]-8-aza-bicyclo[3.2.1]oct-3-yl}-benzamide TFA salt (m/z): [M+H]$^+$ calcd for $C_{24}H_{31}N_3O_3S$, 442.21; found, 442.2.

Example 170

3-endo-(8-{2-[benzyl-(2-methoxyacetyl)-amino]ethyl}-8-aza-bicyclo[3.2.1]oct-3-yl)-benzamide TFA salt (m/z): [M+H]$^+$ calcd for $C_{26}H_{33}N_3O_3$, 436.25; found, 436.5.

Example 171

3-endo-(8-{2-[benzyl-(3-hydroxy-2,2-dimethylpropionyl)amino]ethyl}-8-aza-bicyclo[3.2.1]oct-3-yl)-benzamide TFA salt (m/z): [M+H]$^+$ calcd for $C_{28}H_{37}N_3O_3$, 464.28; found, 464.2.

Example 172

3-endo-(8-{2-[benzyl-(1-hydroxy-cyclopropanecarbonyl)amino]ethyl}-8-aza-bicyclo[3.2.1]oct-3-yl)-benzamide TFA salt (m/z): [M+H]$^+$ calcd for $C_{27}H_{33}N_3O_3$, 448.25; found, 448.3.

Example 173

3-endo-(8-{2-[benzyl-(2-cyanoacetyl)amino]ethyl}-8-aza-bicyclo[3.2.1]oct-3-yl)-benzamide TFA salt (m/z): [M+H]$^+$ calcd for $C_{26}H_{30}N_4O_2$, 431.24; found, 431.5.

Example 174

3-endo-(8-{2-[benzyl-((R)-3-hydroxy-2-(S)-hydroxybutyryl)amino]-ethyl}-8-azabicyclo[3.2.1]oct-3-yl)-benzamide TFA salt (m/z): [M+H]$^+$ calcd for $C_{27}H_{35}N_3O_4$, 466.26; found, 466.4.

Example 175

3-endo-(8-{2-[benzyl-((R)-2,3-dihydroxypropionyl)amino]ethyl}-8-aza-bicyclo[3.2.1]oct-3-yl)-benzamide TFA salt (m/z): [M+H]$^+$ calcd for $C_{26}H_{33}N_3O_4$, 452.25; found, 452.2.

Example 176

3-endo-(8-{2-[cyclopentylmethyl-(3-hydroxypropionyl)amino]ethyl}-8-azabicyclo[3.2.1]oct-3-yl)-benzamide TFA salt (m/z): [M+H]$^+$ calcd for $C_{25}H_{37}N_3O_3$, 428.28; found, 428.4.

Example 177

3-endo-(8-{2-[cyclopentylmethyl-(3-hydroxy-2,2-dimethylpropionyl)-amino]ethyl}-8-azabicyclo[3.2.1]oct-3-yl)-benzamide TFA salt (m/z): [M+H]$^+$ calcd for $C_{27}H_{41}N_3O_3$, 456.31; found, 456.5.

Example 178

3-endo-(8-{2-[cyclopentylmethyl-(trans-4-hydroxycyclohexanecarbonyl)-amino]ethyl}-8-azabicyclo[3.2.1]oct-3-yl)-benzamide TFA salt (m/z): [M+H]$^+$ calcd for $C_{29}H_{43}N_3O_3$, 482.33; found, 482.5.

Example 179

3-endo-(8-{2-[cyclopentylmethyl-(2,2-dimethylpropionyl)amino]ethyl}-8-azabicyclo[3.2.1]oct-3-yl)-benzamide TFA salt (m/z): [M+H]$^+$ calcd for $C_{27}H_{41}N_3O$, 440.32; found, 440.4.

Example 180

3-endo-{8-[2-(cyclopentylmethyl-methanesulfonylamino)ethyl]-8-aza-bicyclo[3.2.1]oct-3-yl}-benzamide TFA salt (m/z): [M+H]$^+$ calcd for $C_{23}H_{35}N_3O_3S$, 434.24; found, 434.2.

Example 181

3-endo-(8-{2-[(2-hydroxyacetyl)-(4-trifluoromethylbenzyl)-amino]ethyl}-8-aza-bicyclo[3.2.1]oct-3-yl)-benzamide TFA salt (m/z): [M+H]$^+$ calcd for $C_{26}H_{30}F_3N_3O_3$, 490.22; found, 490.4.

Example 182

3-endo-(8-(2-((4-trifluoromethylbenzyl)(N,N-dimethylsulfamoyl)aminoethyl)-8-azabicyclo[3.2.1]oct-3-yl)-benzamide TFA salt (m/z): [M+H]$^+$ calcd for $C_{26}H_{33}F_3N_4O_3S$, 539.22; found, 539.5.

Example 183

3-endo-(8-{2-[(2-methanesulfonylacetyl)-(4-trifluoromethyl-benzyl)amino]ethyl}-8-azabicyclo[3.2.1]oct-3-yl)-benzamide TFA salt (m/z): [M+H]$^+$ calcd for $C_{27}H_{32}F_3N_3O_4S$, 552.21; found, 552.4; $^1$H NMR (CD$_3$OD, 400 MHz) δ (ppm): 8.02 (s, 1H), 7.77-7.70 (m, 4H), 7.56-7.54 (m, 3H)) 4.94 (s, 2H), 4.56 (s, 2H), 4.12 (br s, 2H), 3.80 (t, J=5.6 Hz, 2H), 3.4-3.3 (obscure, 1H, overlap with solvent), 3.26 (s, 3H), 3.17 (t, J=5.6 Hz, 2H), 2.63-2.61 (m, 4H), 2.10-2.06 (m, 2H), 1.84-1.81 (m, 2H).

Example 184

3-endo-(8-{2-[(4-fluorobenzyl)-(2-methanesulfonylacetyl)amino]ethyl}-8-azabicyclo[3.2.1]oct-3-yl)-benzamide TFA salt (m/z): [M+H]$^+$ calcd for $C_{26}H_{32}FN_3O_4S$, 502.21; found, 502.4; $^1$H NMR (CD$_3$OD, 400 MHz) δ (ppm): 8.01 (s, 1H), 7.77-7.68 (m, 2H), 7.46 (t, J=8.0 Hz, 1H), 7.40-7.36 (m, 2H), 7.15 (t, J=8.8 Hz, 2H), 4.79 (s, 2H) 4.10 (br s, 2H), 3.78 (t, J=6.0 Hz, 2H), 3.4-3.3 (obscure, 1H, overlap with solvent), 3.25 (s, 3H), 3.11 (t, J=5.6 Hz, 2H), 2.61-2.60 (m, 4H), 2.06-2.03 (m, 2H), 1.80-1.78 (m, 2H).

Example 185

3-endo-(8-{2-[(4-fluorobenzyl)-(2-hydroxyacetyl)amino]ethyl}-8-azabicyclo[3.2.1]oct-3-yl)-benzamide TFA salt ((m/z): [M+H]$^+$ calcd for $C_{25}H_{30}FN_3O_3$, 440.23; found, 440.4.

Example 186

3-endo-(8-(2-((4-fluoromethylbenzyl)(N,N-dimethylsulfamoyl)-amino)ethyl)-8-azabicyclo[3.2.1]oct-3-yl)-benzamide TFA salt (m/z): [M+H]$^+$ calcd for $C_{25}H_{33}FN_4O_3S$, 489.23; found, 489.5.

Example 187

3-endo-(8-{2-[[2-(3-fluorophenyl)ethyl]-(2-hydroxyacetyl)amino]-ethyl}-8-azabicyclo[3.2.1]oct-3-yl)-benzamide TFA salt (m/z): [M+H]$^+$ calcd for $C_{26}H_{32}FN_3O_3$, 454.24; found, 454.2.

Example 188

3-endo-(8-{2-[[2-(4-fluorophenyl)ethyl]-(2-hydroxyacetyl)amino]-ethyl}-8-aza-bicyclo[3.2.1]oct-3-yl)-benzamide TFA salt (m/z): [M+H]$^+$ calcd for $C_{26}H_{32}FN_3O_3$, 454.24; found, 454.4; $^1$H NMR (CD$_3$OD, 400 MHz) δ (ppm): 8.03 (s, 1H), 7.77-7.71 (m, 2H), 7.47 (t, J=8.0 Hz, 1H), 7.30-7.26 (m, 2H), 7.08-7.04 (m, 2H), 4.13 (br s, 2H) 4.08 (s, 2H), 3.78 (t, J=5.2 Hz, 2H), 3.52 (t, J=7.2 Hz, 2H), 3.4-3.3 (obscure, 1H, overlap with solvent), 3.17 (t, J=5.6 Hz, 2H), 2.91 (t, J=7.6 Hz, 2H), 2.65-2.61 (m, 4H), 2.14-2.11 (m, 2H), 1.85-1.82 (m, 2H).

Example 189

3-endo-(8-{2-[[2-(4-fluorophenyl)ethyl]-(2-methanesulfonyl-acetyl)amino]ethyl}-8-aza-bicyclo[3.2.1]oct-3-yl)-benzamide TFA salt (m/z): [M+H]$^+$ calcd for $C_{27}H_{34}F_2N_3O_4S$, 516.23; found, 516.4; $^1$H NMR (CD$_3$OD, 400 MHz) δ (ppm): 8.01 (s, 1H), 7.76 (d, J=7.6 Hz, 1H), 7.70 (d, J=8.0 Hz, 1H) 7.49-7.45 (m, 1H), 7.32 (m, 2H), 7.08 (m, 2H), 4.21 (s, 2H), 4.11 (br s, 2H), 3.79-3.73 (m, 2H), 3.4-3.3 (obscure, 1H, overlap with solvent), 3.19 (s, 3H), 3.16 (t, J=5.6 Hz, 2H), 2.97 (t, J=7.2 Hz, 2H), 2.63-2.60 (m, 4H), 2.12-2.09 (m, 2H), 1.83-1.80 (m, 2H).

Example 190

3-endo-[8-(2-{(2-hydroxyacetyl)-[2-(4-hydroxyphenyl)ethyl]-amino}ethyl)-8-azabicyclo[3.2.1]oct-3-yl]-benzamide TFA salt (m/z): [M+H]$^+$ calcd for $C_{26}H_{33}N_3O_4$, 452.25; found, 452.2.

Example 191

3-endo-(8-{2-[[2-(4-hydroxyphenyl)ethyl]-(2-methanesulfonyl-acetyl)amino]ethyl}-8-azabicyclo[3.2.1]oct-3-yl)-benzamide TFA salt (m/z): [M+H]$^+$ calcd for $C_{27}H_{35}N_3O_5S$, 514.23; found, 514.3.

Example 192

3-endo-(8-{2-[(3-fluorobenzyl)-(2-hydroxyacetyl)amino]ethyl}-8-azabicyclo[3.2.1]oct-3-yl)-benzamide TFA salt (m/z): [M+H]$^+$ calcd for $C_{25}H_{30}FN_3O_3$, 440.23; found, 440.4; $^1$H NMR (CD3OD, 400 MHz) δ (ppm): 8.03 (s, 1H), 7.77-7.71 (m, 2H), 7.49-7.43 (m, 2H), 7.13-7.06 (m, 3H), 4.62 (s, 2H), 4.37 (s, 2H) 4.12 (br s, 2H), 3.75 (t, J=5.6 Hz, 2H), 3.4-3.3 (obscure, 1H, overlap with solvent), 3.12 (t, J=5.6 Hz, 2H), 2.64-2.62 (m, 4H), 2.09-2.06 (m, 2H), 1.84-1.81 (m, 2H)

Example 193

3-endo-(8-{2-[(3-fluorobenzyl)-(2-methanesulfonyl-acetyl)-amino]ethyl}-8-azabicyclo[3.2.1]oct-3-yl)-benzamide TFA salt (m/z): [M+H]$^+$ calcd for $C_{26}H_{32}FN_3O_4S$, 502.21; found, 502.4; $^1$H NMR (CD$_3$OD, 400 MHz) δ (ppm): 8.02 (s, 1H), 7.77-7.70 (m, 2H), 7.49-7.45 (m, 2H), 7.19-7.11 (m, 3H), 4.8-4.9 (obscure, 2H, overlap with solvent), 4.56 (s, 2H) 4.10 (br s, 2H), 3.80 (t, J=5.6 Hz, 2H), 3.4-3.3 (obscure, 1H, overlap with solvent), 3.25 (s, 3H), 3.13 (t, J=6.0 Hz, 2H), 2.63-2.60 (m, 4H), 2.08-2.05 (m, 2H), 1.83-1.80 (m, 2H).

Example 194

3-endo-(8-{2-[(2,2-difluoro-2-phenylethyl)-((S)-2,3-dihydroxy-propionyl)amino]ethyl}-8-azabicyclo[3.2.1]oct-3-yl)-benzamide TFA salt (m/z): [M+H]$^+$ calcd for $C_{27}H_{33}F_2N_3O_4$, 502.24; found, 502.4.

Example 195

3-endo-(8-{2-[(2-methanesulfonylacetyl)-(4-methyl-cyclohexylmethyl)amino]ethyl}-8-azabicyclo[3.2.1]oct-3-yl)-benzamide TFA salt (m/z): [M+H]$^+$ calcd for $C_{27}H_{41}N_3O_4S$, 504.28; found, 504.4.

Example 196

3-endo-(8-{2-[((S)-2,3-dihydroxypropionyl)-(4-methyl-cyclohexyl-methyl)amino]ethyl}-8-azabicyclo[3.2.1]oct-3-yl)-benzamide TFA salt (m/z): [M+H]$^+$ calcd for $C_{27}H_{41}N_3O_4$, 472.31; found, 472.4.

Example 197

3-endo-(8-{2-[(2-hydroxy-acetyl)(4-trifluoromethyl-cyclohexyl-methyl)amino]ethyl}-8-azabicyclo[3.2.1]oct-3-yl)-benzamide TFA salt (m/z): [M+H]$^+$ calcd for $C_{26}H_{36}F_3N_3O_3$, 496.27; found, 496.4.

Example 198

3-endo-(8-{2-[(2-methanesulfonylacetyl)-(4-trifluoromethyl-cyclohexyl-methyl)amino]ethyl}-8-azabicyclo[3.2.1]oct-3-yl)-benzamide TFA salt (m/z): [M+H]$^+$ calcd for $C_{27}H_{38}F_3N_3O_4S$, 558.25; found, 558.4.

Example 199

3-endo-8-{2-[((S)-2,3-dihydroxypropionyl)-(4-trifluoromethyl-cyclohexylmethyl)amino]ethyl}-8-azabicyclo[3.2.1]oct-3-yl)-benzamide TFA salt (m/z): [M+H]$^+$ calcd for $C_{27}H_{38}F_3N_3O_4$, 526.28; found, 526.4.

Example 200: Synthesis of 3-endo-(8-{2-[cyclohexylmethyl-((R)-2,3-dihydroxy-propionyl)-amino]-ethyl}-8-aza-bicyclo[3.2.1]oct-3-yl)-benzamide a. Preparation of Lithium (R)-2,2-dimethyl-1,3-dioxolane-4-carboxylate

To a solution of (R)-2,2-dimethyl-1,3-dioxolane-4-carboxylic acid methyl ester (5.0 g, 31.25 mmol) in MeOH (32.0 mL) at room temperature was added a solution of lithium hydroxide monohydrate (1.31 g, 31.25 mmol) in water (10.0 mL). The resulting mixture was stirred for thirty min before it was concentrated. The resulting white solid was further dried under vacuum to give the title compound (4.59 g).

b. Preparation of (R)-2,2-dimethyl-[1,3]dioxolane-4-carboxylic Acid {2-[3-endo-(3-carbamoyl-phenyl)-8-azabicyclo[3.2.1]oct-8-yl]ethyl}cyclohexylmethyl-amide 3-endo-{8-[2-(Cyclohexylmethylamino)-ethyl]-8-azabicyclo[3.2.1]oct-3-yl}-benzamide (600 mg, 1.6 mmol) was dissolved in DMF (5 mL) and lithium (R)-2,2-dimethyl-[1,3]dioxolane-4-carboxylate (270 mg, 1.78 mmol) was added as a solid. The solution was stirred at room temperature until the solid dissolved, then HATU (687 mg, 1.78 mmol) was added as a solid. The bright yellow solution was stirred at room temperature overnight. The reaction was diluted with ethyl acetate (100 mL). The organic solution was washed with saturated aqueous sodium bicarbonate and saturated aqueous sodium chloride. The organic solution was dried over anhydrous sodium sulfate and solvent was removed in vacuo to yield the title compound (781 mg) as a crude yellow oil.

c. Synthesis of 3-endo-(8-{2-[cyclohexylmethyl-((R)-2,3-dihydroxy-propionyl)-amino]-ethyl}-8-azabicyclo[3.2.1]oct-3-yl)-benzamide The crude product of the previous step was dissolved in acetonitrile (10 mL) and 1N HCl (aqueous) (10 mL) was added. The yellow solution was stirred at room temperature for 2 h; then the reaction was concentrated under vacuum. The crude material was dissolved in acetonitrile/water/TFA and purified by preparative HPLC to give the TFA salt of the title compound as a white powder (386 mg, 99.4% pure). (m/z): [M+H]$^+$ calcd for $C_{26}H_{39}N_3O_4$ 458.30; found, 458.4.

Example 201: Synthesis of 3-endo-(8-{2-[(2-hydroxyacetyl)-(2,2,3,3-tetramethyl-cyclopropylmethyl)amino]ethyl}-8-azabicyclo[3.2.1]oct-3-yl)-benzamide a. Preparation of (2,2,3,3-tetramethyl-cyclopropyl)methanol

To a stirred solution of 2,2,3,3-tetramethylcyclopetanecarboxylic acid (500 mg, 3.5 mmol) in THF (25 mL) was added 2.0 M borane dimethylsulfide complex in THF (1.8 mL, 3.5 mmol) at 0° C. The reaction mixture was warmed and stirred at 50° C. for 3 h. The solution was cooled to room temperature and methanol (10 mL) was carefully added. The reaction mixture was concentrated and filtered. The filtrate was concentrated to give the title intermediate as an oil (250 mg, 56%). $^1$H NMR (CDCl$_3$, 300 MHz) δ (ppm): 4.16 (t, J=4.8 Hz, 1H), 3.39 (dd, J=4.5, 7.5 Hz, 2H), 1.03 (s, 6H), 0.93 (s, 6H), 0.38 (t, J=7.5 Hz, 1H).

b. Preparation of 2,2,3,3-tetramethyl-cyclopropanecarbaldehyde

To a stirred solution of the product of the previous step and DIPEA (680 μL, 4.0 mmol) in DCM (5 mL) was added a solution of sulfur trioxide-pyridine complex (620 mg, 3.9 mmol) in DMSO (5 mL) at −20° C. After 2 h, the reaction was warmed to room temperature, diluted with DCM (20 mL) and washed with 1.0 N HCl (25 mL) and water (25 mL). The organics were separated, dried with anhydrous sodium sulfate, filtered, and concentrated. The crude material was purified by silica gel chromatography to give the title intermediate (45 mg, 18%).

c. Preparation of (2-hydroxyethyl)-carbamic Acid Benzyl Ester

To a stirred solution of ethanolamine (4.0 g, 66 mmol) in DCM (4 mL) was added benzyl chloroformate (4.6 mL, 33 mmol) at 0° C. After 1 h, the reaction mixture was warmed to room temperature and washed with 1.0N HCl (40 mL) and water (40 mL). The organics were separated, dried with anhydrous sodium sulfate, filtered, and concentrated. To a solution of the crude product in ethyl acetate (30 mL) was added hexanes (30 mL). The resulting crystals were filtered and dried to give the title intermediate as a white solid (4.5 g, 70%). $^1$H NMR (CDCl$_3$, 300 MHz) δ (ppm): 7.4-7.29 (m, 5H), 5.00 (s, 2H), 4.64 (t, J=5.5 Hz, 1H), 3.38 (q, J=6.0 Hz, 2H), 3.07 (t, J=6.0 Hz, 2H).

d. Preparation of (2-oxo-ethyl)-carbamic Acid Benzyl Ester

To a stirred solution of (2-hydroxyethyl)carbamic acid benzyl ester (1.0 g, 5.1 mmol) and DIPEA (1.78 mL, 10.2 mmol) in DCM (15 mL) was added a solution of sulfur trioxide-pyridine complex (1.63 g, 10.2 mmol) in DMSO (15 mL) at −20° C. After 1 h, the reaction was warmed to room temperature, diluted with dichloromethane (50 mL) and washed with 1.0 N HCl (50 mL) and brine. The organics were separated, dried with anhydrous sodium sulfate, filtered, concentrated, and purified by silica gel chromatography to give the title intermediate (810 mg, 82%). $^1$H NMR (CDCl$_3$, 300 MHz) δ (ppm): 9.5 (s, 1H) 7.4-7.2 (m, 5H), 5.1 (s, 2H), 3.9 (d, J=5.8 Hz, 2H), 2.9-3.3 (br, 1H).

e. Preparation of {2-[3-endo-(3-carbamoylphenyl)-8-azabicyclo[3.2.1]oct-8-yl]ethyl}-carbamic Acid Benzyl Ester A suspension of 3-endo-(8-azabicyclo[3.2.1]oct-3-yl)-benzamide and (2-oxo-ethyl)carbamic acid benzyl ester (0.99 g, 6.2 mmol) in DCM (20 mL) was sonicated for 5 min. To the stirred suspension was added sodium triacetoxyborohydride (1.3 g, 6.1 mmol). After stirring for 30 min, the reaction mixture was concentrated. The crude reaction mixture was diluted with ethyl acetate (50 mL) and washed with 1.0N NaOH (50 mL) and water (50 mL). The organics were separated, dried with anhydrous sodium sulfate, filtered, concentrated and purified by silica gel chromatography to provide the title intermediate (1.4 g, 57%). (m/z): [M+H]$^+$ calcd for $C_{24}H_{29}N_3O_3$, 408.22; found 408.5.

f. Preparation of 3-endo-[8-(2-aminoethyl)-8-azabicyclo[3.2.1]oct-3-yl]-benzamide A solution of the product of the previous step (1.4 g, 3.4 mmol) in methanol (20 mL) was added to palladium hydroxide on carbon (50 wt % water, 20% Pd on dry base, 140 mg). The reaction mixture was stirred under an atmosphere of hydrogen overnight. The solution was filtered through celite and concentrated to give an oil (1.0 g), which was used directly in the next step. (m/z): [M+H]$^+$ calcd for $C_{16}H_{23}N_3O$, 274.19; found 274.5.

g. Preparation of 3-endo-(8-{2-[(2,2,3,3-tetramethyl-cyclopropylmethyl)amino]ethyl}-8-azabicyclo[3.2.1]oct-3-yl)-benzamide To a solution of the product of the previous step (100 mg, 0.37 mmol) and the product of step b (45 mg, 0.37 mmol) in dichloromethane (2 mL) and methanol (0.2 mL) was added sodium triacetoxyborohydride (93 mg, 0.44 mmol). After stirring for 1 h, the reaction mixture was concentrated. The crude reaction mixture was diluted with ethyl acetate (20 mL) and washed with 1.0 N NaOH (20 mL). The organics were separated, dried with anhydrous sodium sulfate, filtered, and concentrated. The crude product was used h. Synthesis of 3-endo-(8-{2-[(2-hydroxyacetyl)-(2, 2,3,3-tetramethyl-cyclopropylmethyl)amino]ethyl}-8-azabicyclo[3.2.1]oct-3-yl)-benzamide To a solution of the product of the previous step (0.366 mmol) in DCM (2 mL) was added acetoxyacetyl chloride (50 µL, 0.44 mmol). After 1 h, the reaction mixture was concentrated and the resulting crude oil was stirred in methanol (2.0 mL) and 6.0 N NaOH (35 µL) overnight. The reaction mixture was concentrated and purified by preparative HPLC to give the TFA salt of the title compound (30.9 mg). (m/z): [M+H]$^+$ calcd for $C_{26}H_{39}N_3O_3$, 442.30; found 442.4.

Examples 202-203

Intermediates for Examples 202 and 203 were prepared as follows:

To a solution of 4-hydroxycyclohexanecarboxylic acid ethyl ester as a mixture of cis and trans isomers (8.7 g, 50.51 mmol) in THF (300 mL) at 0° C. was added imidazole (4.8 g, 70.72 mmol), DMAP (20 mol %, 1.23 g, 10.10 mmol) and tert-butyl dimethylchlorosilane (9.1 g, 60.61 mmol). The reaction mixture was warmed to room temperature, stirred overnight, and diluted with ethyl acetate and saturated aqueous ammonium chloride. The aqueous layer was extracted with ethyl acetate and the combined organic layers were washed with brine and dried over sodium sulfate. Solvent was removed and the crude oil was filtered through silica gel and solvent removed to give 4-(tert-butyldimethylsilanyloxy)cyclohexanecarboxylic acid ethyl ester (11.1 g, 77%) as a mixture of diastereomers.

To a solution of the product of the previous step (11.1 g, 38.7 mmol) in MTBE (150 mL) and methanol (2.35 mL, 58.11 mmol) was added lithium borohydride (1.27 g, 58.11 mmol). The reaction mixture was heated to 50° C. for 2 h, cooled to room temperature and quenched with methanol. The solution was diluted with ethyl acetate, washed with saturated aqueous sodium bicarbonate and brine, and dried over magnesium sulfate. Solvent was removed in vacuo to give crude [4-(tert-butyldimethylsilanyloxy)cyclohexyl] methanol as a mixture of diastereomers. Crude material was purified via silica gel chromatography (10-40% ethyl acetate/hexanes) to separate cis and trans diastereomers. Top spot (cis isomer)$^1$H NMR (300 mHz, CD$_3$OD): 3.91-3.95 (m, 1H), 3.31-3.32 (d, 2H), 1.61-1.63 (m, 2H), 1.36-1.46 (m, 7H), 0.85-0.86 (s, 9H), 0.00 (s, 6H). Bottom spot (trans isomer)$^1$H NMR data (300 mHz, CD$_3$OD): 3.49-3.53 (m, 1H), 3.27-3.28 (d, 2H), 1.81-1.84 (m, 2H), 1.71-1.74 (m, 2H), 1.28-1.36 (m, 1H), 1.18-1.26 (m, 2H), 0.93-0.97 (m, 2H), 0.82-0.84 (s, 9H), 0.00 (s, 6H).

Example 202: Synthesis of 3-endo-(8-{2-[(trans-4-hydroxycyclohexylmethyl)-((S)-2,3-dihydroxypropionyl)amino]ethyl}-8-azabicyclo[3.2.1]oct-3-yl)-benzamide a. Preparation of toluene-4-sulfonic Acid trans-4-(tert-butyldimethylsilanyloxy)-cyclohexylmethyl Ester To a solution of trans-[4-(tert-butyldimethylsilanyloxy) cyclohexyl]methanol (555 mg, 2.24 mmol) in DCM (20 mL) at 0° C. was added DIPEA (0.59 mL, 3.37 mmol), DMAP (20 mol %, 54 mg), and p-toluene-sulfonyl chloride (570 mg, 2.68 mmol). The reaction mixture was stirred at room temperature for 2 h, DABCO (250 mg) was added. The reaction mixture was stirred overnight. The solution was diluted with DCM, washed with saturated aqueous sodium bicarbonate and brine, and dried over sodium sulfate. Solvent was removed in vacuo to give the title intermediate. $^1$H NMR (300 mHz, CD$_3$OD): 7.75-7.77 (d, 2H), 7.40-7.42 (d, 2H), 3.80-3.81 (d, 1H), 3.45-3.51 (m, 1H), 2.40 (s, 3H) 1.78-1.82 (m, 2H), 1.62-1.71 (m, 2H), 1.48-1.58 (m, 1H), 1.30-1.33 (m, 1H), 1.15-1.21 (m, 2H), 0.85-1.00 (m, 2H), 0.85-0.90 (s, 9H), 0.00 (s, 6H).

b. Preparation of 2-{[trans-4-(tert-butyldimethylsilanyloxy)cyclohexylmethyl]amino}-ethanol To a solution of toluene-4-sulfonic acid trans-4-(tert-butyldimethylsilanyloxy)-cyclohexylmethyl ester (600 mg, 1.50 mmol) in acetonitrile (15 mL) was added ethanolamine (2.0 mL, 25 eq). The solution was heated to 50° C. overnight. The reaction was diluted with DCM (200 mL), washed with saturated aqueous sodium bicarbonate and brine, and dried over potassium carbonate. Solvent was removed to give crude title intermediate (0.44 g) as a yellow oil. (m/z): [M+H]$^+$ calcd for $C_{15}H_{33}NSiO_2$, 288.3; found 288.2.

c. Preparation of [trans-4-(tert-butyldimethylsilanyloxy) cyclohexylmethyl]-(2-hydroxy-ethyl)-carbamic Acid tert-butyl Ester To a solution of the product of the previous step (0.44 g, 1.50 mmol) in DCM (30 mL) was added di-tert-butyl dicarbonate (324 mg, 1.48 mmol). The reaction mixture was stirred at room temperature for 2 h, diluted with DCM (100 mL), washed with saturated aqueous sodium bicarbonate and brine, and dried over potassium carbonate. Solvent was removed to give the title intermediate (0.496 g) as a yellow oil.

d. Preparation of [trans-4-(tert-butyldimethylsilanyloxy)cyclohexylmethyl]-(2-oxo-ethyl)carbamic Acid tert-butyl Ester To a solution of the product of the previous step (496 mg, 1.27 mmol) in DCM (20 mL) at −15° C. was added DMSO (12.7 mmol, 0.905 mL) and DIPEA (1.103 mL, 6.35 mmol). The reaction was stirred for 10 min, and pyridine-sulfur trioxide complex (1.01 g, 6.35 mmol) was added. The reaction mixture was stirred for 1 h, warmed to room temperature, diluted with DCM (50 mL), washed with saturated aqueous sodium bicarbonate and brine, and dried over sodium sulfate. Solvent was removed in vacuo to give the title intermediate (480 mg) as a yellow oil.

e. Preparation of [trans-4-(tert-butyldimethylsilanyloxy) cyclohexylmethyl]-{2-[3-endo-(3-carbamoylphenyl)-8-azabicyclo[3.2.1]oct-8-yl]-ethyl}carbamic Acid tert-butyl Ester To a solution of the product of the previous step (480 mg, 1.24 mmol) in DCM (20 mL) was added 3-endo-(8-azabicyclo[3.2.1]oct-3-yl)-benzamide (343 mg, 1.48 mmol). The reaction mixture was stirred for 30 min, then sodium triacetoxyborohydride (525 mg, 2.48 mmol) was added. The reaction mixture was stirred for 2 h at room temperature, diluted with DCM (100 mL), washed with saturated aqueous sodium bicarbonate and brine, and dried over sodium sulfate. Solvent was removed in vacuo to give crude title intermediate (700 mg, 94%) as a crunchy yellow solid. (m/z): [M+H]$^+$ calcd for $C_{34}H_{58}N_3SiO_4$, 600.4; found 600.6.

f. Preparation of 3-endo-(8-{2-(trans-4-hydroxycyclohexylmethyl)aminol-ethyl}-8-azabicyclo[3.2.1]oct-3-yl)-benzamide The product of the previous step (700 mg, 1.16 mmol) was dissolved in DCM (15 mL) and trifluoroacetic acid was added (7 mL). The reaction mixture was stirred for 2 h at room temperature and then diluted with DCM (100 mL) and 1N NaOH (100 mL). The aqueous layer was extracted with dichloromethane (2×25 mL) and combined organic layers were washed with brine and dried over sodium sulfate. Solvent was removed in vacuo to give crude title intermediate (425 mg, 94% yield). (m/z): [M+H]$^+$ calcd for $C_{23}H_{36}N_3O_2$, 386.3; found 386.5.

g. Preparation of (S)-2,2-dimethyl-[1,3]dioxolane-4-carboxylic acid {2-[3-endo-(3-carbamoyl-phenyl)-8-azabicyclo[3.2.1]oct-8-yl]ethyl}-(trans-4-hydroxycyclohexylmethyl)amide To a solution of the product of the previous step (425 mg, 1.10 mmol) in DMF (15 mL) was added lithium (S)-2,2-dimethyl-[1,3]dioxolane-4-carboxylate (0.19 g., 1.21 mmol) and HATU (0.46 g, 1.21 mmol). The reaction mixture was stirred at room temperature overnight, diluted with DCM (100 mL), washed with water, 1:1 water:saturated aqueous sodium bicarbonate, and brine, then dried over potassium carbonate. Solvent was removed in vacuo to give crude titled intermediate as a yellow oil. (m/z): [M+H]$^+$ calcd for $C_{29}H_{43}N_3O_5$, 514.3; found 514.5.

h. Synthesis of 3-endo-(8-{2-[(trans-4-hydroxcyclohexylmethyl)-((S)-2,3-dihydroxypropionyl)amino]ethyl}-8-azabicyclo[3.2.1]oct-3-yl)-benzamide The product of the previous step was dissolved in acetonitrile (15 mL) and 1N HCl (15 mL) and the solution was stirred at room temperature for 2 h. The reaction mixture was diluted with DCM (200 mL) and 1N NaOH (150 mL). The aqueous layer was extracted with dichloromethane (2×50 mL) and combined organic layers were washed with brine and dried over sodium sulfate. Solvent was removed in vacuo and the crude material was purified by preparative HPLC to give the TFA salt of the title compound (45 mg) as a white powder. (m/z): [M+H]$^+$ calcd for $C_{26}H_{39}N_2O_5$, 474.29; found 474.4. $^1$H NMR (300 mHz, CD$_3$OD): 8.00-8.02 (s, 1H), 7.65-7.80 (m, 2H), 7.40-7.45 (t, 1H), 4.59-4.62 (m, 1H), 3.95-4.20 (m, 3H) 3.65-3.79 (m, 2H), 3.40-3.60 (m, 2H), 3.10-3.20 (m, 2H), 2.05-2.19 (m, 2H), 1.95-2.00 (m, 2H), 1.40-1.85 (m, 4H), 1.20-1.35 (m, 2H), 1.01-1.20 (m, 2H).

Example 203: Synthesis of 3-endo-(8-{2-[(cis-4-hydroxycyclohexylmethyl)-((S)-2,3-dihydroxypropionyl)amino]ethyl}-8-azabicyclo[3.2.1]oct-3-yl)-benzamide Following the procedure of Example 202, using the corresponding cis isomer, cis-[4-(tert-butyldimethylsilanyloxy)cyclohexyl]methanol in step a, the title compound was prepared. (m/z): [M+H]$^+$ calcd for $C_{26}H_{39}N_2O_5$, 474.29; found 474.4. $^1$H NMR (300 mHz, CD$_3$OD): 8.00-8.02 (s, 1H), 7.65-7.80 (m, 2H), 7.40-7.50 (t, 1H), 4.60-4.62 (m, 1H), 3.95-4.20 (m, 3H) 3.65-3.79 (m, 2H), 3.40-3.60 (m, 2H), 3.10-3.20 (m, 2H), 2.05-2.19 (m, 2H), 1.40-1.85 (m, 6H), 1.20-1.30 (m, 4H).

Example 204: Synthesis of 3-endo-(8-{2-[cyclohexylmethyl-((S)-2,3-dihydroxypropionyl)amino]ethyl}-8-azabicyclo[3.2.1]oct-3-yl)-benzoic Acid a. Preparation of 3-endo-(8-azabicyclo[3.2.1]oct-3-yl)-benzoic Acid Methyl Ester 3-endo-(8-Azabicyclo[3.2.1]oct-3-yl)-benzamide (2.5 g, 9.36 mmol) was weighed into a 200 mL flask and purged with nitrogen. Methanol (100 mL) was added followed by hydrochloride acid in dioxane (7 mL of 4.0 N solution, 28 mmol). The solution was heated to reflux and stirred overnight. The methanol was removed via evaporation and the reaction mixture was diluted with DCM (200 mL) and 1N NaOH (150 mL). The aqueous layer was extracted with DCM (2×50 mL) and combined organic layers were washed with brine and dried over sodium sulfate. Solvent was removed and the crude residue was purified by preparative HPLC. Pure fractions were combined to give the title intermediate (1.66 g) as a white powder. (m/z): [M+H]$^+$ calcd for $C_{15}H_{20}NO_2$, 246; found 246.3.

b. Preparation of 3-endo-{8-[2-(benzyloxycarbonylcyclohexylmethylamino)ethyl]-8-azabicyclo[3.2.1]oct-3-yl}benzoic Acid Methyl Ester To a solution of the product of the previous step (1.66 g, 4.61 mmol) in DCM (20 mL) and methanol (20 mL) was added cyclohexylmethyl-(2-oxoethyl)-carbamic acid benzyl ester (1.27 g, 4.61 mmol). The reaction mixture was stirred for 20 min, then sodium triacetoxyborohydride (1.95 g, 9.22 mmol) was added. The reaction mixture was stirred for 2 h, and then diluted with DCM (100 mL), washed with saturated aqueous sodium bicarbonate and brine, and dried over sodium sulfate. Solvent was removed in vacuo to give the title intermediate (2.65 g, >100% yield) as a crunchy yellow solid which was used directly in the next step.

c. Preparation of 3-endo-{8-[2-(cyclohexylmethylamino)ethyl]-8-aza-bicyclo[3.2.1]oct-3-yl}benzoic Acid Methyl Ester To a solution of the product of the previous step (2.65 g) in ethanol (20 mL) and 1N aqueous HCl (10 mL) was added palladium on carbon (10 wt. %, 270 mg). The reaction was purged with hydrogen gas and stirred under hydrogen overnight. The catalyst was removed via filtration and the reaction was diluted with DCM (200 mL) and 1N NaOH (150 mL). The aqueous layer was extracted with DCM (2×50 mL) and combined organic layers were washed with brine and dried over sodium sulfate. Solvent was removed to give the title intermediate (2.0 g) as a waxy yellow oil. (m/z): [M+H]$^+$ calcd for $C_{24}H_{36}N_2O_2$, 385.3; found 385.5.

d. Preparation of 3-endo-(8-{2-[cyclohexylmethyl-((S)-2,2-dimethyl-[1,3]dioxolane-4-carbonyl)amino]ethyl}-8-azabicyclo[3.2.1]oct-3-yl)benzoic Acid Methyl Ester To a solution of the product of the previous step (2.0 g, 5.2 mmol) in DMF (35 mL) was added lithium (S)-2,2-dimethyl-[1,3]dioxolane-4-carboxylate (0.72 g, 5.7 mmol) and HATU (2.18 g, 5.7 mmol). The reaction mixture was stirred at room temperature overnight, and then diluted with DCM (100 mL), washed with water, 1:1 water:saturated aqueous sodium bicarbonate, and brine, then dried over potassium carbonate. Solvent was removed in vacuo to give crude title intermediate as a brown oil that was used directly in the next step.

e. Preparation of 3-endo-(8-{2-[cyclohexylmethyl-((S)-2,3-dihydroxypropionyl)amino]-ethyl}8-azabicyclo[3.2.1]oct-3-yl)benzoic Acid Methyl Ester The product of the previous step was dissolved in acetonitrile (15 mL) and 1N HCl (15 mL) and the solution was stirred at room temperature for 2 h. The reaction mixture was diluted with DCM (200 mL) and 1N NaOH (150 mL). The aqueous layer was extracted with DCM (2×50 mL) and combined organic layers were washed with brine and dried over sodium sulfate. Solvent was removed in vacuo to give the title intermediate (2.2 g) as a yellow oil. (m/z): $[M+H]^+$ calcd for $C_{27}H_{40}N_2O_5$, 473.3; found 473.3.

f. Synthesis of 3-endo-(8-{2-[cyclohexylmethyl-((S)-2,3-dihydroxypropionyl)amino]ethyl}-8-azabicyclo[3.2.1]oct-3-yl)benzoic Acid To a solution of the product of the previous step (2.2 g, 5.2 mmol) in THF (5 mL) was added a solution of lithium hydroxide (1.31 g, 31.2 mmol) in water (5 mL). The solution was stirred vigorously at room temperature. When the ester hydrolysis was complete, the THF was removed in vacuo and the residue was purified by preparative HPLC. Pure fractions were combined to give the title compound (0.32 g) as a white powder. (m/z): $[M+H]^+$ calcd for $C_{26}H_{38}N_2O_5$, 459.28; found 459.5.

Assay 1: Radioligand Binding Assay on Human Mu, Human Delta and Guinea Pig Kappa Opioid Receptors a. Membrane Preparation CHO-K1 (Chinese Hamster Ovary) cells stably transfected with human mu opioid or with guinea pig kappa receptor cDNA were grown in medium consisting of Ham's-F12 media supplemented with 10% FBS, 100 units/ml penicillin—100 µg/mL streptomycin and 800 µg/mL Geneticin in a 5% $CO_2$, humidified incubator @ 37° C. Receptor expression levels ($B_{max}$~2.0 and ~0.414 pmol/mg protein, respectively) were determined using [$^3$H]-Diprenorphine (specific activity ~50-55 Ci/mmol) in a membrane radioligand binding assay.

Cells were grown to 80-95% confluency (<25 subculture passages). For cell line passaging, the cell monolayer was incubated for 5 minutes at room temperature and harvested by mechanical agitation in 10 mL of PBS supplemented with 5 mM EDTA. Following resuspension, cells were transferred to 40 mL fresh growth media for centrifugation for 5 minutes at 1000 rpm and resuspended in fresh growth medium at the appropriate split ratio.

For membrane preparation, cells were harvested by gentle mechanical agitation with 5 mM EDTA in PBS followed by centrifugation (2500 g for 5 minutes). The pellets were resuspended in Assay Buffer (50 mM 4-(2-hydroxyethyl) piperazine-1-ethanesulfonic acid N-(2-hydroxyethyl)piperazine-N'-(2-ethanesulfonic acid) (HEPES)), pH 7.4, and homogenized with a polytron disrupter on ice. The resultant homogenates were centrifuged (1200 g for 5 minutes), the pellets discarded and the supernatant centrifuged (40,000 g for 20 minutes). The pellets were washed once by resuspension in Assay Buffer, followed by an additional centrifugation (40,000 g for 20 minutes). The final pellets were resuspended in Assay Buffer (equivalent 1 T-225 flask/1 mL assay buffer). Protein concentration was determined using a Bio-Rad Bradford Protein Assay kit and membranes were stored in frozen aliquots at −80° C., until required.

Human delta opioid receptor (hDOP) membranes were purchased from Perkin Elmer. The reported $K_d$ and $B_{max}$ for these membranes determined by saturation analyses in a [$^3$H]-Natrindole radioligand binding assays were 0.14 nM ($pK_d$=9.85) and 2.2 pmol/mg protein, respectively. Protein concentration was determined using a Bio-Rad Bradford Protein Assay kit. Membranes were stored in frozen aliquots at −80° C., until required.

b. Radioligand Binding Assays

Radioligand binding assays were performed in an Axygen 1.1 mL deep well 96-well polypropylene assay plate in a total assay volume of 200 µL containing the appropriate amount of membrane protein (~3, ~2 and ~20 µg for mu, delta and kappa, respectively) in Assay Buffer, supplemented with 0.025% bovine serum albumin (BSA). Saturation binding studies for determination of $K_d$ values of the radioligand were performed using [$^3$H]-Diprenorphine at 8-12 different concentrations ranging from 0.001 nM-5 nM. Displacement assays for determination of pKi values of compounds were performed with [$^3$H]-Diprenorphine at 0.5, 1.2, and 0.7 nM for mu, delta, and kappa, respectively, and eleven concentrations of compound ranging from 10 pM-100 µM.

Binding data were analyzed by nonlinear regression analysis with the GraphPad Prism Software package (GraphPad Software, Inc., San Diego, Calif.) using the 3-parameter model for one-site competition. The curve minimum was fixed to the value for nonspecific binding, as determined in the presence of 10 µM naloxone. $K_i$ values for test compounds were calculated, in Prism, from the best fit $IC_{50}$ values, and the $K_d$ value of the radioligand, using the Cheng-Prusoff equation $(K_i=IC_{50}/(1+([L]/K_d)))$ where [L]=the concentration of [$^3$H]-Diprenorphine. Results are expressed as the negative decadic logarithm of the $K_i$ values, $pK_i$.

Test compounds having a higher $pK_i$ value in these assays have a higher binding affinity for the mu, delta, or kappa opioid receptor. The compounds of Examples 1-204 were tested in these assays. With the exception of the compound of Example 204, which demonstrated binding at the mu receptor at the micromolar level, all of the compounds had a $pK_i$ value between about 8.0 to about 10.5 at the human mu opioid receptor. For example, the compounds of Examples 1, 46B, 58, 59, and 136, had $pK_i$ values of 10.1, 10.0, 9.9, 9.2, and 9.8, respectively. The compounds of Examples 1-203 also had $pK_i$ values between about 7.0 and about 10.5 at the human delta and guinea pig kappa opioid receptors.

Assay 2: Agonist Mediated Activation of the Mu-Opioid Receptor in Membranes Prepared from CHO-K1 Cells Expressing the Human Mu-Opioid Receptor In this assay, the potency and intrinsic activity values of test compounds were determined by measuring the amount of bound GTP-Eu present following receptor activation in membranes prepared from CHO-K1 cells expressing the human mu opioid receptor.

a. Mu Opioid Receptor Membrane Preparation

Human mu opioid receptor (hMOP) membranes were either prepared as described above or were purchased from Perkin Elmer. The reported $pK_d$ and $B_{max}$ for the purchased membranes determined by saturation analyses in a [$^3$H]-Diprenorphine radioligand binding assays was 10.06 and 2.4 pmol/mg protein, respectively. Protein concentration was determined using a Bio-Rad Bradford Protein Assay kit. Membranes were stored in frozen aliquots at −80° C., until required. Lyophilized GTP-Eu and GDP were diluted to 10 μM and 2 mM, respectively, in double distilled H$_2$O then mixed and permitted to sit at room temperature for 30 minutes prior to transfer to individual aliquots samples for storage at −20° C.

b. Human Mu GTP-Eu Nucleotide Exchange Assay

GTP-Eu nucleotide exchange assays were performed using the DELPHIA GTP-binding kit (Perkin/Elmer) in AcroWell 96 well filter plates according to the manufacturer's specifications. Membranes were prepared as described above, and prior to the start of the assay, aliquots were diluted to a concentration of 200 μg/mL in Assay Buffer (50 mM HEPES, pH 7.4 at 25° C.), then homogenized for 10 seconds using a Polytron homogenizer. Test compounds were received as 10 mM stock solutions in DMSO, diluted to 400 μM into Assay Buffer containing 0.1% BSA, and serial (1:5) dilutions then made to generate ten concentrations of compound ranging from 40 pM−80 μM—GDP and GTP-Eu were diluted to 4 μM and 40 nM, respectively, in Assay Buffer. The assay was performed in a total volume of 100 μL containing 5 μg of membrane protein, test compound ranging from 10 pM-20 μM), 1 μM GDP, and 10 nM GTP-Eu diluted in 10 mM MgCl$_2$, 50 mM NaCl, and 0.0125% BSA, (final assay concentrations). A DAMGO (Tyr-D-Ala-Gly-(methyl)Phe-Gly-ol) concentration-response curve (ranging from 12.8 pM-1 μM) was included on every plate.

Assay plates were prepared immediately prior to assay following the addition of 25 μL of Assay Buffer, 25 μL of test compound, and 25 μL GDP and GTP-Eu. The assay was initiated by the addition of 25 μL membrane protein and allowed to incubate for 30 minutes. The assay plates were then filtered with a Waters vacuum manifold connected to the house vacuum regulated to 10-12 in. Hg and washed with room temperature GTP Wash Solution (2×300 mL). The bottoms of the plates were blotted to remove excess liquid. The plates were then immediately read to determine the amount of bound GTP-Eu by measuring Time Resolved Fluorescence (TRF) on a Packard Fusion Plate ReaderVehicle: DMSO not to exceed 1% final assay concentration.

The amount of bound GTP-Eu is proportional to the degree of activation of the mu opioid receptors by the test compound. The intrinsic activity (IA), expressed as a percentage, was determined as the ratio of the amount of bound GTP-Eu observed for activation by the test compound to the amount observed for activation by DAMGO which is presumed to be a full agonist (IA=100). The compounds of Examples 1 to 204 demonstrated intrinsic activities in this assay of less than about 40, typically less than about 25. For example, the compounds of Examples 1, 46B, 58, 59, and 136, had IA values of 6, −3, −3, −2, and 14, respectively. Thus, the compounds of the present invention have been shown to act as antagonists at the human mu opioid receptor.

Assay 3: Mouse Model of In Vivo Efficacy

In these assays the efficacy of test compounds was evaluated in a model of gastrointestinal transit, which evaluates peripheral activity, as well as in an analgesia detection model utilizing a rodent hot plate, which evaluates central nervous system activity. Obtaining results from these two models enables calculation of relative peripheral selectivities of test compounds. These studies were approved by the Institutional Animal Care and Use Committee at Theravance, Inc. and conformed to the Guide for the Care and Use of Laboratory Animals published by the National Academy of Sciences (01996).

a. Mouse Intestinal Transit Assay

Test compounds were evaluated in the mouse intestinal transit assay to determine their ability to reverse morphine-induced delayed gastrointestinal transit. Mice were fasted up to 24 hours prior to administration of test compounds or vehicle by intravenous, subcutaneous, intramuscular or oral routes of administration at doses ranging from 0.001 to about 10 milligrams/kilogram (mg/kg). The administration of test compound was followed by subcutaneous administration of morphine at a dose of 3 mg/kg or vehicle. Five minutes post morphine or vehicle administration, a non-nutritive, non-absorbable charcoal meal was administered via oral gavage and animals were allowed free access to water for the sixty minute duration of the experiment. Animals were then euthanized via carbon dioxide asphyxiation followed by thoracotomy and the stomach to caecum was carefully excised. The stomach was ligated at the lower esophageal sphincter and the pyloric sphincter to prevent additional emptying into the small intestine during the period in which measurements were made. Intestinal transit was defined as the distance traveled by the leading front of the meal relative to the total intestinal length (at the ileocecal junction).

b. Mouse Hot Plate Assay

Activities of compounds were investigated in the mouse hot plate model (Letica Scientific Instruments Model #7406; Panlab, S.L., Barcelona, Spain) to determine their ability to reverse the centrally mediated action of morphine. Compounds were evaluated as to their ability to reverse morphine-induced analgesia as evidenced by decreases in paw lick latency relative to morphine controls. Test compounds were administered intravenously, subcutaneously, intramuscularly or orally at doses ranging from 0.1 to 30 mg/kg followed by subcutaneous administration of morphine at a dose of 10 mg/kg or of vehicle. Animals were then returned to their home cage for the thirty minute remainder of the experiment. Animals were subsequently placed on the hot plate apparatus (53° C.) and the time for the mouse to lick its paw was recorded by an observer blinded to the treatment group. Animals that failed to present paw lick behavior prior to a 35 second cut-off were automatically assigned a latency time of 35 seconds.

c. Data Analysis and Results

Data was analyzed using the GraphPad Prism Software package (GraphPad Software, Inc., San Diego, Calif.). Percent reversal curves were constructed by non-linear regression analysis using the sigmoidal dose response (variable slope) model and best-fit ID$_{50}$ values were calculated. Curve minima and maxima were fixed to morphine control values (indicating 0% reversal) and vehicle controls (indicating 100% reversal), respectively. Results are expressed as ID$_{50}$, the dose required for 50% reversal of the effects of morphine, in milligrams per kilogram. Selected compounds of the invention were tested in this model. Compounds of the invention administered subcutaneously or orally exhibited $ID_{50}$ values in the intestinal transit model of between about 0.1 and about 3 mg/kg.

Peripheral selectivity was calculated for each compound based on the hotplate $ID_{50}$ value (central measure) divided by the intestinal transit $ID_{50}$ value (peripheral measure). The compounds of the invention, which were tested in these assays, exhibited peripheral selectivities ranging from about 2 fold to about 500 fold. In particular, the compounds of Examples 46B, 48B, 58, 59, and 63 exhibited peripheral selectivities of 15, 30, 300, 43, and 22, respectively, following subcutaneous administration, and 19, 42, 35, 6, and 22, respectively, following oral administration.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. 3-endo-(8-{2-[(4,4-difluorocyclohexylmethyl)-(2-hydroxyacetyl)amino]ethyl}-8-azabicyclo[3.2.1]oct-3-yl)-benzamide or a pharmaceutically-acceptable salt thereof.

2. The compound of claim 1 which is the phosphate salt of 3-endo-(8-{2-[(4,4-difluorocyclohexylmethyl)-(2-hydroxyacetyl)amino]ethyl}-8-azabicyclo[3.2.1]oct-3-yl)-benzamide.

3. The compound of claim 1 which is 3-endo-(8-{2-[(4,4-difluorocyclohexylmethyl)-(2-hydroxyacetyl)amino]ethyl}-8-azabicyclo[3.2.1]oct-3-yl)-benzamide.

4. A pharmaceutical composition comprising the compound of claim 1 and a pharmaceutically acceptable carrier.

5. A method of treating a mammal having opioid-induced bowel dysfunction or post-operative ileus, the method comprising administering to the mammal, a therapeutically effective amount of a pharmaceutical composition comprising a pharmaceutically-acceptable carrier and a compound of claim 1.

6. The method of claim 5 wherein the mammal has opioid-induced bowel dysfunction.

7. The method of claim 5 wherein the mammal has post-operative ileus.

* * * * *